US008716437B2

(12) United States Patent
Goldstein et al.

(10) Patent No.: US 8,716,437 B2
(45) Date of Patent: May 6, 2014

(54) IDENTIFICATION OF TOXIN LIGANDS

(76) Inventors: Steven A. Goldstein, Chicago, IL (US);
Zoltan Takacs, Chicago, IL (US)

(*) Notice: Subject to any disclaimer, the term of this patent is extended or adjusted under 35 U.S.C. 154(b) by 196 days.

(21) Appl. No.: 12/746,410

(22) PCT Filed: Dec. 5, 2008

(86) PCT No.: PCT/US2008/013385
§ 371 (c)(1),
(2), (4) Date: Sep. 23, 2010

(87) PCT Pub. No.: WO2009/075773
PCT Pub. Date: Jun. 18, 2009

(65) Prior Publication Data
US 2011/0009283 A1 Jan. 13, 2011

Related U.S. Application Data

(60) Provisional application No. 61/012,209, filed on Dec. 7, 2007, provisional application No. 61/074,794, filed on Jun. 23, 2008.

(51) Int. Cl.
*A61K 38/00* (2006.01)
*C07K 5/00* (2006.01)

(52) U.S. Cl.
USPC ............................................ 530/324; 514/1.1

(58) Field of Classification Search
None
See application file for complete search history.

(56) References Cited

U.S. PATENT DOCUMENTS

| | | | |
|---|---|---|---|
| 5,143,854 | A | 9/1992 | Pirrung et al. |
| 5,223,409 | A | 6/1993 | Ladner et al. |
| 6,207,446 | B1 | 3/2001 | Szostak et al. |
| 8,043,829 | B2 * | 10/2011 | Sullivan et al. .......... 435/69.1 |
| 2003/0068672 | A1 | 4/2003 | Yu |
| 2003/0129659 | A1 | 7/2003 | Whelihan |
| 2005/0272093 | A1 | 12/2005 | MacKinnon |
| 2006/0264374 | A1 | 11/2006 | Gilly |
| 2007/0071764 | A1 | 3/2007 | Sullivan |

FOREIGN PATENT DOCUMENTS

| | | |
|---|---|---|
| WO | WO-94/03486 A1 | 2/1994 |
| WO | WO-99/18123 A1 | 4/1999 |
| WO | WO 99/51773 | 10/1999 |
| WO | WO 00/63701 | 10/2000 |
| WO | WO 01/40803 | 6/2001 |
| WO | WO 01/83827 | 11/2001 |
| WO | WO 01/98534 | 12/2001 |
| WO | WO 02/12893 | 2/2002 |
| WO | WO 03/029456 | 4/2003 |
| WO | WO-2006/116156 A2 | 11/2006 |
| WO | WO-2008/139243 | 11/2008 |

OTHER PUBLICATIONS

Ackerman et al., "Ion Channels—Basic Science and Clinical Disease" *New Engl. J. Med.* 336(22):1575-1586 (1997).
Altschul et al., "Gapped BLAST and PSI-BLAST: a new generation of protein database search programs" *Nucleic Acids REs.* 25(17):3389-3402 (1997).
Beeton et al., "Selective blockade of T lymphocyte K(+) channels ameliorates experimental autoimmune encephalomyelitis, a model for multiple sclerosis" *PNAS USA* 98(24):13942-13947 (2001).
Berge et al., "Pharmaceutical salts" *J. Pharm. Sci.* 66:1-19 (1977).
Daniel et al., "Screening for Potassium Channel Modulators by a High Through-Put 86-Rubidium Efflux Assay in a 96-Well Microtiter Plate" *J. Pharmacol. Meth.* 25:185-193 (1991).
De Wildt et al., "Antibody arrays for high-throughput screening of antibody-antigen interactions" *Nat. Biotechnol.* 18:989-994 (2000).
French and Terlau, "Sodium channel toxins—receptor targeting and therapeutic potential" *J. Med. Chem.* 11(23):3053-3064 (2004).
Garrard et al., "Fab assembly and enrichment in a monovalent phage display system" *Bio/Technology* 9(12):1373-1377 (1991).
Ge, "UPA, a universal protein array system for quantitative detection of protein-protein, protein-DNA, protein-RNA and protein-ligand interactions" *Nucleic Acids Res.* 28(2):e3;i-vii (2000).
Goldstein and Miller, "Mechanism of Charybdotoxin Block of a Voltage-Gated K+ Channel" *Biophys J.* 65:1613-1619 (1993).
Gutman et al., "International Union of Pharmacology. LIII. Nomenclature and Molecular Relationships of Voltage-Gated Potassium Channels" *Pharmacol. Rev.* 57(4):473-508 (2005).
Hamill, "Improved patch-clamp techniques for high-resolution current recording from cells and cell-free membrane patches" *Pflugers Arch.* Aug. 1981;391(2):85-100.
Henikoff & Henikoff, *Proc. Natl. Acad. Sci. USA* 89:10915 (1989).
Hogan et al., "URSA: ultra rapid selection of antibodies from an antibody phage display library" *Biotechniques* 38:536-538 (2005).
Holevinsky et al., "ATP-sensitive K+ Channel Opener Acts as a Cl⁻ Channel Inhibitor in Vascular Smooth Muscle Cells" *J. Membrane Biology* 137:59-70 (1994).
International Search Report for PCT/US08/13385, mailed on Jun. 9, 2009.
Karatan et al., "Molecular Recognition Properties of FN3 Monobodies that Bind the Src SH3 Domain" *Chem & Biol.* 11:835-844 (2004).
Karlin & Altschul, "Applications and statistics for multiple high-scoring segments in molecular sequences" *Proc. Nat'l. Acad. Sci. USA*, 90:5873-5787 (1993).
Koide et al., "The fibronectin type III domain as a scaffold for novel binding proteins" *J. Mol. Biol.*, 284(4):1141-1151 (1998).
Koo et al., "Blockade of the Voltage-Gated Potassium Channel Kv1.3 Inhibits Immune Responses in Vivo" *J. Immunol.* 5120-5128 (1997).
Legros et al., "Evidence for a new class of scorpion toxins active against K+ Channels" *FEBS Letters* 431:375-380 (1998).
Lueking et al., "Protein Microarrays for Gene Expression and Antibody Screening" *Anal. Biochem.* 270:103-111 (1999).
MacBeath and Schreiber, "Printing proteins as microarrays for high-throughput function determination" *Science* 289:1760-1763 (2000).
Meuth et al., "TWIK-related acid-sensitive K+ channel 1 (TASK1) and TASK3 critically influence T lymphocyte effector functions" *J. Biol. Chem.* 283(21):14559-14570 (2008).

(Continued)

*Primary Examiner* — Celine Qian
(74) *Attorney, Agent, or Firm* — Choate, Hall & Stewart LLP

(57) ABSTRACT

The disclosure relates to a method and system of screening for ligands which specifically bind to receptors. The method comprises expressing at least one receptor. The at least one receptor is contacted with a sample comprising at least one ligand. Whether the ligand selectively binds to the receptor is determined.

6 Claims, 17 Drawing Sheets

(56) References Cited

OTHER PUBLICATIONS

Mouhat et al., "Diversity of folds in animal toxins acting on ion channels" 378(Pt 3):717-26 (2004).
NCBI Accession No. NM_002232.
NCBI Accession No. NM_010610.
NCBI Accession No. NM_012970.
NCBI Accession No. NM_173095.
Suarez-Kurtz et al., "Peptidyl Inhibitors of *Shaker*-Type $K_v1$ Channels Elicit Twitches in Guinea Pig Ileum by Blocking $K_v1.1$ at Enteric Nervous System and Enhancing Acetylcholine Release" *J Pharmacol Exp Ther*. 289 (3):1517-1522 (1999).
Vestergarrd-Bogind et al., "Single-File Diffusion through the $Ca^{2+}$-Activated $K^+$ Channel of Human Red Cells" *J. Membrane Biol*. 88:67-75 (1988).
Vianna- Jorge et al., "Shaker-type Kv1 channel blockers increase the peristaaltic activity of guinea-pig ileum by stimulating acetylcholine and tachykinins release by the enteric nervous system" *Br J Pharmacol*. 138(1):57-62 (2003).
Abbas, N. et al., A new Kaliotoxin selective towards Kv1.3 and Kv1.2 but not Kv1.1 channels expressed in oocytes, Biochem. Biophys. Res. Commun., 376:525-530 (2008).
Alphonse, S. et al., Chain A, Solution Structure of Aosk1, NCBI/GenBank 2CK4_A (2012).
Crest, M. et al, Kaliotoxin, a Novel Peptidyl Inhibitor of Neuronal BK-Type Ca2+-activated K+ Channels Characterized from Androctonus mauretanicus Venom, J. Biol.Chem., 267(3):1640-1647 (1992).
Dauplais, M. et al., Determination of the Three-Dimensional Solution Structure of Noxiustoxin: Analysis of Structural Differences with Related Short-Chain Scorpion Toxins, Biochem., 34:16563-16573 (1995).
Gao, B. et al., A potent potassium channel blocker from Mesobuthus eupeus scorpion venom, Biochimie, 92:1847-1853 (2010).
Garcia, M.L. et al., Purification and Characteriozation of Three Inhibitors of Voltage-Dependent K+ Channels from Leiurus quinquestriatus var. hebraeus Venom, Biochem., 33:6834-6839 (1994).
Garcia-Calvo, M. et al., Purification, Characterization, and Biosynthesis of Margatoxin, a Component of Centruroides margaritatus Venom That Selectively Inhibits Voltage-dependent Potassium Channels, J. Biol. Chem., 268(25): 18866-18874 (1993).
Koschak, A. et al, Subunit Composition of Brain Voltage-gated Potassium Channels Determined by Hongotoxin-1, a Novel Peptide Derived from Centruroides limbatus Venom, J. Biol. Chem., 273(5):2639-2644 (1998).
Martin, B.M. et al., Novel K+-channel-blocking toxins from the venom of the scorpion Centruroides limpidus limpidus Karsch, Biochem. J., 304(51-56):51-56 (1994).
Panyi, G. et al., K+ Channel Blockers: Novel Tools to Inhibit T Cell Activation Leading to Specific Immunosuppression, Curr. Pharm. Design, 12:2199-2220 (2006).
Possani, L.D. eta al., The Primary Structure of Noxiustoxin: A K+ Channel Blocking Peptide, Purified from the Venom of the Scorpion Centruroides Noxius Hoffmann, Carlsberg Res. Commun., 47:285-289 (1982).
Zilberberg, N. et al., Putative Potassium Channel Toxin Tx821 [Buthus occitanus israelis], NCBI/GenBank (2008).
Gazarian, T. et al., Isolation and structure-functional characterization of phage display library-derived mimotopes of noxiustoxin, a neurotoxin of the scorpion Centruroides noxius Hoffmann, Molecular Immunology, 37:755-766 (2000).
Legros, C. et al., Engineering-Specific Pharmacological Binding Sites for Peptidyl Inhibitors of Potassium Channels into KcsA, Biochemistry, 41:15369-15375 (2002).
Olamendi-Portugal, T. et al., Novel Alpha-KTx peptides from the venom of the scorpion Centruroides elegans selectively blockade Kv1.3 over IKCal K+ channels of T cells, Toxicon, 46:418-429 (2005).
Takacs, Z. et al., A designer ligand specific for Kv1.3 channels from a scorpion neurotoxin-based library, PNAS, 106(52): 22211-22216 (2009).

\* cited by examiner

...MKKLLFAIPLVVPFYSMAAE**GVEINVKCSGSPQCLKPCKDAGMRFGKCMN
RKCHCTPK**GSASS*ATRPFVCEYQGQSSDLPQPPVNAGGGSGGGSGGGSEGGGSEG
GGSEGGGSEGGGSGGGSGSGDFYEKMANANKGAMTENADENALQSDAKGKLDSVA
TDYGA*...

...leaderlinkerkaliotoxinlinker*phagemid*...

FIG. 1

| sample | toxin library confirmation |
|---|---|
| 1 | MAAEGVEINVKCSGSPQCLRPCKDRFGQHAGGKCMNRKCKCFGRGSASSATRPFVCEYQGQSSDLP |
| 2 | MAAEGVEINVKCSGSPQCLEPCKKAGMRFGKCMNGKCHCGSASSATRPFVCEYQGQSSDLP |
| 3 | nonspecific |
| 4 | MAAEGVEINVKCSGSPQCIKPCKDAGMRFGKCMNGKCHCGSASSATRPFVCEYQGQSSDLP |
| 5 | MAAEGVEINVKCSGSPQCLRPCKDRFGQHAGGKCMNRKCKCFGRGSASSATRPFVCEYQGQSSDLP |
| 6 | nonspecific |
| 7 | nonspecific |
| 8 | nonspecific |
| 9 | nonspecific |
| 10 | nonspecific |
| 11 | MAAEGVEINVKCSGSPQCIKPCKDAGMRFGKCMNGKCDCTPKGSASSATRPFVCEYQGQSSDLP |
| 12 | nonspecific |
| 13 | MAAEGVEINVKCSGSPQCLRPCKDRFGQHAGGKCMNRKCKCFGRGSASSATRPFVCEYQGQSSDLP |
| 14 | nonspecific |
| 15 | nonspecific |
| 16 | nonspecific |
| 17 | MAAEGVEINVKCSGSPQCLEPCKKAGMRFGKCMNGKCRCYSGSASSATRPFVCEYQGQSSDLP |
| 18 | MAAEGVEINVKCSGSPQCLKPCKKAGMRFGKCMNKRCYGSASSATRPFVCEYQGQSSDLP |
| 19 | nonspecific |
| 20 | MAAEGVEINVKCSGSPQCLEPCKKAGMRFGKCMMSKCRCYSGSASSATRPFVCEYQGQSSDLP |
| 21 | nonspecific |
| 22 | MAAEGFTNVSCTTSKQCWTPCKKAIGSLQSKCMMSKCRCYSGSASSATRPFVCEYQGQSSDLP |
| 23 | MAAEGFTNVSCTTSKQCLPPCKAQFGIRAGAKCMNGKCHCGSASSATRPFVCEYQGQSSDLP |
| 24 | MAAEGFTNVSCTTSKQCWSVCKDLFGVDRGKCMNKRCYGSASSATRPFVCEYQGQSSDLP |
| 25 | MAAEGFTNVSCTTSKQCYPHCKKETGYPNAKCMNKRCYGSASSATRPFVCEYQGQSSDLP |
| 26 | nonspecific |
| 27 | MAAEGFTNVSCTTSKQCWTPCKKAIGSLQSKCMNGKCHCTPKGSASSATRPFVCEYQGQSSDLP |
| 28 | nonspecific |
| 29 | MAAEGFTNVSCTTSKQCYPHCKKETGYPNAKCMNKKCRCYGSASSATRPFVCEYQGQSSDLP |
| 30 | nonspecific |
| 31 | MAAEGFTNVSCTTSKQCWSICKRLHNTNRGKCMNGKCKCYNNGSASSATRPFVCEYQGQSSDLP |
| 32 | nonspecific |
| 33 | nonspecific |
| 34 | nonspecific |
| 35 | nonspecific |
| 36 | MAAEGFTNVSCTTSKQCWSVCQRLHNTSRGKCMNGKCKCYNGGSASSATRPFVCEYQGQSSDLP |
| 37 | MAAEGFTNVSCTTSKQCWSICKRLHNTNRGKCMNGKCKCYPHGSASSATRPFVCEYQGQSSDLP |

FIG. 2

| 38 | MAAEGFTNVSCTTSKQCWSICKRLHNTNRGKCMNRKCHCTPKGSASSATRPFVCEYQGQSSDLP |
|---|---|
| 39 | MAAEGFTNVSCTTSKQCWPVCKKLFGTYRGKCMNGKCHCTPQGSASSATRPFVCEYQGQSSDLP |
| 40 | MAAEGFTNVSCTTSKQCWIACKKVTGSTQGKCMNGKCHCGSASSATRPFVCEYQGQSSDLP |
| 41 | MAAEVRIPVSCKHSGQCSKPCKELYGSSAGAKCMNGKCHCTPQGSASSATRPFVCEYQGQSSDLP |
| 42 | MAAEVRIPVSCKHSGQCIKPCKDAGMRFGKCMNKKCRCYSGSASSATRPFVCEYQGQSSDLP |
| 43 | nonspecific |
| 44 | nonspecific |
| 45 | nonspecific |
| 46 | MAAEVRIPVSCKHSGQCLKPCKDAGMRFGKCMNGKCRCYSGSASSATRPFVCEYQGQSSDLP |
| 47 | MAAEVRIPVSCKHSGQCLEPCKKAGMRFGKCMMSKCRCYSGSASSATRPFVCEYQGQSSDLP |
| 48 | MAAEVRIPVSCKHSGQCSKPCKELYGSSAGAKCMNRKCKCFGRGSASSATRPFVCEYQGQSSDLP |
| 49 | nonspecific |
| 50 | MAAEVRIPVSCKHSGQCIKPCKDAGMRFGKCMNGKCRCYSGSASSATRPFVCEYQGQSSDLP |
| 51 | MAAEVRIPVSCKHSGQCLKPCKDLYGPHAGAKCMNGKCHCGSASSATRPFVCEYQGQSSDLP |
| 52 | MAAEVRIPVSCKHSGQCIQPCRDAGMRFGKCMNGKCHCTPKGSASSATRPFVCEYQGQSSDLP |
| 53 | nonspecific |
| 54 | MAAEVRIPVSCKHSGQCSKPCKELYGSSAGAKCMNKKCRCYSGSASSATRPFVCEYQGQSSDLP |
| 55 | MAAEVRIPVSCKHSGQCLRPCKDRFGQHAGGKCMNGKCKCYNNGSASSATRPFVCEYQGQSSDLP |
| 56 | MAAEVRIPVSCKHSGQCIKPCKDAGMRFGKCMNRKCKCFGRGSASSATRPFVCEYQGQSSDLP |
| 57 | nonspecific |
| 58 | MAAEVRIPVSCKHSGQCLKPCKDLYGPHAGAKCMNGKCDCTPKGSASSATRPFVCEYQGQSSDLP |
| 59 | MAAEVRIPVSCKHSGQCLKPCKDAGMRFGKCMNKKCRCYSGSASSATRPFVCEYQGQSSDLP |
| 60 | nonspecific |
| 61 | nonspecific |
| 62 | nonspecific |
| 63 | MAAEGFTDVDCSVSKQCXPVCKKLFGTYRGKCMNGKCKCYGSASSATRPFVCEYQGQSSDLP |
| 64 | MAAEGFTDVDCSVSKQCWSICKRLHNTNRGKCMNGKCKCYNNGSASSATRPFVCEYQGQSSDLP |
| 65 | MAAEGFTDVDCSVSKQCWPVCKKLFGTYRGKCMMSKCRCYSGSASSATRPFVCEYQGQSSDLP |
| 66 | MAAEGFTDVDCSVSKQCYPHCKKETGYPNAKCMNGKCRCYSGSASSATRPFVCEYQGQSSDLP |
| 67 | MAAEGFTDVDCSVSKQCWIACKKVTGSTQGKCMNGKCRCYSGSASSATRPFVCEYQGQSSDLP |
| 68 | nonspecific |
| 69 | MAAEGFTDVDCSVSKQCWIACKKLFGTYRGKCMMSKCRCYSGSASSATRPFVCEYQGQSSDLP |
| 70 | MAAEGFTDVDCSVSKQCWSVCQRLHNTSRGKCMMSKCRCYSGSASSATRPFVCEYQGQSSDLP |
| 71 | nonspecific |
| 72 | MAAEGFTDVDCSVSKQCLPPCKAQFGIRAGAKCMNGKCKCYNGGSASSATRPFVCEYQGQSSDLP |
| 73 | MAAEGFTDVDCSVSKQCLPPCKAQFGIRAGAKCMNGKCKCYPHGSASSATRPFVCEYQGQSSDLP |
| 74 | MAAEGFTDVDCSVSKQCWPVCKKLFGTYRGKCMNGKCRCYSGSASSATRPFVCEYQGQSSDLP |
| 75 | nonspecific |
| 76 | MAAEGFTDVDCSVSKQCWSVCKDLFGVDRGKCMNGKCHCTPQGSASSATRPFVCEYQGQSSDLP |
| 77 | nonspecific |
| 78 | nonspecific |
| 79 | nonspecific |
| 80 | MAAEGFTDVDCSVSKQCWSVCKDLFGVDRGKCMNRKCKCFGRGSASSATRPFVCEYQGQSSDLP |
| 81 | MAAEGVPINVKCTGSPQCSKPCKELYGSSAGAKCMNGKCDCTPKGSASSATRPFVCEYQGQSSDLP |
| 82 | MAAEGVPINVKCTGSPQCLKPCKDLYGPHAGAKCMNGKCHCTPKGSASSATRPFVCEYQGQSSDLP |
| 83 | nonspecific |
| 84 | nonspecific |
| 85 | MAAEGVPINVKCTGSPQCIKPCKDAGMRFGKCMNGKCKCYNNGSASSATRPFVCEYQGQSSDLP |

FIG. 2 (Cont.)

| | |
|---|---|
| 86 | MAAEGVPINVKCTGSPQCLRPCKDRFGQHAGGKCMNGKCKCYPHGSASSATRPFVCEYQGQSSDLP |
| 87 | MAAEGVPINVKCTGSPQCSKPCKELYGSSAGAKCMNGKCDCTPKGSASSATRPFVCEYQGQSSDLP |
| 88 | MAAEGVPINVKCTGSPQCSKPCKELYGSSAGAKCMNGKCKCYPGSASSATRPFVCEYQGQSSDLP |
| 89 | MAAEGVPINVKCTGSPQCIKPCKDAGMREGKCMNGKCKCYPGSASSATRPFVCEYQGQSSDLP |
| 90 | nonspecific |
| 91 | nonspecific |
| 92 | MAAEGVPINVKCTGSPQCWPVCKQMFGKPNGKCMNRKCKCFGRGSASSATRPFVCEYQGQSSDLP |
| 93 | MAAEGVPINVKCTGSPQCLRPCKDRFGQHAGKKCMGKKCRCYQGSASSATRPFVCEYQGQSSDLP |
| 94 | MAAEGVPINVKCTGSPQCWPVCKQMFGKPNGKCMNGKCRCYSGSASSATRPFVCEYQGQSSDLP |
| 95 | nonspecific |
| 96 | MAAEGVPINVKCTGSPQCLPKCKEAIGKAAGKCMNGKCHCTPKGSASSATRPFVCEYQGQSSDLP |
| 97 | nonspecific |
| 98 | MAAEGVPINVKCTGSPQCWPVCKQMFGKPNGKCMNGKCHCTPQGSASSATRPFVCEYQGQSSDLP |
| 99 | MAAEGVPINVKCTGSPQCLLPCKEIYGIHAGAKCMNRKCKCFGRGSASSATRPFVCEYQGQSSDLP |
| 100 | MAAEGVPINVKCTGSPQCLPKCKEAIGKAAGKCMMSKCRCYSGSASSATRPFVCEYQGQSSDLP |
| 101 | MAAEGFTNVSCSASSQCWPVCKQMFGKPNGKCMNRKCHCTPKGSASSATRPFVCEYQGQSSDLP |
| 102 | MAAEGFTNVSCSASSQCLRPCKDRFGQHAGKKCMNGKCHCTPQGSASSATRPFVCEYQGQSSDLP |
| 103 | nonspecific |
| 104 | MAAEGFTNVSCSASSQCLRPCKDRFGQHAGKKCMNKKCRCYSGSASSATRPFVCEYQGQSSDLP |
| 105 | MAAEGFTNVSCSASSQCLRPCKDRFGQHAGKKCMGKKCRCYQGSASSATRPFVCEYQGQSSDLP |
| 106 | MAAEGFTNVSCSASSQCLPPCKAQFGQSAGAKCMNGKCHCTPKGSASSATRPFVCEYQGQSSDLP |
| 107 | MAAEGFTNVSCSASSQCLRPCKDRFGQHAGKKCMNGKCKCYGSASSATRPFVCEYQGQSSDLP |
| 108 | nonspecific |
| 109 | MAAEGFTNVSCSASSQCLPPCKAQFGQSAGAKCMNRKCKCFGRGSASSATRPFVCEYQGQSSDLP |
| 110 | nonspecific |
| 111 | nonspecific |
| 112 | MAAEGFTNVSCSASSQCYPHCKKETGYPNAKCMMSKCRCYSGSASSATRPFVCEYQGQSSDLP |
| 113 | nonspecific |
| 114 | nonspecific |
| 115 | nonspecific |
| 116 | MAAEGFTNVSCSASSQCWSVCQRLHNTSRGKCMMSKCRCYSGSASSATRPFVCEYQGQSSDLP |
| 117 | nonspecific |
| 118 | nonspecific |
| 119 | MAAEGFTNVSCSASSQCWSVCKDLFGVDRGKCMNGKCHCTPQGSASSATRPFVCEYQGQSSDLP |
| 120 | nonspecific |

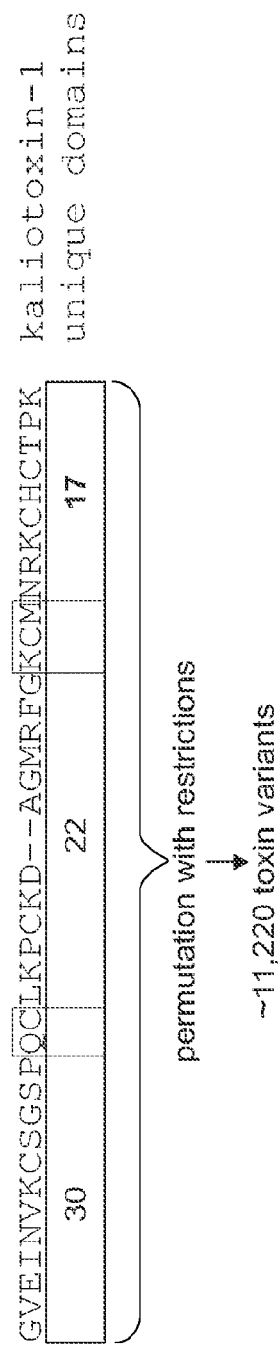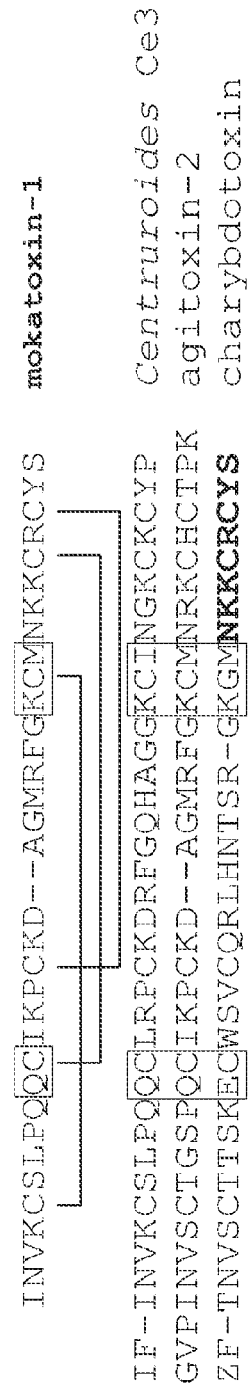

mokatoxin-1
INVKCSLPQQCIKPCKDAGMRFGKCMNKKCRCYS kaliotoxin-1
GVEINVKCSGSPQCLKPCKDAGMRFGKCMNRKCHCTPK inactive kaliotoxin-1
GVEINVKCSGSPQCLKPCKDAGMDFGDCMNDKCHCTPK mokatoxin_422
TVIDVKCTSPKQCLPPCKAQFGIRAGAKCMNKKCRCYS mokatoxin_0516
TVINVKCTSPKQCLRPCKDRFGQHAGGKCMNGKCKCYPH

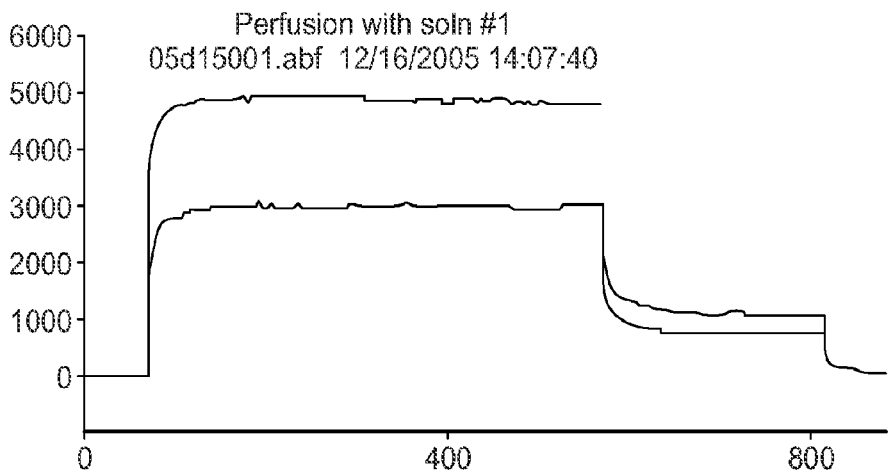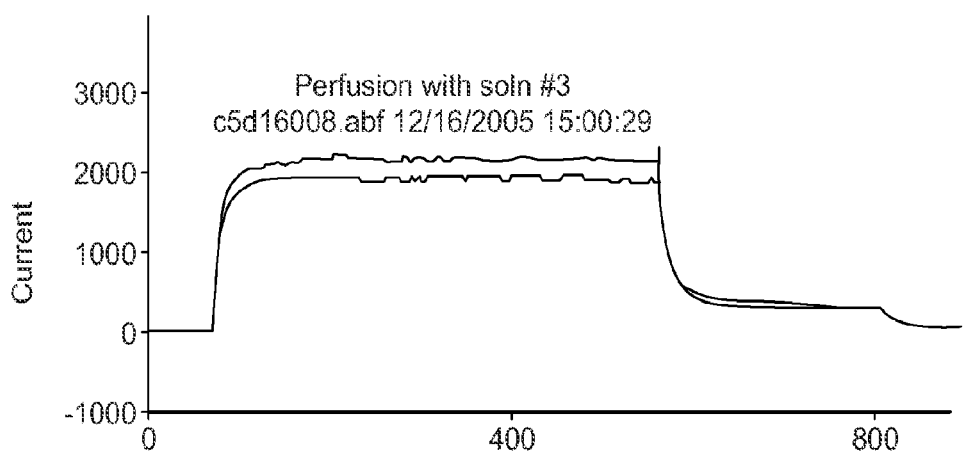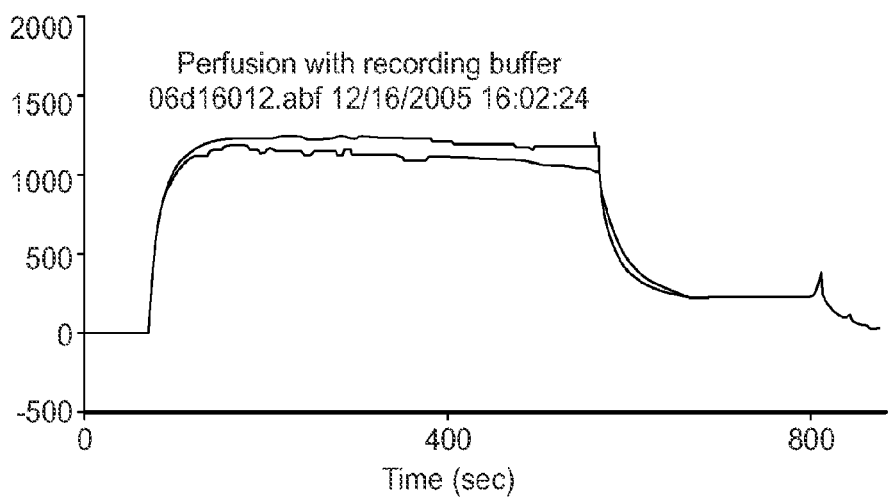
FIG. 12

| Toxin | Structural data | Fold | Main target |
|---|---|---|---|
| Huwentoxin-IV (35-mer) *Selenocosmia huwena* | ECLEIFKACNPSNDQCCKSSKLVCSRKTRWCKYQI* | ββ (ICK) | Na$_v$ |
| ACTX Hi OB4219 (38-mer) *Hadronyche infesa* | KCLAEAADCSPWSGDSCCKPYLCSCIFFYPCSCRPKGW | βββ (ICK) | Na$_v$? |
| ATX Ia (46-mer) *Anemonia sulcata* | GAACLCKSDGPNTRGNSMSGTIWVFGCPSGWNNCEGRAIIGYCCKQ | ββββ | Na$_v$ |
| B-IV (55-mer) *Cerebratulus lacteus* | ASATWGAAVQACENNCRKKYDLCIRCQGKWAGKRGKCAAHCIIQRNNCKGKCKKE | αα (α helical hairpin) | Na$_v$? |
| δ-Atracotoxin-Hv1 (42-mer) *Hadronyche versuta* | CAKKRNWCGKTEDCCCPMKCVYAWYNEQGSCQSTISALWKKC | βββ3$_{10}$ Helical ended (ICK) | Na$_v$ |
| AahII (64-mer) *Androctomus australis* | VKDGYIVDDVNCTYFCGRNAYCNEECTKLKGESGYCQWASPYGNACYCYKLPDHVRTKGPGRCH* | βαββ | Na$_v$ |
| Crotamine (42-mer) *Crotalus durissus* | YKQCHKKGGHCFPKEKICLPSSDFGKMDCRWRWKCCKKGSG | αβββ | Na$_v$ |
| Bj-xtrIT (76-mer) *Buthotus judaicus* | KKNGYPLDRNGKTTECSGVNAIAPHYCNSECTKVYYAESGYCCWGACYCFGLEDDKPIGPMK<br>DITKKYCDVQIIPS | βαβαββα | Na$_v$ (insect) |

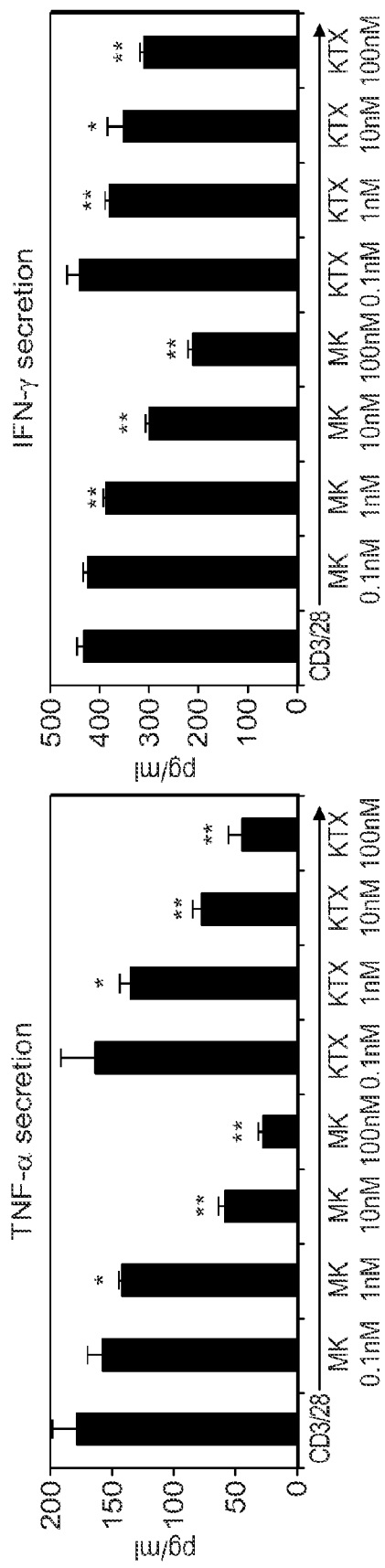
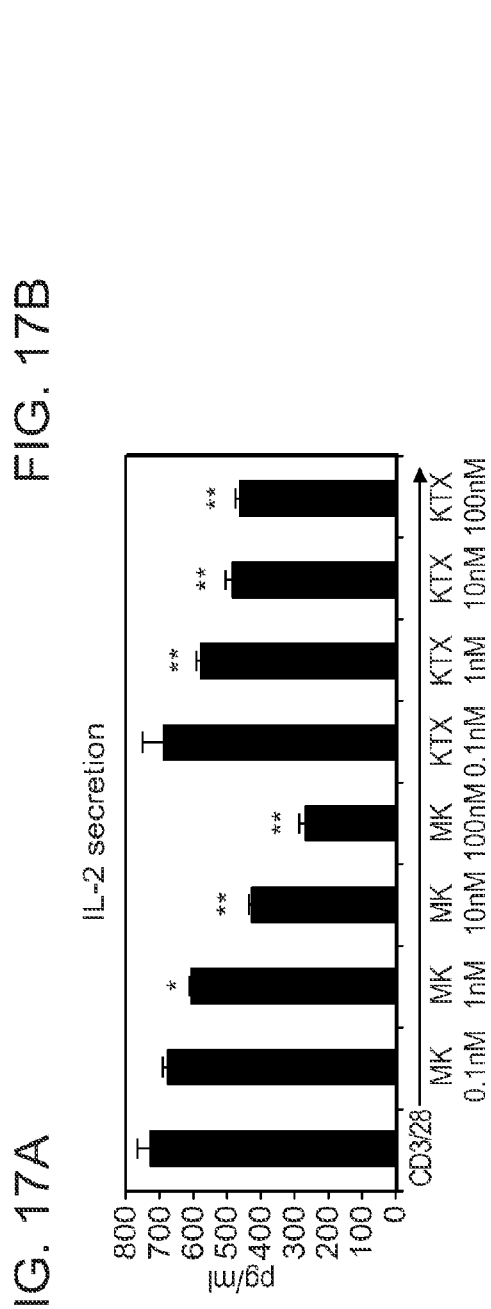
FIG. 17A
FIG. 17B
FIG. 17C

IDENTIFICATION OF TOXIN LIGANDS

ACKNOWLEDGEMENT OF FEDERAL RESEARCH SUPPORT

Work for this invention was partially funded by a grant under GM54237 awarded by the National Institute of Health. The government may have certain rights in this invention.

REFERENCE TO RELATED APPLICATIONS

This application is a national phase application of International Application No. PCT/US08/13385 (PCT Pub. No. WO/2009/075773), filed Dec. 5, 2008, which claims priority to U.S. Provisional Application No. 61/012,209, filed Dec. 7, 2007 and U.S. Provisional Application No. 61/074,794, filed Jun. 23, 2008, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 31, 2013, is named 28940004.txt and is 138 KB in size.

SEQUENCE LISTING

In accordance with 37 CFR 1.52(e)(5), a Sequence Listing in the form of a text file (entitled "SequenceListing.txt," created on Sep. 15, 2010, and 134 kilobytes in size) is incorporated herein by reference in its entirety.

BACKGROUND

Transmembrane proteins are key components of essential cellular functions. One particular class of transmembrane proteins, ion channels, are commonly characterized by the method utilized to open or close the channel protein, either permitting or preventing specific ions from permeating the channel protein and crossing the cellular membrane. For example, one type of channel protein is the voltage-gated channel protein, which is opened or closed in response to changes in electrical potential across the cell membrane. Another type of channel protein is mechanically gated, such that mechanical stress on the protein opens or closes the channel. Still another type is ligand-gated, such that it opens or closes depending on whether a particular ligand is bound the protein. The ligand can be either an extracellular moiety, such as a neurotransmitter, or an intracellular moiety, such as an ion or nucleotide.

Transmembrane proteins such as ion channels are involved in a wide variety of biological process, such as cardiac, skeletal, and smooth muscle contraction, nerve function, epithelial transport of nutrients and ions, T-cell activation and pancreatic beta-cell insulin release. For example, one common type of channel proteins, $K^+$ ion channels, control heart rate, regulate the secretion of hormones such as insulin into the blood stream, generate electrical impulses central to information transfer in the nervous system, and control airway and vascular smooth muscle tone. Thus, $K^+$ ion channels participate in cellular control processes that are abnormal, such as cardiac arrhythmia, diabetes mellitus, seizure disorder, asthma and hypertension. In the search for new drugs, diagnostics, or research tools, transmembrane proteins are therefore a common target.

SUMMARY

In one aspect, the present disclosure provides systems and methods for identifying or detecting a ligand in a sample. Such systems and methods include contacting at least one receptor with a sample comprising at least one toxin peptide; and determining whether a toxin peptide in the sample selectively binds to the at least one receptor, thereby identifying or detecting a ligand in a sample.

In some embodiments, the at least one receptor is expressed in cells, and the method includes transfecting the cells with a nucleic acid encoding the at least one receptor. The at least one receptor can include a receptor that is heterologous to the cell in which it is expressed. The at least one receptor can include a receptor that is native to the cell in which it is expressed. The at least one receptor can include a receptor that is stably expressed in a cell.

In some embodiments, transfected cells include at least two cells comprising a first cell expressing a first receptor and a second cell expressing a second receptor different from the first receptor. In some embodiments, the at least one receptor is immobilized on a substrate.

The at least one receptor can include a transmembrane protein, e.g., a channel protein, e.g., a channel protein selected from the group consisting of a sodium ion channel, a potassium ion channel, a calcium ion channel, a chloride ion channel, a non-specific ion channel. In some embodiments, a transmembrane protein includes a potassium ion channel. In some embodiments, a potassium ion channel is a Kv1.3 channel.

In some embodiments, a sample includes a library of toxin peptides, e.g., a phage display library. In some embodiments, toxin peptides are about 5-200 amino acids in length. In some embodiments, toxin peptides are about 5-100 amino acids in length. In some embodiments, toxin peptides are about 5-50 amino acids in length. In some embodiments, toxin peptides are about 20-50 amino acids in length. In some embodiments, toxin peptides are about 30-50 amino acids in length. Toxin peptides can include sequences found in a toxin that is naturally expressed in an organism (e.g., a snake toxin, a snail toxin, a scorpion toxin, a sea anemone toxin, a spider toxin, a lizard toxin). In some embodiments, a toxin peptide includes six cysteine residues. In some embodiments, spacing of the cysteine residues is conserved with the spacing of cysteine residues found in a natural toxin. In some embodiments, a disulfide bonding pattern is conserved with a disulfide bonding pattern found in a natural toxin. For example, in some embodiments, a toxin peptide includes at least 35 amino acids, and has an amino acid sequence including at least six cysteine residues, so that the cysteine residues are located at each of the following positions within the 35 amino acids: 7 or 8, 13 or 14, 27 or 28, 32 or, 33, and 34 or 35. In some embodiments, a toxin peptide library includes toxin peptides in which a disulfide bonding pattern is conserved with a disulfide bonding pattern found in a natural toxin, and in which residues other than cysteines are altered (e.g., by randomization of residues at at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 positions of a toxin sequence).

In some embodiments, toxin peptides have an amino acid sequence that allow variability at "X" residues, e.g., toxin peptides have an amino acid sequence that includes: $(X)_mC(X)_mC(X)_mC(X)_oC(X)_nCXC(X)_m$ (SEQ ID NO: 4), wherein X is any amino acid, and wherein m=0-10 amino acids, n=2-

10 amino acids, and o=2-20 amino acids. In some embodiments, m is 2. In some embodiments, m is 4. In some embodiments, m is 5. In some embodiments, m is 6. In some embodiments, n is 3. In some embodiments, n is 4. In some embodiments, o is 9. In some embodiments, o is 10. In some embodiments, o is 11.

In some embodiments, toxin peptides have an amino acid sequence that includes: $(X)_mKC(X)_nQC(X)_nCK(X)_oKCM(X)_nCXC(X)_m$ (SEQ ID NO: 5), wherein X is any amino acid, and wherein m=0-10 amino acids, n=2-10 amino acids, and o=2-20 amino acids. In some embodiments, toxin peptides have an amino acid sequence that includes: XXXKCXXXXQCXXXCKXXXKCMXXXCXCXX (SEQ ID NO: 6), wherein X is any amino acid.

A toxin peptide library can include a plurality of unique toxin peptides, e.g., at least $10^1$, $10^2$, $10^3$, $10^4$, $10^5$, $10^6$, $10^7$, $10^8$, $10^9$, $10^{10}$, $10^{11}$, $10^{12}$, or more unique toxin peptides.

The present disclosure also provides libraries of toxin peptides. In some embodiments, a library of toxin peptides includes a plurality of members having an amino acid sequence that includes: $(X)_mC(X)_nC(X)_nC(X)_oC(X)_nCXC(X)_m$ (SEQ ID NO: 4), wherein X is any amino acid, and wherein m=0-10 amino acids, n=2-10 amino acids, and o=2-20 amino acids. In some embodiments, m=2-10 amino acids, n=3-5 amino acids, and o=7-12 amino acids. In some embodiments, m is 2. In some embodiments, m is 4. In some embodiments, m is 5. In some embodiments, m is 6. In some embodiments, n is 3. In some embodiments, n is 4. In some embodiments, o is 9. In some embodiments, o is 10. In some embodiments, o is 11.

In some embodiments, a library of toxin peptides includes a plurality of members having an amino acid sequence that includes: $(X)_mKC(X)_nQC(X)_nCK(X)_oKCM(X)_nCXC(X)_m$ (SEQ ID NO: 5), wherein X is any amino acid, and wherein m=0-10 amino acids, n=2-10 amino acids, and o=2-20 amino acids. In some embodiments, m=2-10 amino acids, n=3-4 amino acids, and o=7-12 amino acids. In some embodiments, a library of toxin peptides includes a plurality of members having an amino acid sequence that includes: XXXKCXXXXQCXXXCKXXXXXXKCMXXXCXCXX (SEQ ID NO: 6), wherein X is any amino acid.

In some embodiments, a library of toxin peptides includes toxin peptides from one or more of a snake toxin, a snail toxin a scorpion toxin, a sea anemone toxin, and a lizard toxin.

The present disclosure also provides mokatoxin-1, mokatoxin-2, and mokatoxin-3 peptides, and variants thereof (e.g., variants that specifically bind to, and inhibit, a Kv1.3 channel). In some embodiments, the disclosure provides a peptide comprising an amino acid sequence that is at least 95% identical to SEQ ID NO: 1. In some embodiments, the disclosure provides a peptide comprising an amino acid sequence that is at least 95% identical to SEQ ID NO: 2. In some embodiments, the disclosure provides a peptide comprising an amino acid sequence that is at least 95% identical to SEQ ID NO: 3. Pharmaceutical compositions including the peptides and methods of using the compositions, e.g., for immune suppression, are also provided herein.

In another aspect, the present disclosure provides a peptide comprising the following amino acid sequence: IXVKCXXPXQCXXPCKXXXGXXXXXKCMNXKCXCYX$_n$ (SEQ ID NO: 7), wherein X is any amino acid, wherein n=1-20 amino acids, and wherein the peptide specifically binds to a potassium channel.

In still another aspect, the present disclosure provides a peptide comprising the following amino acid sequence: IXVKCXXPXQCXXPCKXXGXXXXKCM-NXKCXCYX$_n$ (SEQ ID NO: 8), wherein X is any amino acid, wherein n=1-20 amino acids, and wherein the peptide specifically binds to a potassium channel.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWING

Provided methods and systems may be better understood with reference to the following drawings and description. Components in the figures are not necessarily to scale, emphasis instead being placed upon illustrating principles of the disclosure. In the figures, like referenced numerals designate corresponding parts throughout the different views.

FIG. 1 is a schematic representation of the partial amino acid sequence of a ligand construct including animal venom neurotoxin kaliotoxin-1 (KTX) in a phage display suitable vector (SEQ ID NO: 132).

FIG. 2 is a schematic representation of the partial amino acid sequences of an animal toxin library (SEQ ID NOS 133-202, respectively, in order of appearance).

FIG. 4 is a set of graphs depicting the specific binding of different animal venom toxin phages to their respective targets quantified by ELISA.

FIG. 8 is a schematic representation of one type of representative design of a combinatorial toxin library based on KTX and similar toxins. FIG. 8A discloses SEQ ID NO: 11. FIG. 8B discloses SEQ ID NOS 1, 33, 27 and 231, respectively, in order of appearance.

FIG. 12 is a set of graphs depicting pharmacologically active *Dendroaspis* dendrotoxin blocking Kv1.1 K$^+$ channels in mammalian cells when expressed on the phage. Camel VHH, a nonspecific-phage, and phage buffer cause no block.

FIG. 15 is a table showing the amino acid sequences of various toxin peptides (SEQ ID NOS 214-221, respectively, in order of appearance). Animal species, peptide length, receptor target, and positions of disulfide bonds are also indicated.

FIG. 16 is a graph which shows the dose-response relationship of mokatoxin-1 on different K channels: human (h) Kv1.1, Kv1.2, Kv1.3, and mouse (m) big conductance calcium-activated K channel.

FIG. 17 (A-C) is a set of graphs showing that treatment with MK toxin inhibits the secretion of effector cytokines by T cells. $10^5$ purified T cells were treated with MK and KTX toxin 1 h prior activation and stimulated for 16 h with CD3/CD28 beads at a 1:1 ratio. The supernatant were assessed for IL-2 (C), TNF-α (A) and IFN-γ (B) secretion by ELISA. The graphs show the results of a representative experiment from 2 independents assays. *, $p<0.05$; **, $p<0.01$.

DETAILED DESCRIPTION OF CERTAIN EMBODIMENTS

Figure 3:
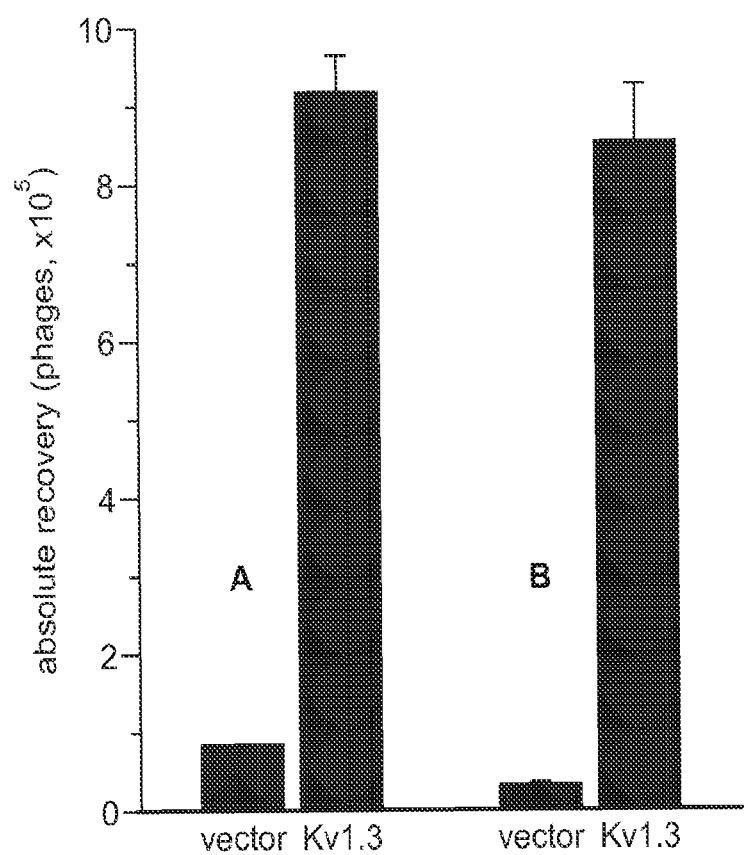
FIG. 3 is a graph depicting the specific enrichment of KTX by Kv1.3 transfected cells.

The present disclosure provides for systems for identifying, characterizing, and detecting ligands that bind to particular receptors (also referred to herein as targets), compositions including the ligands, and methods of using the ligands. Methods of identifying ligands described herein permit selection of ligands that exhibit a desired degree of specificity, affinity, and/or biological activity for a target of interest. The present disclosure encompasses the discovery of novel ligands (e.g., ligands identified from variegated libraries of toxin peptides) having a high degree of selectivity for specific receptors such as ion channels, as well as methods for producing and using the ligands to modulate receptor activity. Exemplary ligands described herein include mokatoxin-1, mokatoxin-2, and mokatoxin-3, each of which specifically bind to the receptor Kv1.3. Other ligands and receptors are also described.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present disclosure. All publications, patent applications, patents, references to amino acid and nucleic acid sequence database identifiers, and other references mentioned herein are incorporated by reference in their entirety. The materials, methods, and examples disclosed herein are illustrative only and not intended to be limiting.

DEFINITIONS

As used herein, the term "characteristic sequence element" or "sequence element" refers to a stretch of contiguous amino acids, typically 5 amino acids, e.g., at least 5-500, 5-250, 5-100, 5-75, 5-50, 5-25, 5-15, or 5-10 amino acids, that shows at least about 80%, 85%, 90%, 95%, 96%, 97%, 98%, 99%, or 100% identity with another polypeptide. In some embodiments, a characteristic sequence element participates in or confers function on a polypeptide.

As used herein, the term "corresponding to" is often used to designate the position/identity of an amino acid residue in a polypeptide (e.g., in a toxin). Those of ordinary skill will appreciate that, for purposes of simplicity, a canonical numbering system (based on wild type toxins) is utilized herein (as illustrated, for example, in FIGS. 2, 9, 14, and 15), so that an amino acid "corresponding to" a residue at position 7, for example, need not actually be the 7$^{th}$ amino acid in a particular amino acid chain but rather corresponds to the residue found at 7 in a wild type polypeptide (e.g., in a toxin); those of ordinary skill in the art readily appreciate how to identify corresponding amino acids.

The term "library" refers to a collection of members. A library may be comprised of any type of members. For example, in some embodiments, a library comprises a collection of phage particles. In some embodiments, a library comprises a collection of peptides. In some embodiments, a library comprises a collection of cells. A library typically includes diverse members (i.e., members of a library differ from each other by virtue of variability in an element, such as a peptide sequence, between members). For example, a library of phage particles can include phage particles that express unique peptides. A library of peptides can include peptides having diverse sequences. A library can include, for example, at least $10^1$, $10^2$, $10^3$, $10^4$, $10^5$, $10^6$, $10^7$, $10^8$, $10^9$, or more unique members.

The term "ligand" refers to any agent that binds to a receptor. Ligands can include, but are not limited to, small molecules (whether synthetic or isolated from natural sources), biodegradable cofactors, proteins, synthetic peptides, and polymers, both synthetic and naturally occurring, including DNA. In many embodiments, ligands are polypeptides. For example, ligands can be protein/peptide toxins and/or other venom/poison components of animal, plant, or microbial origin or natural or synthetic derivatives of the same. In some embodiments, a ligand is a toxin peptide as defined herein. In some embodiments, ligands are expressed and/or presented to a receptor as part of a library, e.g., a phage display library. In some embodiments, ligands are expressed and/or presented singly. A ligand can be presented to a receptor in any other mean or form (e.g., removed from the phage, or expressed in a comparable/other expression systems) suitable for ligand-target selection and/or ligand validation. In some embodiments, a ligand is a phage-only peptide to monitor or alter a selection process. According to methods described herein, ligands can be selected on any of a variety of bases, including for example on the basis of a particular affinity, specificity, or activity toward a receptor of interest. In certain embodiments, a ligand binds to a receptor with a K$_D$ of $1\times10^{-6}$ M or less, $1\times10^{-7}$ M or less, $1\times10^{-8}$ M or less, $1\times10^{-9}$ M or less, $1\times10^{-10}$ M or less, $1\times10^{-11}$ M or less, or $1\times10^{-12}$ M or less. In certain embodiments, a ligand binds a receptor which is a channel, and inhibits an activity of the channel (e.g., ion transport) with an IC$_{50}$ of $1\times10^{-6}$ M or less, $1\times10^{-7}$ M or less, $1\times10^{-8}$ M or less, $1\times10^{-9}$ M or less, $1\times10^{-10}$ M or less, $1\times10^{-11}$ M or less, or $1\times10^{-12}$ M or less. In some embodiments, a ligand has specificity a particular receptor such that the ligand binds to the receptor and/or modulates an activity of the receptor with an affinity/potency that is at least twice, 4 times, 5 times, 10 times, 100 times, 1000 times as great as for another receptor in the same class. To give one example, in some embodiments, a ligand binds to one type of potassium channel, Kv1.3, with an affinity that is at least 10 or 100 times greater than its affinity for another potassium channel (e.g., Kv1.1 or Kv1.2).

The term "receptor" (also referred to herein as a "target") refers to a molecule, part of a molecule, chimera of more than one molecule or parts of it, or an assembly of molecules that serves as an interacting partner for a ligand. In some embodiments, a receptor is a receptor for a toxin peptide. In some embodiments, a receptor is a channel polypeptide. For example, receptors for toxin peptides include, but are not limited to, $Ca^{2+}$ channel, $Na^+$ channels, $K^+$ channels, NMDA receptor, alpha1-adrenoceptor, neurotensin receptor, $Cl^-$ channel, noradrenaline transporter, vasopressin receptor, acetylcholinesterase, endothelin receptor, natriuretic peptide receptor, GPIIb/IIIa integrin receptor, muscle-type nicotinic acetylcholine receptor (nAChR), neuronal-type nAChR, muscarinic acetylcholine (ACh) receptor, serotonin (5-HT) receptor, angiotensin-converting enzyme. Antibodies and other specific molecular partners for toxin peptides are also defined as receptors. Receptors may be wild-type receptors or natural or synthetic variants of wild-type receptors. "Receptor" further refers to all protein families (types or superfamilies) that include at least one member (also known as subtype or isoform) that are receptors for toxin peptides. For example, a receptor subtype Kv2.1 $K^+$ channel has no known toxin peptide ligand, but at least one other member of the $K^+$ channel protein family (for example subtype Kv1.3) has a toxin ligand and therefore, members of the $K^+$ channel family in its entirety are considered "receptors."

A "scaffold" is a structural element, or set of elements, that is common to a set of structurally related compounds. For example, a toxin peptide scaffold may include one or more particular amino acids located at particular positions along the polypeptide chain of a toxin. In some embodiments, a toxin peptide scaffold may include a specific number and arrangement of disulfide bridges. A scaffold can include a sequence having 50% or higher sequence identity with the toxin, or less that 50% identity if residues required for interaction with a receptor are the same or similar. In some embodiments, two toxins are said to share a scaffold if the toxins include a similar number of amino acid residues and cysteine residues found within the sequences having similar spacing. Alternatively or additionally, a toxin peptide scaffold may include one or more amino acids found at particular positions within a sequence element (typically at least 5-20 amino acids long) found in a toxin. In some embodiments, at least 50% of the amino acid residues in a given sequence element are scaffold amino acids. In some embodiments, at least 55%, 60%, 65%, 70%, 75%, 80%, 85%, 90%, 95%, 96%, 97%, 98%, 99% or more of the amino acids in a sequence element are scaffold amino acids.

The term "substantial identity" of amino acid sequences (and of polypeptides having these amino acid sequences) typically means sequence identity of at least 40% compared to a reference sequence as determined by comparative techniques known in the art. For example, a variety of computer software programs are well known for particular sequence comparisons. In some embodiments, the BLAST is utilized, using standard parameters, as described. In some embodiments, the preferred percent identity of amino acids can be any integer from 40% to 100%. In some embodiments, sequences are substantially identical if they show at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identical residues in corresponding positions. In some embodiments, polypeptides are considered to be "substantially identical" when they share amino acid sequences as noted above except that residue positions which are not identical differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

As mentioned above, one example of an algorithm that is suitable for determining percent sequence identity and sequence similarity is the BLAST algorithm, which is described in Altschul et al., 1977, Nuc. Acids Res. 25:3389-3402. BLAST is used, with the parameters described herein, to determine percent sequence identity for the nucleic acids and proteins of the present disclosure. Software for performing BLAST analysis is publicly available through the National Center for Biotechnology Information (available at the following internet address: ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA, 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin &

Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "toxin" refers to all peptides and/or proteins, of any amino acid length and sequence, in either monomeric or multimeric forms naturally, present in animal venoms or poisons and their non-venom homologues. Animal toxins include all molecules identified or inferred by any means (e.g., physical, chemical, biochemical, genetic, genomic, proteomic) from animal venoms or poisons, including but not limited to isolation from crude venoms, isolation from venom gland tissues or extracts, identification based on venom gland proteome/proteomics, venome/venomics, transcriptome, and/or EST analysis. In some embodiments, a toxin is a toxin from a venom or poison of a snake, snail, scorpion, sea anemone, lizard, or a spider. Representative toxins, and their amino acid sequences and source designations, are presented in Tables and Figures herein (e.g., Table 1, Table 2, Table 13, Example 20, FIG. 8, FIG. 9, FIG. 14, FIG. 15).

The term "toxin peptide", as used herein, refers to polypeptides that have structural and/or functional similarity to one or more toxins (and includes such toxins). In some embodiments, a toxin peptide has an amino acid sequence that is substantially identical to that of a toxin. In some embodiments, a toxin peptide is less than 100, 90, 80, 70, 60, 50, 40, 30, 20 or fewer amino acids long. In some embodiments, a toxin peptide is more than 5, 6, 7, 8, 9, 10, 11, 12, 13, 14, 15, 16, 17, 18, 19, 20, 21, 22, 23, 24, 25, 26, 27, 28, 29, 30, or more amino acids long. In some embodiments, a toxin peptide is between about 20 and about 60 amino acids long. In some embodiments, a toxin peptide is between about 30 and about 50 amino acids long. In some embodiments, a toxin peptide has an amino acid sequence that includes a plurality of cysteines. In some embodiments, such cysteines are located at positions corresponding to positions 7 or 8, 13 or 14, 27 or 28, 32 or 33, and/or 34 or 35 of a toxin. In some embodiments, toxin peptides have an amino acid sequence that includes the following sequence: $(X)_m C(X)_n C(X)_n C(X)_o C(X)_n CXC(X)_m$ (SEQ ID NO: 222), wherein X is any amino acid, and wherein m=2-10 amino acids, n=3-5 amino acids, and o=7-12 amino acids. In some embodiments, toxin peptides have an amino acid sequence that includes: $(X)_m KC(X)_n QC(X)_n CK(X)_o KCM(X)_n CXC(X)_m$ (SEQ ID NO: 223), wherein X is any amino acid, and wherein m=2-10 amino acids, n=3-4 amino acids, and o=7-12 amino acids. In some embodiments, toxin peptides have an amino acid sequence that includes: XXXKCXXXXQCXXXCKXXXXXXXKC-MXXXCXCXX (SEQ ID NO: 6), wherein X is any amino acid. In some embodiments, a toxin peptide has an amino acid sequence that includes a plurality of sequence elements, each of which is found in a natural toxin. In some embodiments, a toxin peptide has an amino acid sequence that includes a plurality of sequence elements that are found in (or share substantially identity with sequence elements that are found in) a plurality of different natural toxins. In some embodiments, a toxin peptide has an amino acid sequence that includes at least two sequence elements that are found in (or share substantially identity with sequence elements that are found in) the same natural toxin, but further includes one or more sequence elements that are not found in the natural toxin.

The term "transmembrane protein" refers to polypeptides that partially span a membrane and that completely span a membrane. A "transmembrane protein" refers to monomeric as well as multimeric proteins, including heteromultimeric proteins. A transmembrane protein can be a protein found on any membrane of a cell (e.g., a membrane of an intracellular compartment such as the endoplasmic reticulum, Golgi apparatus, an endocytic compartment, nuclear membrane, or a cell surface membrane).

The term "wild-type", when applied to a polypeptide (e.g., a receptor polypeptide, or a toxin polypeptide) refers to a polypeptide whose primary amino acid sequence is identical to that of a polypeptide found in nature. As will be appreciated by those skilled in the art, a wild type polypeptide is one whose amino acid sequence is found in normal (i.e., non-mutant) polypeptides.

Receptors

Methods described herein are applicable to any receptor, i.e., any receptor that can serve as an interacting partner for a ligand. In most embodiments, a receptor suitable for methods described herein is a receptor that serves as an interacting partner for a toxin peptide. In some embodiments, a receptor is a transmembrane protein. In some embodiments, a receptor is a channel protein. Exemplary receptors for toxin peptides may include, but are not limited to, ion channels (e.g., potassium, sodium, calcium, chloride, and non-specific ion channels), as well as other transmembrane proteins that are sensitive to toxin peptides, for example, neurotransmitter receptors (e.g., NMDA receptor, serotonin (5-HT) receptor, alpha1-adrenoceptor, muscle-type nicotinic acetylcholine receptor (nAChR), neuronal-type nAChR, muscarinic acetylcholine (ACh) receptor), receptors for endogenous peptides (e.g., neurotensin receptor, endothelin receptor, natriuretic peptide receptor, vasopressin receptor), noradrenaline transporter, acetylcholinesterase, GPIIb/IIIa integrin receptor, angiotensin-converting enzyme, and G-protein coupled receptors that are and are not ion channels. Receptors also include amino acid transporters and integrin receptors (e.g., glycoprotein IIb/IIIa integrin receptors). Table 1 below provides a non-exclusive list of receptors, as well as exemplary toxin ligands for the receptors, and organisms in which the ligands are naturally expressed. Receptors that may be utilized in accordance with the present invention include wild type receptors and also receptor polypeptides whose amino acid sequences are substantially identical to wild type polypeptides. Furthermore, as will be appreciated by those skilled in the art, receptor polypeptides with various sequence modifications (e.g., fusions, substitutions, deletions, additions, rearrangements) as compared with a wild type receptor may be utilized if desired.

TABLE 1

| Organism | Ligand (scaffold) name | Representative receptor (target) |
|---|---|---|
| marine snail | *Conus geographus* GIIIA | Na$^+$ channel |

TABLE 1-continued

| Organism | Ligand (scaffold) name | Representative receptor (target) |
|---|---|---|
| sea anemone | *Stichodactyla helianthus* Shk toxin | K$^+$ channel (e.g., Kv1.1) |
| scorpion | kaliotoxin | K$^+$ channel (e.g., Kv1.3) |
| scorpion | hongotoxin-1 | K$^+$ channel (e.g., Kv1.1) |
| scorpion | *Odontobuthus doriae* OD 1 toxin | Na$^+$ channel |
| spider | *Grammostola spatulata* voltage sensor toxin (VSTX-1) | K$^+$ channel (e.g., KvAP, KvAP VSD) |
| spider | *Thrixopelma pruriens* Protoxin-1 | Na$^+$ channel |
| snake | three-finger toxins | acetylcholine receptor |
| snake | *Dendroaspis* natriuretic peptide | natriuretic peptide receptor A |
| snake | sarafotoxin | endothelin receptor (e.g., endothelin receptor B) |
| snake | dendrotoxin | K$^+$ channel (e.g., Kv1.1), Ca$^+$ channel |
| snake | ADAM disintegrin/metalloproteinase | integrins/extracellular matrix |
| snake | cobra venom factor | complement system |
| snake | CNP-BPP | |
| snake | CRISP | |
| snake | crotamine | |
| snake | cystatin | |
| snake | factor V | |
| snake | factor X | |
| snake | Fasciculin-2 | Acetylcholinesterase |
| snake | kallikrein | |
| snake | L-amino acid oxidase | |
| snake | mamba intestinal toxin | |
| snake | nerve growth factor | |
| snake | phospholipase A2 type IB | Phospholipids |
| snake | phospholipase A2 type IIA | Phospholipids |
| snake | SPRY SPla/ryanodine | |
| snake | VEGF | |
| snake | waglerin | acetylcholine receptor |
| snake | waprin | |
| marine snail | κ-conotoxins PVIIA | K$^+$ channel |
| marine snail | κA-conotoxins SVIA | K$^+$ channel |
| marine snail | κM-conotoxins RIIIK | K$^+$ channel |
| marine snail | μ-conotoxin PIIIA | Na$^+$ channel |
| marine snail | μO-Conotoxin MrVIB | Na$^+$ channel |
| marine snail | δ-conotoxin TxVIA | Na$^+$ channel |
| marine snail | ziconotide/conotoxins | N Ca$^{2+}$ channel |
| marine snail | ω-conotoxin CVID | N Ca$^{2+}$ channel |
| marine snail | ω-conotoxin NVIID | N Ca$^{2+}$ channel |
| marine snail | ω-conotoxin MVIIC | P/Q Ca$^{2+}$ channels |
| marine snail | α-conotoxin GI | muscle nAChR |
| marine snail | αA-conotoxin PIVA | muscle nAChR |
| marine snail | ψ-conotoxin PIIIE | muscle nAChR |
| marine snail | α-conotoxin Vc1.1 | neuronal nAChR |
| marine snail | Conantokin-G | NMDA receptor |
| marine snail | Contulakin-G | neurotensin receptor |
| sea anemone | Sea anemone Type 1 ShK | K$^+$ channel |
| sea anemone | Sea anemone Type 2 | K$^+$ channel |
| sea anemone | Sea anemone Type 3 | K$^+$ channel |
| sea anemone | 1 Sea anemone Type 1 ApB ApB | Na$^+$ channel |
| sea anemone | Sea anemone Type 2 | Na$^+$ channel |
| sea anemone | Sea anemone Type 1 + 2 | Na$^+$ channel |

TABLE 1-continued

| Organism | Ligand (scaffold) name | Representative receptor (target) |
|---|---|---|
| sea anemone | Sea anemone Type 3 | Na⁺ channel |
| sea anemone | Sea anemone Type Others Calitoxin I | Na⁺ channel |
| sea anemone | APETx2 | ASIC channels |
| venomous lizards | Helokinestatin | bradykinin B2 receptor |
| venomous lizards | exendin-4 | glucagon-like peptide 1 receptor |

According to methods of the present disclosure, a single ligand or multiple ligands may be identified for one or more receptors. In some embodiments, receptors are expressed in cells. In some embodiments, receptors are immobilized (e.g., immobilized on a solid support or in an artificial membrane). In some embodiments, receptors are purified.

In some embodiments, a receptor is a potassium channel. Potassium channels are mainly found in plasma membranes but are not generally distributed over the cell surface. Potassium channels catalyze the rapid permeation of potassium ions while rejecting biologically abundant potential competitors such as sodium, calcium and magnesium. Ion selectivity and high through put rate of potassium channels is accomplished by precise co-ordination of dehydrated potassium by the protein and multiple ion occupancy within the permeation pathway.

All potassium channels carry out the formation of a transmembrane "leak" specific for potassium ions. Since cells almost universally maintain cytoplasmic potassium concentrations higher than those extracellularly, the opening of a potassium channel implies a negative ongoing change in electrical voltage across the cell membrane. This may result in termination of the action potential of electrically excitable cells including nerve, muscle and pancreatic beta cells. In non-excitable cells, potassium channels play important roles in the cellular potassium recycling required for electrolyte balance affected by the renal epithelium.

In some embodiments, a receptor is a voltage gated potassium channel belonging to the delayed rectifier class or Shaker potassium channel subfamily, which includes Kv1.1, Kv1.2, Kv1.3, Kv1.4, Kv1.5, Kv1.6, Kv1.7, and Kv1.8. In some embodiments, a receptor is a potassium receptor of the Kv2, Kv3, Kv4, Kv5, Kv6, Kv7, Kv9, Kv9, Kv10, Kv11, or Kv12 family (see an exemplary list of such receptors in Gutman et al., Pharmacol. Rev. 57(4): 473-508, 2005).

In some embodiments, a receptor is a Kv1.3 potassium channel. Kv1.3 potassium channels are a voltage-gated receptors expressed in a number of tissues, including T lymphocytes. One exemplary a ligand for Kv1.3 channel is kaliotoxin (KTX). KTX, found naturally in the venom of at least one species of scorpions, is a peptidyl inhibitor of Ca(2+)-activated K⁺ channels and voltage-gated K⁺ channels Kv1.1, Kv1.2, Kv1.3. KTX is a single, approximately 4-kDa, polypeptide chain. KTX displays sequence homology with other scorpion-derived inhibitors of Ca(2+)-activated or voltage-gated K⁺ channels: 44% homology with charybdotoxin (CTX), 52% with noxiustoxin (NTX), and 44% with iberiotoxin (IbTX).

In certain embodiments, a receptor is a voltage-gated sodium channel. Sodium channels have important functions throughout the body. For example, Nav1.4 controls excitability of skeletal muscle. Nav1.5 controls excitability of cardiac myocytes. Nav1.1, Nav1.2, and Nav1.6 are abundant in the central nervous system. Nav1.8 and Nav1.9 are expressed in sensory neurons and have a role in pain perception. Nav1.7 is broadly expressed in the peripheral nervous system and plays a role in the regulation of action potential.

Ligands and Ligand Libraries

Among other things, the present disclosure provides methods for identifying, characterizing, and/or detecting ligands for receptors. In various embodiments, ligands are toxin peptides (e.g., toxin peptides derived from an animal venom). Provided methods can include the use of libraries of toxin peptides to permit simultaneous screening of multiple candidate ligand species. Methods herein are applicable to identifying ligands that derive from (i.e., are structurally related to) any toxin. For example, methods are applicable to toxin peptides which are derived from toxins of organisms such as sea anemone (e.g., *Stichodactyla helianthus*), scorpion (e.g., *Androctonus mauretanicus, Odontobuthus doriae*), snakes (e.g., *Dendroaspis*), spiders (e.g., tarantula), and snails.

Toxins that can serve as a scaffold for toxin peptides and libraries of toxin peptides include any of the toxins listed in a Table or Figure herein. For example, one or more of kaliotoxin, dendrotoxin, ShK toxin, hongotoxin-1, tarantula venom toxin vstxl, hanatoxin, fasciculin-2, dendroaspis natriuretic peptide (DNP), sarafotoxin, *Odontobuthus doriae* OD1 toxin, *Thrixopelma pruriens* prototoxin-1, *Thrixopelma pruriens* prototoxin-2 can serve as a scaffold for generating a toxin peptide or library toxin peptides.

*Odontobuthus doriae* OD1 toxin is a ligand for voltage gated sodium channels. OD1 toxin has the following amino acid sequence:

(SEQ ID NO: 9)
GVRDAYIADDKNCVYTCASNGYCNTECTKNGAESGYCQWIGRYGNACWCI

KLPDEVPIRIPGKCR

*Thrixopelma pruriens* Protoxin-1 ProTx-I toxin is a toxin for voltage gated sodium channels. ProTx-I toxin has the following amino acid sequence:

(SEQ ID NO: 10)
ECRYWLGGCSAGQTCCKHLVCSRRHGWCVWDGTFS.

Toxin peptides and toxin peptide libraries can be generated by any of a variety of methods. Variability of toxin peptide sequences can derive from combinatorial diversity and/or introduction of sequence variation. For example, in some embodiments, a toxin peptide has an amino acid sequence which includes one or more domains from one toxin, and one or more domains from one or more other toxins. In one example, a toxin peptide includes a first domain from a first toxin, a second domain from a second toxin, and a third domain from a third toxin. In some embodiments, a toxin peptide has an amino acid sequence of a natural toxin which has been altered such that the toxin peptide has an amino acid sequence with at least 40%, 50%, 60%, 70%, 80%, 90%, 95% sequence identity to the natural toxin sequence. Sequence alterations suitable for generation of toxin peptides include insertions, deletions, substitutions, rearrangements (e.g., inversions) and combinations thereof. In some embodiments, sequence alterations are introduced into a toxin sequence at random. In some embodiments, sequence alterations are introduced into a toxin sequence in a targeted manner (e.g., to vary residues within a particular domain). In some embodiments, sequence alterations are introduced at residues other than cysteine residues (e.g., to preserve disulfide bonding). In some embodiments, sequence alterations are introduced at residues other than cysteine residues and basic residues. In some embodiments, a toxin peptide has an amino acid sequence of a natural toxin which has been altered at residues that undergo posttranslational modifications. Any and/or all of these features can be used to generate a diverse library of peptides for screening and identifying novel ligands.

In some embodiments, multiple toxins serve as a scaffold source for a single ligand, thereby providing combinatorial diversity to the range of ligand sequences that can be produced, screened, and utilized in a method described herein. A group of toxins suitable for use as a scaffold for a ligand (i.e., a "scaffold group") typically has a similar number of amino acids, and a similar arrangement of disulfide bridges. Members of a scaffold group typically have a homologous three-dimensional backbone structure. Members of a scaffold group can have very different biological properties and structural variation.

In some embodiments, members of a library include sequences that include cysteines spaced at intervals observed in a natural toxin, with variability in residues between cysteines. In certain embodiments, one or more additional residues found in a natural toxin sequence are conserved (e.g., basic residues known to be important for binding activity). In some embodiments, kaliotoxin-1 serves as a scaffold for a ligand or library thereof. In certain embodiments, members of a library include peptides that have cysteines spaced at intervals observed in kaliotoxin, i.e., the peptides include the underlined cysteines found in kaliotoxin-1: GVEINVK CSGSPQCLKPCKDAGMRFGKCMNRKCHCTPK (SEQ ID NO: 11). Such peptides have the following consensus sequence: XXXXCXXXXXCXXXCXXXXXXXXX-CXXXXCXCXX (SEQ ID NO: 12), wherein X is any amino acid.

In certain embodiments, members of a library include peptides having additional residues conserved from the kaliotoxin-1 sequence, such as the underlined residues: GVE-INVKCSGSPQCLKPCKDAGMRFGKCMNRKCHCTPK (SEQ ID NO: 13). Such peptides have the following consensus sequence: XXXXXXKCXXXXQCXXX-CXXXXXXXXXKCMXXKCXCXXX (SEQ ID NO: 14) wherein X is any amino acid.

In certain embodiments, members of a library include peptides having still additional residues conserved from the kaliotoxin-1 sequence, such as the underlined residues: GVE-INVKCSGSPQCLKPCKDAGMRFGKCMNRKCHCTPK (SEQ ID NO: 15). Such peptides have the following consensus sequence: XXXXXXKCXXXXQCLXXCK-XXXXXXXKCMXXKCXCXXX (SEQ ID NO: 16) wherein X is any amino acid. Libraries can include peptides having residues conserved from other toxins, e.g., other toxins described herein, e.g., one or more toxins from Table 1 or Table 2, Table 13, Example 20, FIG. 8, FIG. 9, FIG. 14, or FIG. 15.

In certain embodiments, the present disclosure provides a ligand that includes the following consensus sequence: IXVKCXXPXQCXXPCKXXXGXXXXXKCM-NXKCXCYX (SEQ ID NO: 17), wherein X is any amino acid. In certain embodiments, the present disclosure provides a ligand that includes the following consensus sequence: IXVKCXXPXQCXXPCKXXGXXXXKCMNXKCXCYX (SEQ ID NO: 18), wherein X is any amino acid. In some embodiments, the ligands specifically bind to a potassium channel. In some embodiments, the ligands inhibit a potassium channel.

Table 2 provides an exemplary list of toxins that share a scaffold with kaliotoxin.

TABLE 2

An Exemplary Kaliotoxin Scaffold Group

| name | scaffold member amino acid sequence | SEQ ID NO: |
|---|---|---|
| Kaliotoxin-1 (KTX) KTX_Androctonus_mau | GVEINVKCSGSPQCLKPCKD--AGMRFGKCMNRKCHCTPK | 19 |
| KTX2_Androctonus_aus | -VRIPVSCKHSGQCLKPCKD--AGMRFGKCMNGKCDCTPK | 20 |
| alpha-KTx_3_9_KAX39_BUTOC | -VGIPVSCKHSGQCIKPCKD--AGMRFGKCMNRKCDCTPK | 21 |
| *alpha-KTx_3_6_AF079062_2 | GVGINVKCKHSGQCLKPCKD--AGMRFGKCINGKCDCTPKG | 22 |
| alpha-KTx_3_8KAX38_BUTSI | GVPINVKCRGSPQCIQPCRD--AGMRFGKCMNGKCHCIPQ | 23 |
| alpha-KTx_3_5_KAX35_ANDAU | AVRIPVSCKHSGQCLKPCKD--AGMRFGKCMNGKCDCTPK | 24 |
| BmKTX_Buthus_mar | -VGINVKCKHSGQCLKPCKD--AGMRFGKCINGKCDCTPK | 25 |
| AgTX1_Leiurus_qui | GVPINVKCTGSPQCLKPCKD--AGMRFGKCINGKCHCTPK | 26 |
| AgTX2_Leiurus_qui | GVPINVSCTGSPQCIKPCKD--AGMRFGKCMNRKCHCTPK | 27 |
| AgTX3_Leiurus_qui | GVPINVPCTGSPQCIKPCKD--AGMREGKCMNRKCHCTPK | 28 |

TABLE 2-continued

An Exemplary Kaliotoxin Scaffold Group

| name | scaffold member amino acid sequence | SEQ ID NO: |
|---|---|---|
| OsK-1_Orthochirus_scr | GVIINVKCKISRQCLEPCKK--AGMRFGKCMNGKCHCTPK | 29 |
| NTX_Centruroides_nox | TI-INVKCTSPKQCSKPCKELYGSSAGAKCMNGKCKCYNN | 30 |
| KAX28_CENEL_alpha-KTx_2_8_Toxin_Ce1 | TV-INVKCTSPKQCLKPCKDLYGPHAGAKCMNGKCKCYNN | 31 |
| KAX29_CENEL_alpha-KTx2_9_Toxin_Ce2 | TI-INVKCTSPKQCLKPCKDLYGPHAGAKCMNGKCKCYNN | 32 |
| *KAX2A_CENEL_alpha-KTx_2_10_Toxin_Ce3 | IF-INVKCSLPQQCLRPCKDRFGQHAGGKCINGKCKCYP- | 33 |
| *KAX2B_CENEL_alpha-KTx_2_11_Toxin_Ce4 | TI-INVKCTSPKQCLLPCKEIYGIHAGAKCMNGKCKCYKI | 34 |
| *KAX2C_CENEL_alpha-KTx_2_12_Toxin_Ce5 | TI-INVKCTSPKQCLPPCKEIYGRHAGAKCMNGKCHCSKI | 35 |
| KAX23_CENLL_alpha-KTx_2_3_Toxin-1_C11Tx1 | IT-INVKCTSPQQCLRPCKDRFGQHAGGKCINGKCKCYP- | 36 |
| AAB32772_1_toxin_1_Centruroides_lim | IT-INVKCTSPQQCLRPCKDRFGQHAGKGCINGKCKCYP- | 37 |
| alpha-KTx_4_5_precursor_Tityus_cos | VF-INVKCRGSPECLPKCKEAIGKSAG-KCMNGKCKCYP- | 38 |
| alpha-KTx_1_5_precursor_Mesobuthus_mar | QF-TDVKCTGSKQCWPVCKQMFGKPNG-KCMNGKCRCYS- | 39 |
| TsTX-Kalpha_Tityus_ser | VF-INAKCRGSPECLPKCKEAIGKAAG-KCMNGKCKCYP- | 40 |
| alpha-KTx_4_5_KAX45_TITCO | VF-INVKCRGSPECLPKCKEAIGKSAG-KCMNGKCKCYP- | 41 |
| MgTX_Centruroides_mar | TI-INVKCTSPKQCLPPCKAQFGQSAGAKCMNGKCKCYPH | 42 |
| KAX22_CENMA_alpha-KTx_2_2_Margatoxin_MgTX | TI-INVKCTSPKQCLPPCKAQFGQSAGAKCMNGKCKCY-- | 43 |
| NTX2_Centruroides_nox | TI-INEKCFATSQCWTPCKKAIGSLQS-KCMNGKCKCYNG | 44 |
| PiTX-Kalpha_Pandinus_imp | TI-S---CTNPKQCYPHCKKETGYPN-AKCMNRKCKCFGR | 45 |
| PiTX-Kbeta_Pandinus_imp | TI-S---CTNEKQCYPHCKKETGYPN-AKCMNRKCKCFGR | 46 |
| C1TX_Centruroides_lim | IT-INVKCTSPQQCLRPCKDRFGQHAGGKCINGKCKCYP- | 47 |
| KAX25_CENLM_alpha-KTx_2_5_Hongotoxin-1_HgTX1 | TV-IDVKCTSPKQCLPPCKAQFGIRAGAKCMNGKCKCYPH | 48 |
| ChTX_Leiurus_qui | ZF-TNVSCTTSKECWSVCQRLHNTSR-GKCMNKKCRCYS- | 49 |
| IbTX_Buthus_tam | ZF-TDVDCSVSKECWSVCKDLFGVDR-GKCMGKKCRCYQ- | 50 |
| Lq2_Leiurus_qui | ZF-TQESCTASNQCWSICKRLHNTNR-GKCMNKKCRCYS- | 51 |
| Lq15-1_Leiurus_qui | GL-IDVRCYDSRQCWIACKKVTGSTQ-GKCQNKQCRCY-- | 52 |
| BmTX1_Buthus_mar | ZF-TDVKCTGSKQCWPVCKQMFGKPN-GKCMNGKCRCYS- | 53 |
| BmTX2_Buthus_mar | ZF-TNVSCSASSQCWPVCKKLFGTYR-GKCMMSKCRCYS- | 54 |
| LTX1_Leiurus_qui | AF-----CNL-RMCQLSCRSL---GLLGKCIGDKCECVKH | 55 |
| P05_Androctonus_mau | TV-----CNL-RRCQLSCRSL---GLLGKCIGVKCECVKH | 56 |
| BmP05_Buthus_mar | AV-----CNL-KRCQLSCRSL---GLLGKCIGDKCECVKH | 57 |
| P01_Anroctonus_mau alpha-KTx 8.1 | -----VSCE---DCPEHCSTQKAQ---AKCDNDKCVCEPI | 58 |
| BmP01_Buthus_mar | -----ATCE---DCPEHCATQNAR---AKCDNDKCVCEPK | 59 |

TABLE 2-continued

An Exemplary Kaliotoxin Scaffold Group

| name | scaffold member amino acid sequence | SEQ ID NO: |
|---|---|---|
| BmP02_Buthus_mar | -----VGCE---ECPMHCKGKNAK---PTCDDGVCNCN-V | 60 |
| BmP03_Buthus_mar | -----VGCE---ECPMHCKGKNAN---PTCDDGVCNCN-V | 61 |
| TsKappa_Tityus_ser | VV-IGQRCYRSPDCYSACKKLVGKAT-GKCTNGRCDC--- | 62 |

Figures 13, 14:
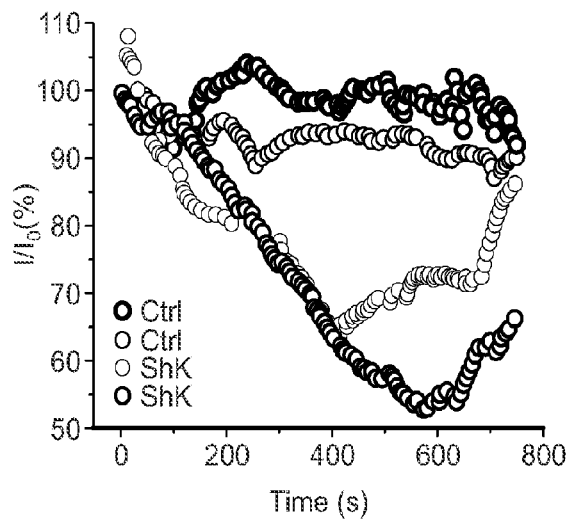
FIG. 13 is a graph depicting functional Shk expressed on the phage blocking Kv1.3 current in mammalian cells.
FIG. 14 is a table showing an alignment of peptides from toxins produced by various *Conus* species (SEQ ID NOS 204-213, respectively, in order of appearance). The disulfide bonding pattern of the peptides is indicated under each set.

An alignment of peptides from exemplary scaffolds of toxins from *Conus* marine snails are shown in FIG. 14, with disulfide bonding patterns indicated under each set of peptides (from French and Terlau, J. Med. Chem. 11:3053-3064, 2004). These *Conus* toxins target sodium channels. Another exemplary set of natural scaffolds that target sodium channels are shown in FIG. 15 (from Mouhat et al., 378(Pt 3):717-26, 2004). Any of these toxins can be used to produce toxin peptides. Libraries of toxin peptides can be produced using methods described herein. In some embodiments, toxin peptides include cysteine at positions corresponding to cysteines found in the toxin(s). In some embodiments, toxin peptides include one or more basic residues corresponding to basic residues found in the toxin(s).

Figures 9, 10:
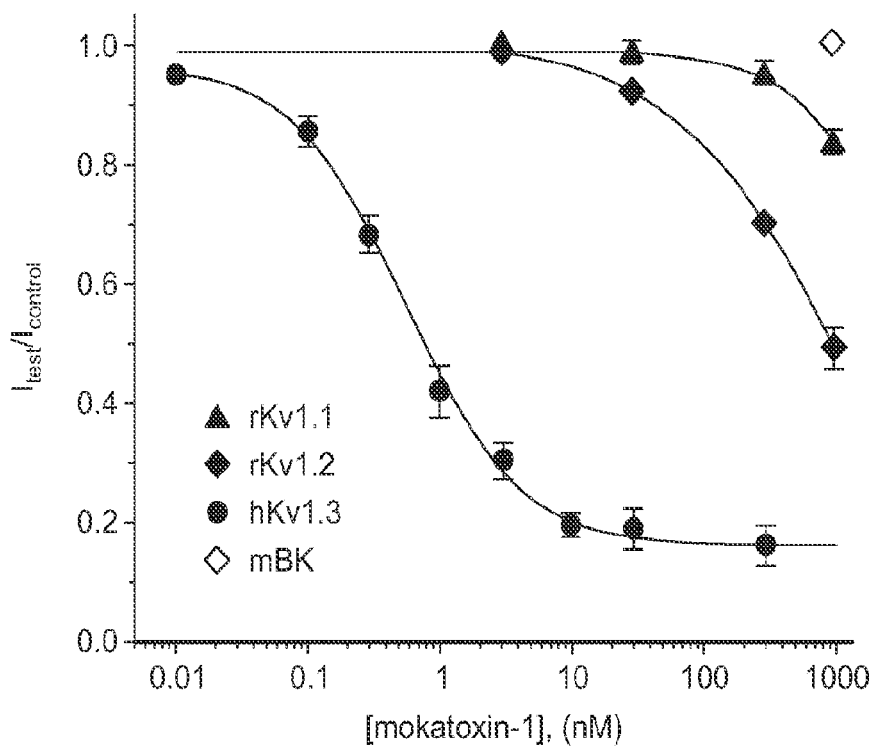
FIG. 9 is a schematic representation of the novel amino acid sequences of mokatoxin-1 (SEQ ID NO: 1), mokatoxin_0422 (SEQ ID NO: 2), and mokatoxin_0516 (SEQ ID NO: 3), and controls KTX (SEQ ID NO: 11) and inactive KTX (SEQ ID NO: 203).
FIG. 10 is a graph depicting selective blockade of wild-type Kv1.3 channels by mokatoxin-1 expressed in *Xenopus* oocytes.
Figure 11A:
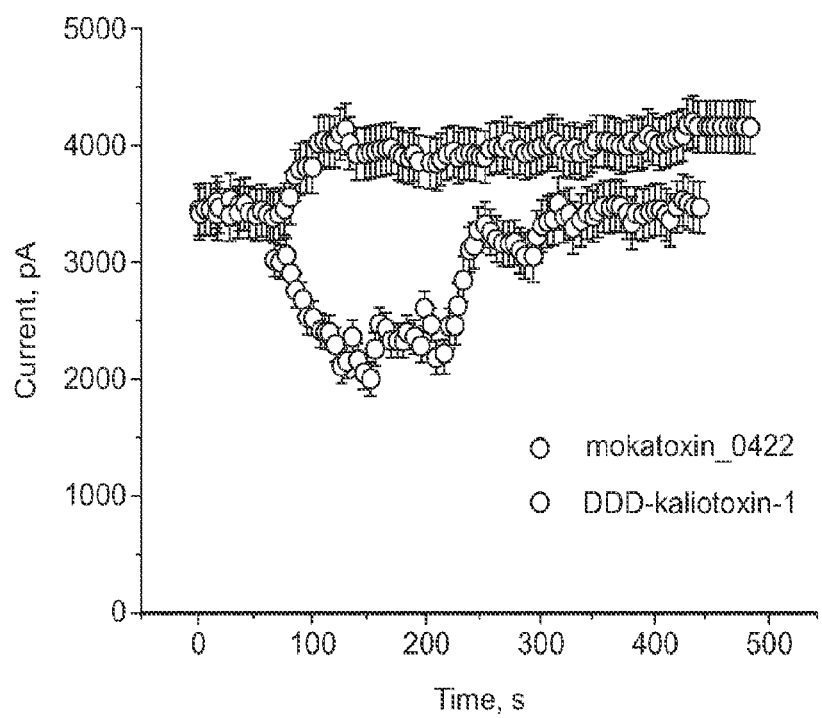
FIG. 11A is a graph depicting mokatoxin_0422-phage inhibition of Kv1.3 currents at 0.3 nM toxin-phage concentration.
Figure 11B:
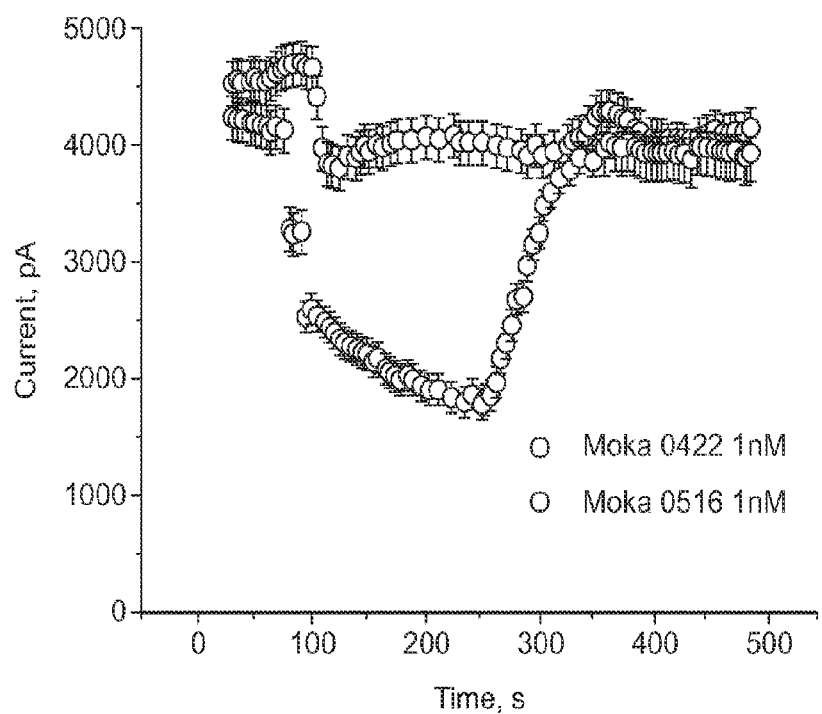
FIG. 11B is a graph depicting mokatoxin 0516-phage inhibition of Kv1.3 currents at 1.0 nM and mokatoxin_0422-phage inhibition of Kv1.3 currents at 1.0 nM toxin-phage concentration.

In one example, members of a scaffold group used to produce one or more ligands includes kaliotoxin-1, charybdotoxin, and agitotoxin-2. This combination of toxins served as a source for the novel artificial ligand mokatoxin-1, as described in Examples herein. Mokatoxin-1 (also referred to as MK-1) is composed of A, B and C domains present in at least three different species of scorpions, for example *Buthus occitanus* (AgTx2, domain A, North Africa), *Centruroides elegans* (Ce3, domain B, Central America), and *Leiurus quinquestriatus* (charybdotoxin, domain C, Middle East). As shown in FIG. 9, the sequence for mokatoxin-1 is INVKCS-LPQQCIKPCKDA GMRFGKCMNKKCRCYS (SEQ ID NO: 1). Further novel neurotoxin-like sequences depicted in FIG. 9 include mokatoxin_0422, TVIDVKCTSPKQCLPP CKAQFGIRAGAKCMNKKCRCYS (SEQ ID NO: 2), and mokatoxin_0516, TVINV KCTSPKQCLRPCKDRF-GQHAGGKCMNGKCKCYPH (SEQ ID NO: 3).

Scaffolds are not limited to venom toxins. For example, certain non-venom peptides from mammals share a scaffold with venom toxins. Such peptides can be employed in a scaffold group to produce novel ligands in accordance with the present disclosure. To give one example, dendroaspis natriuretic peptide from mamba snake venom and human brain natriuretic peptide fall into a scaffold group. Derivatives and/or portions of these peptides can be synthesized and/or combined to produce novel ligands.

Ligands (e.g., toxin peptides) can be produced by any method. In some embodiments, a ligand is produced by recombinant expression in a cell. In some embodiments, a ligand is produced by peptide synthesis. In some embodiments, a ligand is produced by in vitro translation.

Ligands can be inserted into vectors for expression and/or library selection. In some embodiments, a library is presented in a protein array (see, e.g., U.S. Pat. No. 5,143,854; De Wildt et al., Nat. Biotechnol. 18:989-994, 2000; Lueking et al., Anal. Biochem. 270:103-111, 1999; Ge, Nucleic Acids Res. 28, e3, I-VII, 2000; MacBeath and Schreiber, Science 289: 1760-1763, 2000; WO 01/98534, WO 01/83827, WO 02/12893, WO 00/63701, WO 01/40803 and WO 99/51773). In some embodiments, a library is presented on a replicable genetic package, e.g., in the form of a phage library such as a phage display, yeast display library, ribosome display, or nucleic acid-protein fusion library. See, e.g., U.S. Pat. No. 5,223,409; Garrard et al. (1991) Bio/Technology 9:1373-1377; WO 03/029456; and U.S. Pat. No. 6,207,446. Binding members of such libraries can be obtained by selection and screened in a high throughput format. See, e.g., U.S. 2003-0129659.

In one example, a nucleic acid sequence encoding a ligand may be inserted into a phagemid or phage vector, in-frame, to form a leader-linker-ligand-linker-coat protein construct (Clackson and Lowman, Phage display. Oxford University Press, 2004; Barbas et al., Phage display. A laboratory manual. Cold Spring Harbor Laboratory Press, 2001). For example, FIG. 1 schematically depicts KTX incorporated into a phagemid vector, in frame, fused by N and C-terminal linker sequences between the leader sequence and the phage coat protein III. Exemplary upstream and downstream leader amino acid sequences are AEGA (SEQ ID NO: 63) and GSASSA (SEQ ID NO: 64), respectively, and an exemplary coat protein is protein III or its truncated version. Phages can be grown, prepared, titered and stored (Clackson and Lowman, Phage display. Oxford University Press, 2004; Barbas et al., Phage display. A laboratory manual. Cold Spring Harbor Laboratory Press, 2001).

Ligand libraries for phage display can be generated by standard methods (Clackson and Lowman, Phage display. Oxford University Press, 2004; Barbas et al., Phage display. A laboratory manual. Cold Spring Harbor Laboratory Press, 2001). In one example, ligand libraries for phage display with a combinatorial arrangement of ligand-domains are generated by designing overlapping or non-overlapping oligonucleotides corresponding to each individual domain. These oligonucleotides are phosphorylated, annealed, mixed in a desired combination and concentration and ligated into a phagemid vector with or without linker sequences to create a library by standard methods (Sambrook et al., Molecular Cloning: A Laboratory Manual. Vols 1-3. Cold Spring Harbor Laboratory Press, 1989). For example, ligands may be composed by domains A1B1C1, A1B2C1, and A3B2C1, respectively. A combinatorial library of ligands in this representative example yields the pattern AnBnCn, where n is the i-th domain (for example, A2B1C3 is a novel ligand present in this library).

Library diversity is verified by sequencing or by other physical, chemical or biochemical means, either with or without statistical analysis, that is suitable to use for diversity verification. Domains can be defined by functional, structural or sequence properties and can be of any length and a domain can be present or absent. Domains can be singular or highly varied to expand diversity. Standard protocols of molecular biology may be employed (Sambrook et al., Molecular Cloning: A Laboratory Manual. Vols 1-3. Cold Spring Harbor Laboratory Press, 1989).

In one example, a library includes toxin peptides (e.g., toxin peptides having sequences from one or more animal toxins). Toxin peptide libraries can include peptide animal toxins in their native or natural (wild-type) form or in any variation in amino acid sequence or may be comprised of DNA and/or RNA sequences encoding animal toxins. The library may contain toxins representing one or more scaffolds (also known as toxin-types or toxin families). For example, in some embodiments, a library includes toxin peptides from scorpion toxins, venom three-finger molecular scaffolds, or animal toxins that interact with $K^+$ ion channels irrespective of the toxin's scaffold and species origin. In some embodiments, a library includes all known toxins from a given species, or all known toxins from all species.

In one example, an animal toxin library may include toxins from one or more of sea anemone, scorpion, and snake. Sea anemone *Stichodactyla helianthus* ShK toxin is pharmacologically active and blocks Kv1.3 $K^+$ channels in mammalian cells when expressed on the phage. Scorpion *Androctonus mauretanicus* kaliotoxin-1 is pharmacologically active and blocks Kv1.3 $K^+$ channels in mammalian cells when expressed on the phage. Snake venom toxin *Dendroaspis* dendrotoxin is pharmacologically active and blocks Kv1.1 $K^+$ channels in mammalian cells when expressed on the phage (see FIG. 12, upper panel), while Camel VHH, a non-specific-phage (see FIG. 12, middle panel) or phage buffer (see FIG. 12, bottom panel) cause no block.

In some embodiments, a library is incorporated into a phage display system. In phage display, candidate ligands (e.g., toxin peptides) are functionally displayed on the surface of the phage and nucleic acid sequences encoding the ligands are enclosed inside phage particles. The functional display permits the selection of ligands that interact with a target or targets. A selection can be based on the ligand type (e.g., toxin type) and/or target biochemistry, pharmacology, immunology and/or other physicochemical or biological property. For example, a $K^+$ channel toxin can be identified by screening scorpion toxin library on a $K^+$ channel for binding to the channel.

In one example, a toxin peptide library is constructed and maintained such that each toxin peptide is individually constructed and stored and can be mixed into the library in any desired combination for the test to be performed. In another example, two or more toxin peptides may be constructed in the same reaction and stored and used together.

A phage library can be transfected into *E. coli* or other suitable bacterial species, propagated and the phages purified. At this stage, ligands (e.g., toxin peptides) can be functionally expressed on the surface of the phage and physically linked to their respective genes inside of the phage particle. A library is brought into contact with a target. After incubation with the target, those phages that express a ligand with no or weak recognition for the target are washed away. The remaining ligands that interact with the target are dissociated and can be (i) genotyped to establish the ligand identity, or (ii) processed for one or more rounds of panning, or (iii) otherwise quantified and/or identified (e.g., ELISA, microbiological titering, functional testing).

A ligand library (e.g., toxin peptide library) may created by any known method. For example, a toxin library may be created by collecting peptides and/or nucleic acids encoding animal toxins and, if desired, non-venom homologues. Non-venom homologues include any molecule present outside of a venom gland or not used as a venom component but similar in sequence or structure to toxins. In applications employing phage display, N-terminal and C-terminal nucleotide sequences can be designed to join sequences for subcloning into a phagemid or other phage-display compatible vector. Overlapping or nonoverlapping DNA oligonucleotides are designed and synthesized for synthetic genes. This includes positive and negative DNA strands and N-terminal and C-terminal joining regions. The respective DNA oligonucleotide pairs (positive and negative strands) and sets are phosphorylated and annealed to create full length genes (e.g., genes encoding toxin peptides) with or without joining regions. Ligation into phagemid or other phage-display compatible vector is performed, for example using coat protein III as a fusion protein. Other suitable phage proteins may also be used. The sequences or genotypes can be confirmed.

The strategy described above was used to produce a library of ligands. Amino acid sequences from members of the library are shown in FIG. 2. Seventy out of 120 (58.3%) sequences are scorpion $K^+$ channel toxin scaffolds. MAAE (SEQ ID NO: 65) is the C terminal part of the signal peptide/secretion peptide-cleavage domain, position −4 to 0 relative to the toxin sequence. GSASSA (SEQ ID NO: 64) is an N-terminal linker region, which was placed immediately following the toxin sequence.

In some embodiments, a linker sequence used to connect a ligand (e.g., toxin) sequence to a signal peptide and/or a coat protein of a phage (for phage display methods) and/or to any other domain is varied to optimize one or more of ligand expression, binding, or function. Varied sequences can be produced by any method. Table 3 below lists linker sequences generated by Kunkel mutagenesis. "STM" corresponds to a C-terminal portion of one exemplary signal peptide. This is followed by a variable linker sequence of five amino acids, and an "AAK" sequence, which is one example of an N-terminal sequence that can follow a linker segment.

TABLE 3

Exemplary Linker Segments for Expression of Ligands

| | STM.....AAK | SEQ ID NO: |
|---|---|---|
| 1 | STMADLHDAAK | 66 |
| 2 | STMASTEFAAK | 67 |
| 3 | STMAVDGVAAK | 68 |
| 4 | STMCQPELAAK | 69 |
| 5 | STMEQVDAAAK | 70 |
| 6 | STMGSDMHAAK | 71 |
| 7 | STMHTDYTAAK | 72 |
| 8 | STMLELTSAAK | 73 |
| 9 | STMLLTVPAAK | 74 |
| 10 | STMPLAGPAAK | 75 |
| 11 | STMSVSVSAAK | 76 |

Methods of Identifying, Characterizing, and/or Detecting Ligands

Ligands (e.g., toxin peptides) can be evaluated for binding to a receptor or for modulating activity of a receptor by any available method.

Library Screening

The following provides exemplary methods for screening a display library. The methods can also be modified and used in combination with other types of libraries, e.g., an expression library or a protein array, and so forth. Ligands (e.g., a library of toxin peptides having varied amino acid sequences) can be displayed on phage, e.g., filamentous phage. Library members having a desired degree of affinity for and/or activity toward a receptor of interest can be identified using immobilized or immobilizable receptors.

In some embodiments, a phage library is contacted with and allowed to bind to the target of interest. To facilitate separation of binders and non-binders in the selection process, it is often convenient to immobilize the receptor on a solid support, although it is also possible to first permit binding to the target receptor in solution and then segregate binders from non-binders by coupling the receptor to a support. Bound phage may then be liberated from the receptor by a number of means, such as changing the buffer to a relatively high acidic or basic pH (e.g., pH 2 or pH 10), changing the ionic strength of the buffer, adding denaturants, adding a competitor, adding host cells which can be infected (Hogan et al., Biotechniques 38(4):536, 538, 2005), or other known means.

In some embodiments, receptors are purified prior to ligand selection. For example, purified or partially purified natural, synthetic or semi-synthetic receptors, such as KcsA carrying the toxin binding domain of a mammalian $K^+$ channel Kv1.3, may be prepared and immobilized on a surface, such as a 96-well MaxiSorp (Nalgene Nunc International, Rochester, N.Y.) plate or comparable surface suitable for immobilization and panning.

In another example, receptors may be expressed in cells. For example, cells may be stably or transiently transfected with one or more receptors can be utilized as expressed in native tissues (Clackson and Lowman, Phage display. Oxford University Press, 2004; Barbas et al., Phage display. A laboratory manual. Cold Spring Harbor Laboratory Press, 2001; Sambrook et al., Molecular Cloning: A Laboratory Manual. Vols 1-3. Cold Spring Harbor Laboratory Press, 1989). In one example, HEK (mammalian human embryonic kidney) and COS cells expressing wild-type Kv1.3 or Kv1.3-PDZ domain chimera were employed, the latter target allowing a "double" panning (e.g., as a control or to enhance binding affinity) using phages expressing kaliotoxin-1 and/or PDZ-binder domain.

Panning may be performed by the binding of ligands to the receptors, followed by washes and ligand recovery. In one example, panning is performed according to standard methods of phage display (Clackson and Lowman, Phage display. Oxford University Press, 2004; Barbas et al., Phage display. A laboratory manual. Cold Spring Harbor Laboratory Press, 2001). Panning may be repeated until the desired enrichment is achieved. In addition, libraries can be pre-depleted on surfaces or cells that contain no receptors or on a receptor where the putative ligand receptor domain may be directly or indirectly altered. Additionally, any and all conditions of panning may be varied, altered or changed to achieve optimal results, such as the isolation of a specific ligand. Panning variations include, but are not limited to, the presence of competing ligand(s), presence of excess target(s), length and temperature of binding, pre-absorption of the ligand library on one or more different receptor(s) or cells or surfaces, composition of binding solution (e.g., ionic strength), stringency of washing, and recovery procedures. Phages recovered from panning may be processed for further rounds of panning, functional analysis, and/or sequencing/genotyping to deduce the resulting ligands' amino acid sequence or biological properties (Clackson and Lowman, Phage display. Oxford University Press, 2004; Barbas et al., Phage display. A laboratory manual. Cold Spring Harbor Laboratory Press, 2001).

Following ligand recovery, ligands of interest may be produced in native form by standard methods of peptide/protein synthesis/production (Sambrook et al., Molecular Cloning: A Laboratory Manual. Vols 1-3. Cold Spring Harbor Laboratory Press, 1989; Albericio, Solid-Phase Synthesis: A Practical Guide. CRC, 2000; Howl, Peptide Synthesis and Applications. Humana Press, 2005).

Characterization of Binding Interactions

The binding properties of a ligand (e.g., a toxin peptide) can be readily assessed using various assay formats. Techniques useful for evaluating binding of a ligand (e.g., a toxin peptide) to a receptor (e.g., a channel protein) include ELISA, surface plasmon resonance, Biomolecular Interaction Analysis, and the like. In some embodiments, binding interactions are analyzed using an ELISA assay. For example, the ligand to be evaluated is contacted to a microtitre plate whose bottom surface has been coated with the target receptor, e.g., a limiting amount of the receptor. The ligand is contacted to the plate. The plate is washed with buffer to remove non-specifically bound ligands. Then the amount of the ligand bound to the plate is determined by probing the plate with an antibody that recognizes the ligand. For example, the ligand can include an epitope tag. The antibody can be linked to an enzyme such as alkaline phosphatase, which produces a colorimetric product when appropriate substrates are provided. In the case where a display library member includes the protein to be tested, the antibody can recognize a region that is constant among all display library members, e.g., for a phage display library member, a major phage coat protein.

A binding interaction between a ligand and a particular receptor can be analyzed using surface plasmon resonance (SPR). For example, before or after sequencing of a display library member present in a sample, and optionally verified, e.g., by ELISA, the displayed ligand can be produced in quantity and assayed for binding the target using SPR. SPR or real-time Biomolecular Interaction Analysis (BIA) detects biospecific interactions in real time, without labeling any of the interactants (e.g., BIAcore). Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Information from SPR can be used to provide an accurate and quantitative measure of the equilibrium dissociation constant ($K_D$), and kinetic parameters, including $k_{on}$ and $k_{off}$, for the binding of a ligand (e.g., a toxin peptide) to a target receptor (e.g., an ion channel). Such data can be used to compare different ligands. Information from SPR can also be used to develop structure-activity relationship (SAR). For example, if the ligands are all mutated variants of a single parental toxin or a set of known toxins, variant amino acids at given positions can be identified that correlate with particular binding parameters, e.g., high affinity and slow $k_{off}$. Additional methods for measuring binding affinities include nuclear magnetic resonance (NMR), and binding titrations (e.g., using fluorescence energy transfer). Other solution measures for studying binding properties include fluorescence resonance energy transfer (FRET), NMR, X-ray crystallography, molecular modeling, and measuring bound vs. free molecules. Measurement of bound vs. free molecules can be accomplished with a KinExA instrument from Sapidyne Instruments Inc., Boise, Id.

Characterization of Biological Activity

In addition to, or instead of, receptor binding, biological activity of ligands can be characterized in methods provided by the present disclosure. Biological activities of ligands can be characterized by any available means. In some embodiments, a ligand is a toxin peptide and a receptor is an ion channel. In these embodiments, methods for assessing channel activity can be employed. Methods for assessing ion channel activity include, for example, assays that measure voltage, current, membrane potential, and ion flux.

In some embodiments, ligands are tested for activity toward recombinant or naturally expressed functional ion channels. Samples that include functional channels (e.g., cells or artificial membranes) can be treated with a ligand and compared to control samples (e.g., samples without the ligand), to examine the extent of modulation. Changes in ion flux may be assessed by determining changes in polarization (i.e., electrical potential) of a cell or membrane expressing a channel. In some embodiments, a change in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., New Engl. J. Med. 336:1575-1595, 1997). Whole cell currents can be determined using standard methodology (see, e.g., Hamil et al., PFlugers. Archiv. 391:85, 1981). Other assays include radiolabeled rubidium flux assays and fluorescence assays using voltage-sensitive dyes (see, e.g., Vestergarrd-Bogind et al., J. Membrane Biol. 88:67-75, 1988; Daniel et al., J. Pharmacol. Meth. 25:185-193, 1991; Holevinsky et al., J. Membrane Biology 137:59-70, 1994). In some embodiments, ligands to be tested are present in the range from 1 pM to 100 mM. Other methods for assessing a ligand's effects on ion flux are described in the Examples herein. In some embodiments, the ability of a ligand to modulate (e.g., inhibit) a non-target receptor is tested, in addition to its ability to modulate a target receptor.

Ligands can be tested to evaluate other types of biological effects, such as effects downstream of receptor activity. For example, Kv1.3 channels are expressed in T lymphocytes. Inhibitors of Kv1.3 channels suppress T cell activation in vitro and delayed type hypersensitivity in vivo, and have immunosupporessive activity in animal models of autoimmunity (Beeton et al., 98:13942-13947, 2001; Koo et al., J. Immunol. 5120-5128, 1997). Accordingly, a candidate ligand for a Kv1.3 receptor can be evaluated for the ability to suppress T cell activation in vitro and/or T cell dependent pathologies in vivo. Assays appropriate for other ligand-receptor combinations would be apparent to one of skill in the art. Various exemplary effects of ligands that may be determined using intact cells or animals include transmitter release (e.g., dopamine), hormone release (e.g., insulin), transcriptional changes, cell volume changes (e.g., in red blood cells), changes in cell metabolism such as cell growth or pH changes, and changes in intracellular second messengers such as $Ca^{2+}$.

Ligands can be selected for their potency and selectivity of modulation of a target receptor. In some embodiments, a ligand is assayed for its potency toward a panel of receptors and an $IC_{50}$ value is determined for each. A ligand that demonstrates a low $IC_{50}$ value for the target receptor, and a higher $IC_{50}$ value for other receptors within the test panel, is considered to be selective toward the target receptor. Generally, a ligand is deemed selective if its $IC_{50}$ value is at least one order of magnitude less than the next smallest $IC_{50}$ value measured in the panel.

Pharmaceutical Compositions & Treatments

The present disclosure also features compositions including novel ligands described herein. In some embodiments, a composition is a pharmaceutically acceptable composition that includes a novel ligand described herein. The pharmaceutical composition can include a pharmaceutically acceptable carrier.

Exemplary carriers include any and all solvents, dispersion media, coatings, antibacterial and antifungal agents, isotonic and absorption delaying agents, and the like that are physiologically compatible. Preferably, the carrier is suitable for oral, intravenous, intramuscular, subcutaneous, parenteral, spinal or epidermal administration (e.g., by injection or infusion). Depending on the route of administration, the ligand may be coated in a material to protect the compound from the action of acids and other natural conditions that may inactivate the compound.

The pharmaceutical composition can include a pharmaceutically acceptable salt, e.g., a salt that retains the desired biological activity of the ligand and does not impart any undesired toxicological effects (see e.g., Berge, S. M., et al., J. Pharm. Sci. 66:1-19, 1977).

The pharmaceutical composition may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical compositions are in the form of injectable or infusible solutions, such as compositions similar to those used for administration of antibodies to humans. A common mode of administration is parenteral (e.g., intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion). In one embodiment, the ligand composition is administered by intravenous infusion or injection. In another embodiment, the ligand composition is administered by intramuscular or subcutaneous injection. In another embodiment, the ligand composition is administered orally. In some embodiments, the ligand composition is administered topically. In some embodiments, the ligand composition is administered transdermally. Pharmaceutical compositions typically must be sterile and stable under the conditions of manufacture and storage.

The composition including a ligand can be formulated as a solution, microemulsion, dispersion, liposome, or other ordered structure suitable to high drug concentration. Sterile injectable solutions can be prepared by incorporating the ligand in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Novel ligands described herein can be administered by a variety of methods known in the art. For many applications, the route/mode of administration is intravenous injection or infusion. For example, for therapeutic applications, a ligand composition can be administered by intravenous infusion at a rate of less than 30, 20, 10, 5, or 1 mg/min to reach a dose of about 1 to 100 mg/m² or 7 to 25 mg/m². Alternatively, the dose could be 100 μg/Kg, 500 μg/Kg, 1 mg/Kg, 5 mg/Kg, 10 mg/Kg, or mg/Kg. The route and/or mode of administration will vary depending upon the desired results.

In certain embodiments, a ligand is prepared with a carrier that protects against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978. Pharmaceutical formulation is a well-established art, and is further described in Gennaro (ed.), Remington: The Science and Practice of Pharmacy, 20.sup.th ed., Lippincott, Williams & Wilkins, 2000 (ISBN: 0683306472); Ansel et al., Pharmaceutical Dosage Forms and Drug Delivery Systems, 7.sup.th Ed., Lippincott Williams & Wilkins Publishers, 1999 (ISBN: 0683305727); and Kibbe (ed.), Handbook of Pharmaceutical Excipients American Pharmaceutical Association, 3$^{rd}$ ed., 2000 (ISBN: 091733096X).

Also provided by the present disclosure are kits that include a ligand described herein and instructions for use, e.g., treatment, prophylactic, or diagnostic use.

In addition to the ligand, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the ligand. In such embodiments, the kit can include instructions for admixing the ligand and the other ingredients, or for using the ligand together with the other ingredients.

A novel ligand described herein (e.g., a mokatoxin) can be administered, alone or in combination with, a second agent to a subject, e.g., a patient, e.g., a patient, who has a disorder (e.g., a Kv1.3-mediated disorder), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. The treatment may also delay onset, e.g., prevent onset, or prevent deterioration of a condition.

A therapeutically effective amount can be administered, typically an amount of the ligand which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects. A therapeutically effective dosage preferably modulates a measurable parameter, favorably, relative to untreated subjects. The ability of a ligand to inhibit a measurable parameter can be evaluated in an animal model system predictive of efficacy in a human disorder.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of ligand calculated to produce the desired therapeutic effect in association with the required pharmaceutical carrier.

An exemplary, non-limiting range for a therapeutically or prophylactically effective amount of a ligand described herein is 0.1-20 mg/Kg, more preferably 1-10 mg/Kg. The compound can be administered by parenteral (e.g., intravenous or subcutaneous) infusion at a rate of less than 20, 10, 5, or 1 mg/min to reach a dose of about 1 to 50 $mg/m^2$ or about 5 to 20 $mg/m^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions (e.g., the supervising physician), and that dosage ranges set forth herein are only exemplary.

Therapeutic Uses

Novel ligands described herein may be used in therapies for the treatment or prophylaxis of disorders mediated target receptors (e.g., Kv1.3 channels). Kv1.3 channels are a therapeutic target for immunosuppressants. Accordingly, novel ligands described herein that inhibit activity of Kv1.3 channels are useful in the treatment of immune disorders. In some embodiments, a novel ligand is used to treat autoimmune and/or chronic inflammatory diseases, such as systemic lupus erythematosis, chronic rheumatoid arthritis, type I and II diabetes mellitus, inflammatory bowel disease, biliary cirrhosis, uveitis, multiple sclerosis, graft versus host disease, graft rejection, and other disorders such as Crohn's disease, ulcerative colitis, bullous pemphigoid, sarcoidosis, psoriasis, ichthyosis, Sjogren's syndrome, scleroderma, mixed connective tissue disease, dermatomyositis, polymyositis, Reiter's syndrome, Behcet's disease, myasthenia gravis, encephalomyelitis, Graves ophthalmopathy, psoriasis, neurodermitis and asthma While various aspects and examples have been described, it will be apparent to those of ordinary skill in the art that many more examples and implementations are possible within the scope of the invention. Accordingly, the disclosure is not to be restricted except in light of the attached claims and their equivalents.

EXAMPLES

Reference will now be made in detail to several examples. While the disclosure will be described in conjunction with these examples, it will be understood that it is not intended to limit the claimed invention to such examples. In the following description, numerous specific details are set forth in the examples in order to provide a thorough understanding of the subject matter of the claims which, however, may be practiced without some or all of these specific details. In other instances, well known process operations have not been described in detail in order not to unnecessarily obscure the description.

Example 1

Live Cells—Kv1.3 Cells vs. Vector

In one example, KTX was preferentially bound to HEK and COS cells expressing Kv1.3 channels vs. cells not expressing Kv1.3 (vector). As shown in FIG. 3, panning on Kv1.3 transfected cells compared to the vector cells enriches for KTX. "A" shows about a 10-fold enrichment of KTX when screened on COS cells transfected with Kv1.3 vs. the vector. $5 \times 10^{11}$ phagemids were added to the cell cultures in "A." "B" shows an approximate 20-fold enrichment of KTX when screened on HEK cells transfected with Kv1.3 vs. the vector. $5 \times 10^{11}$ phagemids were added to the cell cultures in "B."

Example 2

Live Cells—KTX Ligands vs. Non-Specific Ligands

In another example, KTX was preferentially enriched when a mixture of non-specific and KTX ligands was panned on cells expressing Kv1.3 channels. As shown in Table 4, KTX was selected over non-KTX ligands when panning was performed on mammalian cells expressing Kv1.3 channels.

TABLE 4

| INPUT | | OUTPUT | |
|---|---|---|---|
| KTX phages/nonspecific phages (%) | | | Fold |
| Calculated | Actual | KTX (%) | Enrichment |
| 10/90 | 7/93 (n = 30) | 30 (n = 30) | 4.3 |
| 1/99 | 5/95 (n = 20) | 26 (n = 20) | 5.2 |
| 10/90 | 0/100 (n = 10) | 22 (n = 18) | enrichment |

In the first input, the calculated ratio was 10 KTX phagemids per 100 phages. The actual ratio, averaged over 30 samples, was 7 KTX phagemids per 100 phages. After one round of panning, the output ratio increased to 30 KTX phagemids per 100 phages, resulting in a 4.3 fold enrichment.

In the second input, the calculated ratio was 1 KTX phagemid per 100 phages. The actual ratio, averaged over 20 samples, was 5 KTX phagemids per 100 phages. After one round of panning, the output ratio increased to 26 KTX phagemids per 100 phages, resulting in a 5.2 fold enrichment.

In the third input, the calculated ratio was 10 KTX phagemid per 100 phages. The actual ratio, averaged over 10 samples, was 0 KTX phagemids per 100 phages. However, after one round of panning, the output ratio increased to 22 KTX phagemids per 100 phages. The third input shows enrichment of KTX, however the enrichment cannot be quantified due to no KTX phages being present in the 10 input samples.

Example 3

Live Cells—KTX-like Ligands vs. Non-KTX-like Ligands

In a further example, KTX-like ligands (e.g., having a KTX-like protein scaffold) were preferentially enriched when a mixture of non-specific and KTX-like ligands were panned on cells expressing Kv1.3 channels. A library of KTX-like ligands, with a calculated diversity of greater than 11,000, was created de novo. The library comprised approximately 8% KTX-like ligands and 92% non-KTX-like ligands. The library of ligands was screened on Kv1.3 receptors expressed in HEK and COS cells. As shown in Table 5, one round of panning (n=20-40 samples) specifically enriched the KTX-like ligands compared to the input library.

TABLE 5

| Cell Type | Input (% KTX-like ligands) | Output (1 round of panning) |
|---|---|---|
| HEK | 8 | 40% KTX-like |
| COS | 8 | 35% KTX-like |

Verification of the above Examples 1-3 was performed by quantification of the elutes, and/or by genotyping the input versus output ligands.

Example 4

Purified Receptors-enriching KTX from Mixture of Ligands

A mixture of five ligands: (1) kaliotoxin-1; (2) sarafotoxin s6b; (3) *Dendroaspis* natriuretic peptide (DNP); (4) fasciculin-2; and (5) camel antibody (CVHH); were mixed and panned on purified receptors (KcsA-Kv1.3). The control was immobilized antiserum to sarafotoxin s6b (anti-S6b). Input and output ligands were verified by genotyping. In this system, shown in Table 6, a 3.6-fold enrichment is seen after one-round of panning.

TABLE 6

| | Input (% Ligands) | | Output (% Ligands) | |
|---|---|---|---|---|
| | | | KcsA-Kv.13 | Anti-S6b |
| Ligand | Calculated | Actual (n = 14) | (n = 20) | (n = 20) |
| Kaliotoxin-1 | 20 | 28 | 100 | 0 |
| Sarafotoxin s6b | 20 | 36 | 0 | 100 |
| DNP | 20 | 28 | 0 | 0 |
| Fasciculin-2 | 20 | 0 | 0 | 0 |
| CVHH | 20 | 7 | 0 | 0 |

Example 5

Purified Receptors-Enriching for Novel KTX-like Ligands from Library

A library of KTX-like ligands, with a calculated diversity of greater than 11,000, was created de novo. The library comprised approximately 8% KTX-like ligands and 92% non-KTX-like ligands. This library of ligands was screened for novel ligands on (1) an immobilized target comprising Kv1.3 and (2) a control comprising KcsA. As shown in Table 7, a first and second round of panning specifically enriches KTX-like ligands in Kv1.3, but not in KcsA.

TABLE 7

| | % of KTX-like ligands (n = 20-40) | | |
|---|---|---|---|
| Receptor | Input | 1st Panning | 2nd Panning |
| Kv1.3 | 8 | 15 | 38 |
| KcsA | 8 | 0 | 0 |

Example 6

Purified Receptors—Quantification of Phages by ELISA

Figure 4:
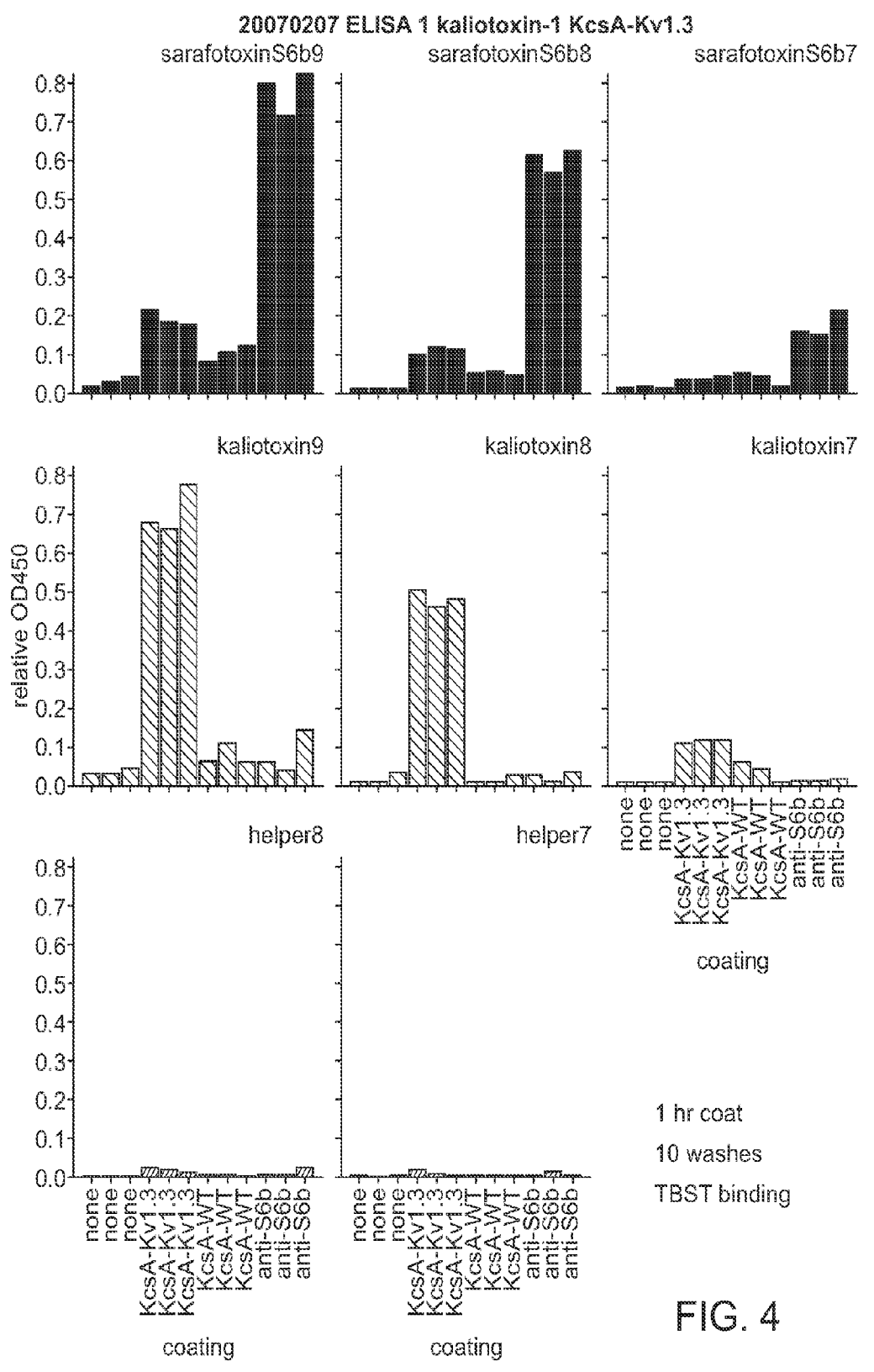

Panning was performed, in triplicate, on surfaces without a coating (none), and on immobilized KcsA-Kv1.3 receptors (KcsA-Kv1.3), wild-type KcsA receptors (KcsA-WT), and antiserum to sarafotoxin S6b (anti-S6b). The input ligands per well are $10^9$, $10^8$, $10^7$. The ligands included: sarafotoxin S6b (upper panel FIG. 4), kaliotoxin-1 (KTX, middle row FIG. 4), no ligand helper phages (bottom row FIG. 4). The data, shown in FIG. 4, indicates specific binding of sarafotoxin S6b to anti-S6b, and KTX to KcsA-Kv1.3.

Example 7

DNP and Saratoxin S6b-Antiserum Reacts with Phages

Figure 5:
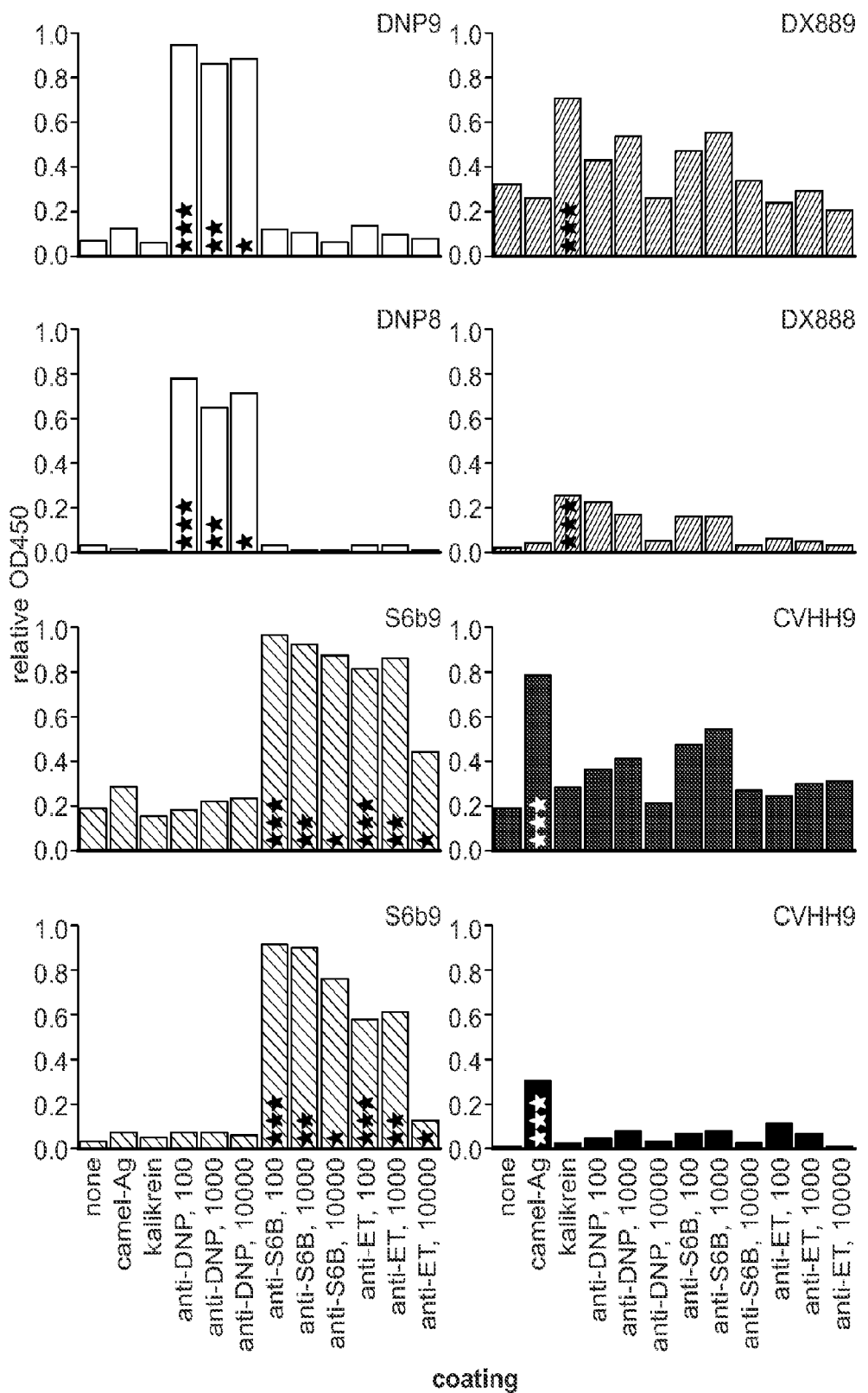
FIG. 5 is a set of graphs depicting the preferential selection of animal venom toxin snake *Dendroaspis* natriuretic peptide (DNP) and snake *Atractaspis* sarafotoxin S6b ligands in a phage display system on antiserum raised against DNP and S6b, respectively.

As depicted in FIG. 5, *Dendroaspis* natriuretic peptide (DNP) and sarafotoxin S6b (S6b) ligands in a phage display system are preferentially selected on antiserum raised against DNP and S6b, respectively. Based on its structural similarity, S6b also selected, but in a lesser extent, on antiserum raised against endothelin. The controls included DX88 (a kallikrein ligand) and CVHH (a camel-Ag ligand). The number 8 or 9 following the ligand name, in FIG. 5, indicates $10^8$ or $10^9$ phages per reaction, respectively.

Example 8

Mokatoxin-1, a Kv1.3-specific Artificial Neurotoxin

To confirm that a natural animal venom neurotoxin can bind to a known Kv channel site when expressed on the surface of a phage particle, a phagemid was constructed with KTX of the scorpion *Androctonus mauretanicus* encoded on the N-terminus and in-frame with phage coat protein III. As a control, a phage expressing a mutant toxin, DDD-KTX, was synthesized. DDD-KTX does not bind to KTX sites because three basic residues on the KTX interaction surface are altered to aspartate (R24D, K27D, R31D).

For each binding determination, 3 wells in a NUNC-Immuno MaxiSorp 96-Well plates were coated overnight at 4° C. with 1 ug of KcsA-1.3 or KcsA in 50 ul of 100 mM $NaHCO_3$, 1 mM DDM, pH 9, then washed once with Tris-HC150 mM, NaCl-150 mM pH7.5 containing 0.1% Tween 20, 1 mM DDM (TBST). Wells were then blocked at room temperature with 200 ul of Tris 50 mM NaCl 150 mM pH 7.5, 1 mM DDM, (TBS) containing 0.5% BSA, then washed once with TBST. For each well, 108-1010 phages were added in 50 ul of TBS containing 0.5% BSA and incubated on a rotary shaker at room temperature for 2 hrs. Following five washes with TBST, 50 ul of anti-phage antibody-peroxidase conjugated TBST with 0.5% BSA was added and incubated on a rotary shaker for 2 hours at room temperature, then washed 5 times with TBST and twice with TBS. Fifty (50) ul of 1 step turbo-TMB-ELISA was added and the reaction is stopped by 50 µl of 2M $H_2SO_4$ and the absorbancy was read at 450 nM.

Figure 6A:
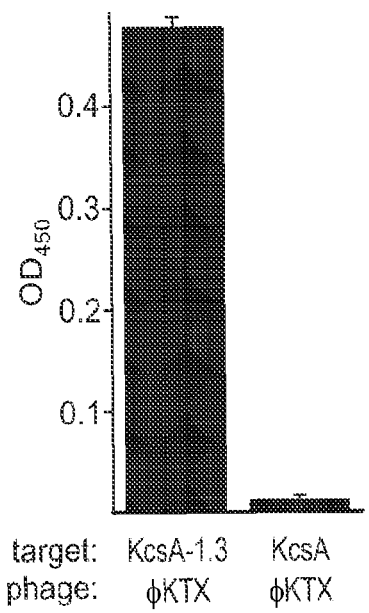
FIGS. 6A and B is a set of graphs depicting KTX binding to KcsA carrying the Kv1.3 pore domain (KcsA-1.3), quantified by ELISA.
Figure 6B:
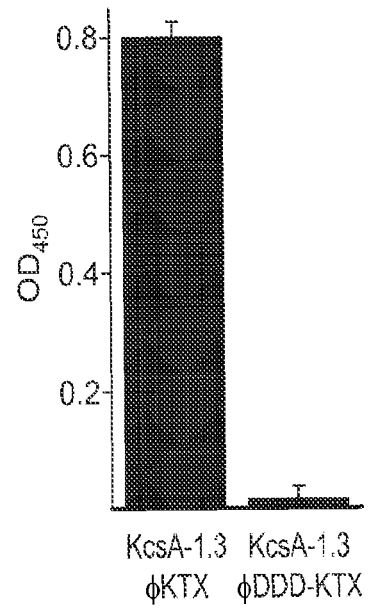

As shown in the ELISA assay of FIG. 6, KTX is able to express, fold and bind adequately when exposed on the phage surface as a fusion partner with protein III. KTX-phages bind to a purified potassium channel (KcsA carrying a segment of the Kv1.3 pore loop, KcsA-1.3) whereas KTX-phage did not bind to wild KcsA nor did DDD-KTX-phage bind to either KcsA-1.3 or KcsA. The data represented in FIG. 6 is the mean and S.E. recorded from 3 wells. "A" shows Kaliotoxin-1 phage (fKTX) binds to KcsA-Kv1.3 but not to wild-type KcsA. "B" shows Inactive kaliotoxin-1 (R24D, K27D, R31D; fDDD-KTX) does not bind to KcsA-1.3.

To demonstrate KTX-phages inhibit Kv1.3 channels, Kv1.3 channels expressed in human embryonic kidney cells (HEK293) were studied using whole-cell patch-clamp. Phagemids were applied at 1 nM and then washed out. Half recovery was achieved at ~3 min wash time. Plasmids were transfected into cells with Lipofectamine 2000 (Invitrogen) according to the manufacturer's instructions. Experiments were performed at 24 hr. Whole-cell patch-clamp was performed using an Axopatch 200B amplifier and pCLAMP software (Molecular Devices, Union City, Calif.) at filter and sampling frequencies of 5 and 25 kHz respectively. Kv1.3 currents were evoked by 250 ms test pulses to 50 mV from −80 mV with a 5 second interpulse interval and studied in a bath solution comprising in mM: 1.3 $CaCl_2$, 0.5 $MgCl_2$, 0.4 $MgSO_4$, 3.56 KCl, 0.44 $KH_2PO_4$, 139.7 NaCl, 0.34 $Na_2HPO_4$, 5.5 glucose, 10 HEPES adjusted to pH 7.4 with NaOH. Electrodes were fabricated from borosilicate glass (Clark, Kent, UK) and had a resistance of ~5 MS2 when filled with a solution containing in mM: 136 KCl, 1 $MgCl_2$, 2 $K_2ATP$, 5 EGTA, 10 HEPES adjusted to pH 7.2 with KOH. Electrodes were coated with Sigmacote (Sigma) prior to use.

Figure 7:
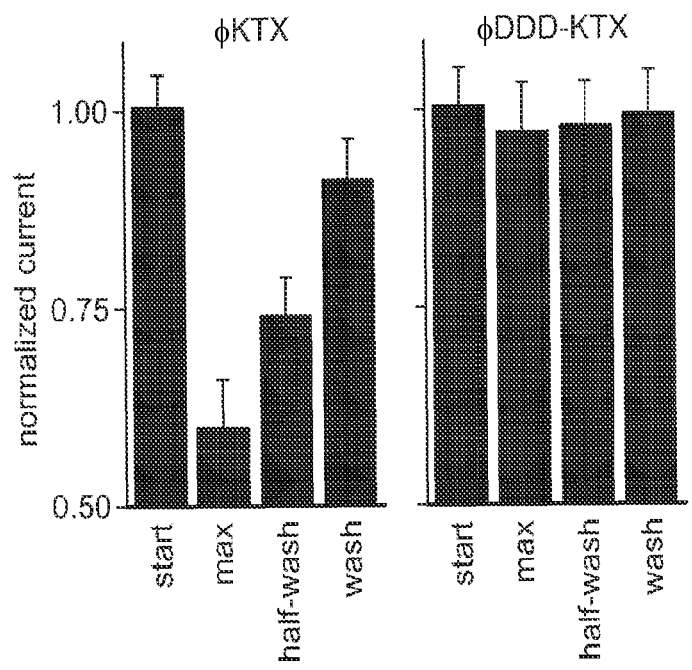
FIG. 7 is a set of graphs depicting KTX-phage inhibition of Kv1.3 channels expressed in HEK293 cells.

As shown in FIG. 7, KTX-phage inhibits Kv1.3 channels. Application of 1 nM KTX-phage blocked currents by ~35% and inhibition was reversed by half in ~20 minutes on washing the cells with buffer without phage particles. Conversely, DDD-KTX-phage, phage expressing camel CVHH antibody fragments to an unrelated antigen or buffer used for the phage preparation did not suppress or augment channel currents.

A phage-display library of the novel toxin scaffolds was designed based on the KTX family of scaffolds (FIG. 8). Thirty-six (36) known KTX family toxin sequences were aligned using the six conserved cysteine residues they employ to form three disulfide bonds. The sequences were thereby considered in three linear domains homologous to KTX residues G1-P12 (domain A), L15-G26 (domain B) and N30 to K38 (domain C). Toxins were then constructed from one linkage of one of 30 unique A domains, 22 unique B domains and 17 unique C domains present in the 32 parent toxins. Forward and reverse primers were synthesized for each 69 unique domains, phosphorylated and annealed. Ninety separate reactions were used to anneal domains (in each reaction was 1 A domain, 7 or 8 B domains, and 17 C domains in equimolar proportions). These were ligated into pAS62 phagemids and transfected into XL1 *E. coli*. Joining sequences between AB and BC were shared sites (in KTX these are Q13C14 and K27T28M29) leading to a calculated library diversity of 11,220 toxin variants including the 19 known toxins. Random genotyping of isolates confirmed expression of all domains and 68% toxin-bearing phage.

The library was applied to KcsA-1.3 immobilized onto a solid-phase. Following two rounds of panning, 16.6% of the eluted phage was a single novel neurotoxin-like sequence composed of A, B and C domains from three different species of scorpions, shown in FIG. 9: *Buthus occitanus* (AgTx2, domain A, North Africa), *Centruroides elegans* (Ce3, domain B, Central America), and *Leiurus quinquestriatus* (charybdotoxin, domain C, Middle East). The new toxin was named mokatoxin-1 (MK-1) and was not observed in control selective trials with KcsA.

To confirm that isolation of MK-1 was specific, a 1:15,000 mixture of mokatoxin-1-phage and DDD-KTX-phage was applied to immobilized KcsA-1.3. Sixty percent of the phage isolated after two rounds of selection was MK-1 while all isolates recovered after two rounds on the KcsA control were DDD-KTX.

MK-1-phage particles were confirmed to bind specifically to KcsA-1.3 and also block Kv1.3 currents in mammalian cells. Thereafter, MK-1 was synthesized. As depicted in FIG. 10, application of the MK-1 to wild-type Kv1.3 channels expressed in *Xenopus* oocytes showed half-maximal blockade at 3 nM. The blocking of Kv.13 by MK-1 is represented by filled circles; the blocking of Kv1.2 by MK-1 is represented by filled diamonds; and the blocking of Kv1.1 by MK-1 is represented by filled triangles.

Notably, as shown in Table 8, the pharmacological profile of mokatoxin-1 (MK-1) was different than all three of its parent toxins and KTX. Whereas MK-1 blocks only Kv1.3 potently, KTX blocks Kv1.1, Kv1.2, Kv1.3 and BK, AgTx2 blocks Kv1.1 and Kv1.3, Ce3 does not block Kv1.3 and CTX blocks Kv1.2, Kv1.3 and BK.

The demonstrated selectivity of MK-1 on Kv1.3 in respect of other K+ channels is one significant example of the power and utilization potential of the present method describing the creation of toxin libraries and their screening. Pharmacological selectivity (specificity) is one example of useful modifications (e.g., improving on existing toxins or toxin scaffolds) such residue alterations to improve target specificity, affinity, impact on receptor function, to attach cargo for delivery to specific cellular and molecular locations and/or similar new/useful properties.

TABLE 8

| Toxin | Channel approximate IC50 (nM) | | | |
|---|---|---|---|---|
| | Kv1.1 | Kv1.2 | Kv1.3 | BK |
| MK-1 | >1000 | ~680 | ~3 | >1000 |
| KTX-1 | 0.1 | 1.4 | 0.5 | ~5 |
| AgTX2 | 0.04 | 26.8 | 0.004 | ~1150 |
| Ce3 | ND | ND | ~366 | ND |
| CTX | 1500 | 5.6 | 2.5 | 3 |

Example 9

Kaliotoxin-1-Phage Specifically Binds to and Enriched on Animal Cells Expressing Functional Mammalian Wild-Type K+ Channel Kv1.3

HEK cells were transfected with an expression vector carrying K' channel Kv1.3 (TEST) or with empty vector that does not code for any transmembrane protein (CONTROL). Transfection efficiency was monitored with cotransfection of gene encoding for the green fluorescence protein (GFP) and observing the fluorescence after 1-2 days following transfection. Under these conditions, functional expression of the Kv1.3 channel was verified by electrophysiological, biochemical, and immunological means.

At the peak expression time for Kv1.3 channels (1-2 days following transfection), cells were detached from the monolayer, washed and brought into contact with a calculated mixture of 2% KTX-phage:2% mokatoxin-1-phage:96% inactive kaliotoxin-1 (DDD-KTX)-phage. KTX and mokatoxin-1 are Kv1.3 specific scorpion toxins. DDD-KTX is a mutant variant of KTX that does not bind to or inhibit Kv1.3 channels. Following incubation of the cells with the phages, cells were subjected to wash to remove the unbound/weakly bound phages. The remaining bound phages were eluted from the cells and transformed into XL1 *E. coli*, and plated onto LB plates with antibiotic selecting for the phagemids. After 1 day, 16-20 colonies of transformed XL1 were randomly selected and genotyped to establish the relative ratio (i.e., its departure from the calculated initial input of 2:2:96%) of the three different phage species, before and after the 1st and 2nd rounds of panning Kv1.3 specific KTX-phage was enriched from a calculated initial input of 2% to 40% (n=20) after the 2nd panning on Kv1.3 expressing cells, but not on vector transfected cells. In addition, Kv1.3 specific mokatoxin-1-phage was enriched from a calculated initial input of 2% (n=20) to 15% (n=20) after the 2nd panning on Kv1.3 expressing cells, but not on vector transfected cells. DDD-KTX-phage proportion decreased in the Kv1.3 expressing cells, while in the vector transfected cells, after the 2nd panning, this was the only species recovered in our sample (n=16).

Example 10

Isolation of Mokatoxin_0422, a Novel K+ Channel Toxin, from a Toxin Phage-Display Library by Panning on Kv1.3 K+ Channels Expressed in Mammalian Cells HEK cells were transfected with an expression vector carrying K+ channel Kv1.3 (TEST) or with empty vector that does not code for any transmembrane protein (CONTROL). Transfection efficiency was monitored by observing fluorescence after 1-2 days following cotransfection of a gene encoding for the green fluorescence protein (GFP). Under these conditions, functional expression of the Kv1.3 channel was verified by electrophysiological, biochemical, and immunological means.

At the peak expression time for Kv1.3 channels (1-2 days following transfection), cells were detached from the monolayer, washed and brought into contact with $\sim 3 \times 10^{11}$ phages of a KTX scaffold combinatorial library. The KTX scaffold combinatorial library construction comprises a phage-display library of novel toxin scaffolds designed based on the KTX family of scaffolds. Thirty-six known KTX family toxin sequences were aligned using the six conserved cysteine residues employed by KTX to form three disulfide bonds. The sequences were thereby considered in three linear domains homologous to KTX residues G1-P12 (domain A), L15-G26 (domain B) and N30 to K38 (domain C). Toxins were then constructed from one linkage of one of 30 unique A domains, 22 unique B domains and 17 unique C domains present in the 32 parent toxins. Joining sequences between AB and BC were shared sites (in KTX these are Q13C14 and K27T28M29) leading to a calculated library diversity of 11,220 toxin variants including the 19 known toxins. One such toxin is mokatoxin 0422, whose amino acid sequence TVIDVKCTSPKQ-CLPPCKAQFGIRAGAKCMNKKC RCYS (SEQ ID NO: 2) is depicted in FIG. 9. Random genotyping of isolates confirmed expression of all domains and 58.3% (n=120) toxin-bearing phage.

Following incubation of the cells with the phages, cells were subjected to wash to remove the unbound/weakly bound phages. The remaining bound phages were eluted from the cells and transformed into XL1 *E. coli*. Transformed XL1 was (1) amplified overnight in liquid media in the presence of a helper phage and antibiotic to prepare a phage preparation (to used in subsequent rounds of panning), and (2) an aliquot of the transformed XL1 was plated onto LB plates with antibiotic selecting for the phagemid. The following day, 18-20 colonies of the plated XL1 were randomly selected and genotyped to establish enrichment on Kv1.3 cells versus control cells not expressing Kv1.3.

Electrophysiological recordings were performed with mokatoxin_0422 to confirm blocking of Kv1.3 channels. Phagemids were applied at 1 nM mokatoxin_0422-displaying phage concentration and then washed out. Half recovery was achieved at ~3 min wash time. Plasmids were transfected into cells with Lipofectamine 2000 (Invitrogen) according to the manufacturer's instructions. Experiments were performed at 24 hrs. Whole-cell patch-clamp was performed using an Axopatch 200B amplifier and pCLAMP software (Molecular Devices, Union City, Calif.) at filter and sampling frequencies of 5 and 25 kHz respectively. Kv1.3 currents were evoked by 250 ms test pulses to 50 mV from −80 mV with a 5 second interpulse interval and studied in a bath solution comprising, in mM: 1.3 $CaCl_2$, 0.5 $MgCl_2$, 0.4 $MgSO_4$, 3.56 KCl, 0.44 $KH_2PO_4$, 139.7 NaCl, 0.34 $Na_2HPO_4$, 5.5 glucose, 10 HEPES adjusted to pH 7.4 with NaOH. Electrodes were fabricated from borosilicate glass (Clark, Kent, UK) and had a resistance of ~5 MΩ when filled with a solution containing in mM: 136 KCl, 1 $MgCl_2$, 2 $K_2ATP$, 5 EGTA, 10 HEPES adjusted to pH 7.2 with KOH. Electrodes were coated with Sigmacote (Sigma) prior to use.

Following the 1st round of panning, no toxin showed signs of enrichment (n=20). Following the 2nd round of panning, mokatoxin_0422 appeared at 11% (n=18), while all other toxins appeared only once in the sample (i.e., no indication of enrichment). Electrophysiological recording at 0.1 nM mokatoxin 0422-displaying phage concentration, shown in FIG. 12, confirmed that mokatoxin_0422 blocks Kv1.3 channels expressed in mammalian cells. The control, DDD-kaliotoxin-1 phage (kaliotoxin-1 in which the binding sited are eliminated), did not inhibit Kv1.3 current in this system.

Example 11

Verification that Mokatoxin_0422 is Specifically Enriched on Cells Expressing Kv1.3 Channels HEK cells were transfected with an expression vector carrying $K^+$ channel Kv1.3 (TEST) or with empty vector that does not code for any transmembrane protein (CONTROL Transfection efficiency was monitored by observing fluorescence after 1-2 days following cotransfection of a gene encoding for the green fluorescence protein (GFP). Under these conditions, functional expression of the Kv1.3 channel was verified by electrophysiological, biochemical, and immunological means. At the peak expression time for Kv1.3 channels (1-2 days following transfection), cells were detached from the monolayer, washed and brought into contact with a calculated mixture of 5% mokatoxin_0422-phage:95% inactive kaliotoxin-1 (DDD-KTX)-phage.

As described above, mokatoxin_0422 is a Kv1.3 specific scorpion toxin isolated from a scorpion-toxin phage display library, while DDD-KTX is a mutant variant of kaliotoxin-1 that does not bind to or inhibit Kv1.3 channels. Following incubation of the cells with the phages, cells were subjected to wash to remove the unbound/weakly bound phages. The remaining bound phages were eluted from the cells and transformed into XL1 *E. coli*, and plated onto LB plates with antibiotic selecting for the phagemids. The following day, 19-20 colonies of transformed XL1 were randomly selected and genotyped to establish the relative ratio (i.e., its departure from the calculated initial input of 5:95%) of the two different phage species, before and after the panning.

As shown in Table 9, Kv1.3 specific mokatoxin 0422-phage enriched from a calculated initial input of 5% (measured input of mokatoxin 0422-phage was 0% in a n=20 sample) to a measured 90% (n=20) after the one round of panning on Kv1.3 expressing cells, but not on vector transfected cells.

TABLE 9

| | | # of genotype ( %) | | |
|---|---|---|---|---|
| | Calculated (%) | Input | Test | Control |
| mokatoxin_0422 | 5 | 0 (0) | 18 (90) | 1 (5) |
| DDD-KTX | 95 | 20 (100) | 2 (10) | 18 (95) |
| Total | 100% | 20 (100) | 20 (100) | 19 (100) |

Example 12

Functional Expression of Sea Anemone Animal Toxin Scaffold on the Phage and Specific Selection Sea anemone K' channel toxin (ShK) was expressed in a phage display. As shown in Table 10, Shk phage is enriched on a target KcsA-1.3 but not in KcsA. The target KcsA-1.3 contains a receptor domain for Shk from $K^+$ channel Kv1.3.

TABLE 10

| | % phages (n = 17-20) | | | |
|---|---|---|---|---|
| | INPUT | | OUTPUT | |
| phage | calculated | actual | KcsA-1.3 | KcsA |
| Shk | 1 | 0 | 20 | 0 |
| Camel VHH | 99 | 100 | 0 | 80 |

As shown in FIG. 13, Shk expressed on the phage (Shk) blocks Kv1.3 current in mammalian cells, confirming that the animal toxin is functionally expressed. Control phage (Ctrl) expressing a nonspecific ligand has no effect on the current.

Example 13

Mokatoxin-1 is Selective Among Potassium Channels

Mokatoxin-1 was selected for its high affinity for Kv1.3. This toxin peptide has a large difference in affinity for other channels that are important targets for the kaliotoxin scaffold. Mokatoxin-1 is unique as compared to known natural toxins and their natural or point mutant homologs.

To examine the effect of mokatoxin-1 on activity of potassium ion channels, cDNA encoding *Rattus* Kv1.1 (NCBI accession number NM_173095), *Rattus* Kv1.2 (NM_012970), Homo Kv1.3 (NM_002232), or *Mus* BK (NM_010610) were subcloned into oocyte expression vectors based on PCR3.1 and pGEM. cRNA synthesis was performed with T7 polymerase and the mMessageMachine Kit (Ambion, Austin, Tex.) according to manufacturers instructions. cRNA concentrations were determined spectroscopically. For two electrode voltage clamp recordings oocytes were extracted from *Xenopus laevis* and defoliculated with Collagenase Type 2 (Worthington, Lakewood, N.J.). Oocytes were maintained in ND91 solution containing 2 mM KCl, 91 mM NaCl, 1 mM $MgCl_2$, 1.8 mM $CaCl_2$, and 5 mM HEPES, pH 7.5, supplemented with 1% Penicillin/Streptomycin (Cellgro, Herndon, Va.) and 0.1% Gentamycin sulfate (Gibco, Grand Island, N.Y.)) at 16° C. Stage V and VI oocytes were injected with 8 pg to 4 ng cRNA, and currents recorded 1 to 4 days later.

For dose-response measurements of toxin block of Kv1.1, Kv1,2, or Kv1.3 peak currents were recorded during a 500 ms step to 0 mV from a holding voltage of −100 mV, followed by a 200 ms step to −135 mV every 30 s. To determine the kinetics of toxin block oocytes were held at −100 mV and stepped to the test voltage of 0 mV for 100 ms followed by a 200 ms duration step to −135 mV every 2 s. BK currents were recorded during a 50 ms step to +60 mV from a holding voltage of −80 mV, followed by a 40 ms step to −100 mV every 3 s. The perfusion solution contained 2 mM KCl, 96 mM NaCl, 1 mM $MgCl_2$, 1.8 mM $CaCl_2$, 5 mM HEPES, pH 7.5 and 0.1% fatty acid ultra-free BSA fraction V (Roche Diagnostics Corporation, Indianapolis, Ind.). Data acquisition and processing was performed with an oocyte clamp OC-725B (Warner Instruments Corporation, Hamden, Conn.), pCLAMP (Axon, Sunnyvale, Calif.), IGOR Pro (WaveMetrics, Lake Oswego, Oreg.), and Origin6.1 (Origin-Lab Corporation, Northampton, Mass.) softwares. The equilibrium dissociation rates ($K_D$) for block of Kv1.1, Kv1.2, and Kv1.3 by mokatoxin-1 were determined by fitting the dose-response data and $k_{on}$ and $k_{off}$ were calculated as described by Goldstein and Miller, 1993 (Biophys J. 1993 65 (4):1613-1619).

Figure 16:
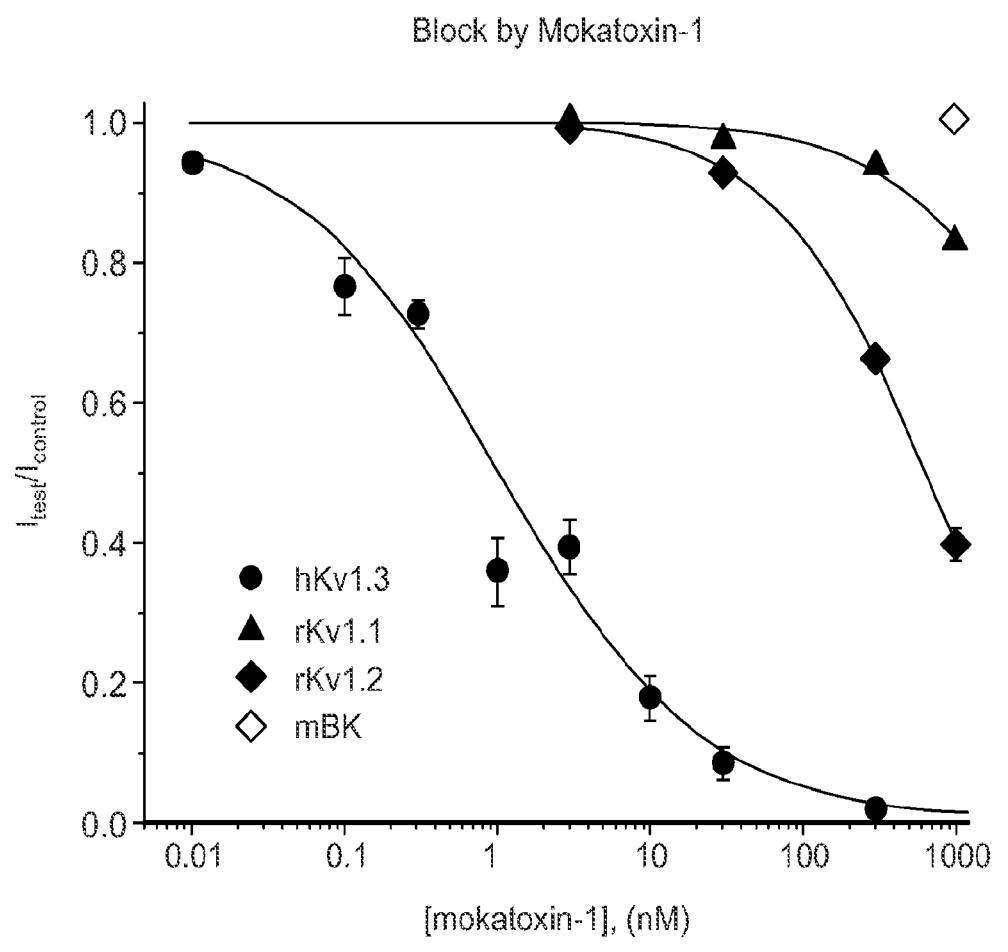

FIG. 16 and Table 11 show the dose-response relationship of mokatoxin-1 on different K channels: human (h) Kv1.1, Kv1.2, Kv1.3, and mouse (m) big conductance calcium-activated K channel. The graph shows that mokatoxin-1 is specific (selective) for Kv1.3 and has a high affinity.

IL-2, IFN-γ and TNF-α Secretion Assays $10^5$ freshly isolated CD3' T cells were activated using CD3/CD28 dynabeads (Dynal, USA) at a T cell:bead ratio of 1:1 in 200 ul of medium in 96 wells plate. Channel blockers diluted at different concentrations in PBS were added to the cells 1 h prior to stimulation (done in triplicate). After 16 h of activation cells were counted and supernatants analysed for hIL-2, hIFN-γ and hTNF-α by ELISA following the manufacturer's instructions (eBiosciences, San Diego, Calif., USA).

Results: MK Toxin Inhibits Secretion of IL-2, IFN-γ and TNF-α by CD3/CD28 Activated T Cells Block of the $K^+$ channels in T cells by mokatoxin-1 decreased immune functions including IL-2 and IFN-γ secretion after CD3/CD28 stimulation. Human CD3' T cells were stimulated with CD3/CD28 beads following incubation with different concentrations (from 0.1 to 100 nM) of MK and KTX. The activity of MK was compared to the activity of KTX that was previously described to block the channels (Beeton et al, JI 2001). FIG. 17 shows that MK inhibits at concentration as low as 1 nM. At a concentration of 10 nM, IL-2 and TNF-α secretion were decreased by approximately 50%; there was no reduction of cell viability with concentrations as high as 1 μM (not shown). The data show that inhibition of cytokine secretion by MK was comparable to, or better than that seen with KTX.

Examples 15

Mokatoxin-1 Does not Alter Ileum Function

Kaliotoxin and related toxins block Kv1.1 and produce ileal contractions. In contrast, mokatoxin is selective and does not block Kv1.1 or cause ileal hyperactivity.

TABLE 11

| | Mokatoxin-1 | | | AgTx-2 | ChTx | KTX | | |
|---|---|---|---|---|---|---|---|---|
| | $K_{on}$ | | | | | | | |
| Channel | $K_i$ [nM] | $[M \cdot s]^{-1}$ | $K_{off}[s]^{-1}$ | $K_i$ [nM] | $K_i$ [nM] | $K_i$ [nM] | $K_{on} [M \cdot s]^{-1}$ | $K_{off}[s]^{-1}$ |
| $rK_v1.1$ | >>1 μM | ND | ND | 0.17 ± 0.03 | >>1 μM | 1.1 ± 0.5 | $30 \cdot 10^6 \pm 16 \cdot 10^6$ | 0.009 ± 0.002 |
| $rK_v1.2$ | 620 ± 60 | $0.26 \cdot 10^6 \pm 0.06 \cdot 10^6$ | 0.16 ± 0.03 | 3.4 ± 0.9 | 9 ± 4 | 20 ± 4 | $13 \cdot 10^6 \pm 3 \cdot 10^6$ | 0.21 ± 0.01 |
| $hK_v1.3$ | 1.0 ± 0.1 | $36 \cdot 10^6 \pm 5 \cdot 10^6$ | 0.059 ± 0.007 | 0.041 ± 0.007 | 0.9 ± 0.1 | 0.008 ± 0.001 | $8 \cdot 10^8 \pm 1 \cdot 10^8$ | 0.0070 ± 0.0009 |
| mBK | >>1 μM | N/A | N/A | ND | 5.0 ± 0.8 | 1.6 ± 0.1 | $21 \cdot 10^3 \pm 4 \cdot 10^3$ | 0.0211 ± 0.0008 |

Example 14

Mokatoxin-1 Inhibits Human T Cell Function

Figure 18A:
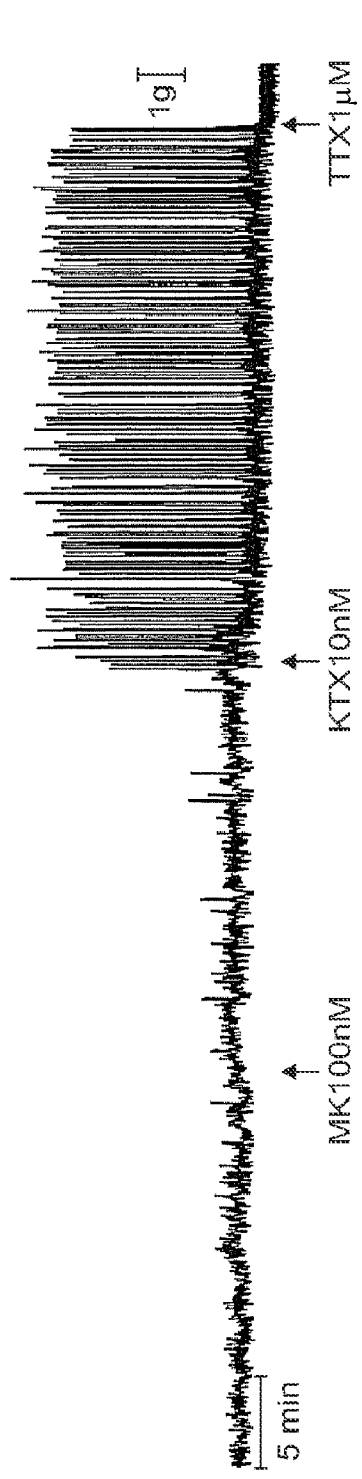
FIGS. 18A and 18B are a set of graphs showing the selectivity of mokatoxin-1 for Kv1.3 K$^+$ channel subtype. (A) Kaliotoxin (KTX) at 10 nM, but not mokatoxin-1 (tested: 1-100 nM, shown: 100 nM), induced twitches in the ileum strips. (B) The classical kaliotoxin homolog margatoxin (MgTX) at 10 nM, but not mokatoxin-1 (tested: 1-100 nM, shown: 100 nM), induced a lowering of the pressure threshold for initiation of the peristaltic waves and an increase the frequency of these waves.
Figure 18B:
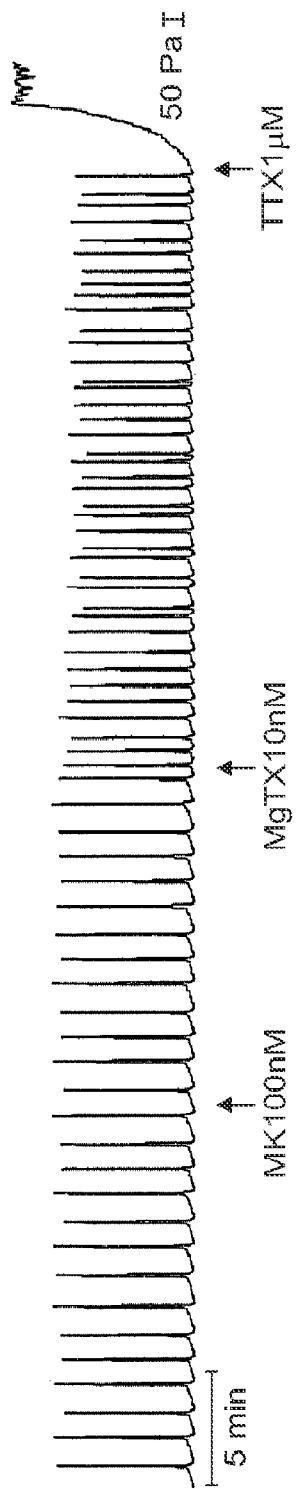

Blocking the Kv1.3 channel in T cells suppresses immune responses. Data in this example show that mokatoxin-1 blocks T cell activity at least as well as kaliotoxin. Experiments in this example were performed as described in 2008, J. Biol. Chem. 283, 14559-14570.

Isolation and Culture of Human T Cells

Human T cells purified from peripheral blood of healthy donors. Peripheral blood mononuclear cells were separated by centrifugation over Ficoll-Hypaque for 15 min. This step was followed by negative magnetic cell purification according to the manufacturer's instructions (Human Pan T cells isolation kit, Miltenyi Biotec Inc., Auburn, Calif., USA) and purity of $CD3^+$ T cells was >96% as assessed by flow cytometry. Cells were maintained in RPMI 1640 medium supplemented with 10% FCS, penicillin, streptomycin, MOPS, 2-ME, and nonessential amino acids in a 5% $CO_2$ incubator at 37° C.

To show the selectivity of mokatoxin-1 for Kv1.3 $K^+$ channel subtype and to further demonstrate the pharmaceutical utility of mokatoxin-1, experiments were performed as described in Suarez-Kurtz et al., J Pharmacol Exp Ther. 289 (3):1517-1222, 1999. These experiments use the spontaneous motility of guinea pig ileum as an organ-level assay to demonstrate $K^+$ channel subtype specificity. The effect of Kv1.1 or Kv1.2 blockers is to induce spontaneous twitches.

In addition, experiments were performed as described in Vianna-Jorge et al., Br J. Pharmacol. 2003, 138 (1):57-62. These experiments assay the intraluminal pressure measurements of peristaltic activity of guinea pig ileum as an organ-level assay to demonstrate $K^+$ channel subtype specificity. The effect of Kv1.1 or Kv1.2 blockers is to lower the pressure threshold for initiation of the peristaltic waves and increase the frequency of these waves.

The classical kaliotoxin homolog Margatoxin at 10 nM, but not mokatoxin-1 (1-100 nM), induced twitches in the ileum strips (FIG. 18A). This is an effect mediated by Kv1.1 consistent with selectivity of mokatoxin-1 for Kv1.3 channels (not in ileum). Margatoxin, but not mokatoxin-1 induced a lowering of the pressure threshold for initiation of the peristaltic waves and an increase in the frequency of these waves (FIG. 18B). Ileum has Kv1.1 and Kv1.2 channels and block of either leads to contractions (as seen with all three toxins, margatoxin and kaliotoxin and agitoxin-2, J Pharmacol Exp Ther. 1999, 289 (3):1517-1222). The effect by mokatoxin-1 on T cells but not ileum shows that it blocks Kv1.3 but not Kv1.1 or Kv1.2 channels in native tissues.

Example 16

Mokatoxin-1 Structure is Novel

To understand the basis for selectivity the three dimensional structure of mokatoxin, the structure was solved by solution NMR by the method described in Koide et al., J Mol. Biol. 284 (4):1141-1151, 1998; and Karatan et al., Chem. Biol. 2004, 11 (6):835-844, 2004. This analysis revealed that mokatoxin-1 and kaliotoxin-1 have similar, but not identical, scaffold structure as expected by the constraints of library design.

Example 17

Mokatoxin-2 and mokatoxin-3: Kv Channel Blockers Selected on Cells with Novel Characteristics Mokatoxin-2 and -3 were isolated from a library using cell-based panning where CHO cells were induced to produce intact human Kv1.3 channels on their surfaces. (By contrast, mokatoxin-1 was isolated on purified proteins in plastic dishes). These novel toxins are based on sequences found in the kaliotoxin family and exhibit different kinetics of inhibition compared to kaliotoxin-1, on which the library was designed, and to mokatoxin-1, a toxin peptide isolated using solid-phase panning. The amino acid sequences of mokatoxin-2 and mokatoxin-3 are as follows:

```
mokatoxin-2 (also known as mokatoxin_0422):
                                   (SEQ ID NO: 77)
TVIDVKCTSPKQCLPPCKAQFGIRAGAKCMNKKCRCYS mokatoxin-3 (also known as mokatoxin_0516):
                                   (SEQ ID NO: 78)
TVIDVKCTSPKQCLPPCKAQFGIRAGAKCMNKKCRCYS
```

Figure 20:
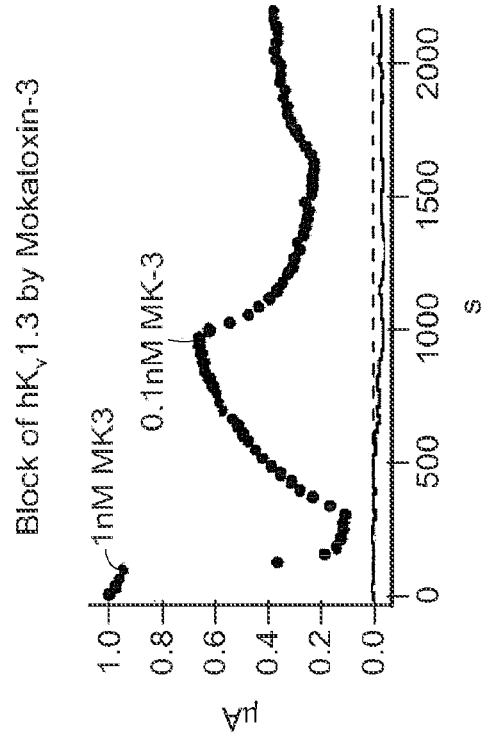
FIG. 20 is a graph showing the kinetics of inhibition of hKv1.3 by mokatoxin-3.
Figure 19:
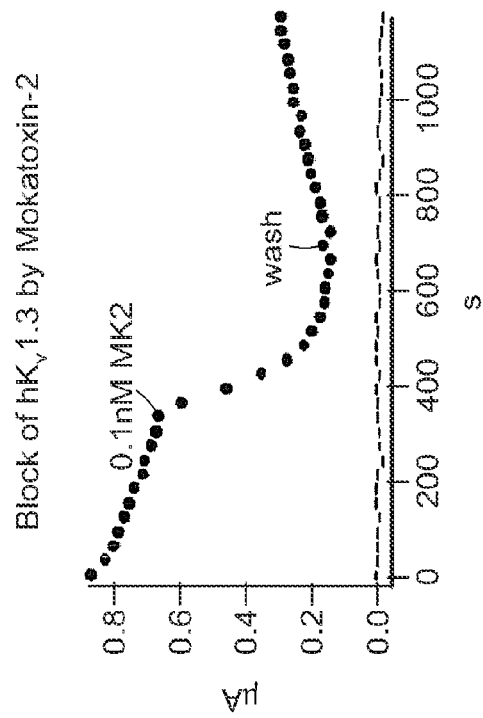
FIG. 19 is a graph showing the kinetics of inhibition of hKv1.3 by mokatoxin-2.

To determine the kinetics of toxin block by these toxin peptides, oocytes were held at −100 mV and stepped to the test voltage of 0 mV for 100 ms followed by a 200 ms duration step to −135 mV every 2 s. BK currents were recorded during a 50 ms step to +60 mV from a holding voltage of −80 mV, followed by a 40 ms step to −100 mV every 3 s. The perfusion solution contained 2 mM KCl, 96 mM NaCl, 1 mM $MgCl_2$, 1.8 mM $CaCl_2$, 5 mM HEPES, pH 7.5 and 0.1% fatty acid ultra-free BSA fraction V (Roche Diagnostics Corporation, Indianapolis, Ind.). Data acquisition and processing was performed with an oocyte clamp OC-725B (Warner Instruments Corporation, Hamden, Conn.), pCLAMP (Axon, Sunnyvale, Calif.), IGOR Pro (WaveMetrics, Lake Oswego, Oreg.), and Origin6.1 (OriginLab Corporation, Northampton, Mass.) softwares. The equilibrium dissociation rates ($K_D$) for block of Kv1.1, Kv1.2, and Kv1.3 by mokatoxins were determined by fitting the dose-response data and $k_{on}$ and $k_{off}$ were calculated as described by Goldstein and Miller, 1993 (Biophys J. 1993 65 (4):1613-1619). The results are shown in FIGS. 19 and 20.

Example 18

Phage Selection on Cells Allows for Screening of High Diversity Libraries

After three rounds of panning, kaliotoxin-1-phage were recovered at 58% of recovered phage despite infrequent representation in the library. Phage expressing DDD-kaliotoxin, which is a mutant toxin that does not bind to KTX sites, do not bind to the channels. The data in Table 12 show enrichment of kaliotoxin-1-phage (1 out of $10^{10}$ phage) on Kv1.3 channels expressed in HEK cells. This shows the utility of this technique to select a highly diverse (e.g., $10^{10}$ or greater) library.

TABLE 12

| phage | input proportion | 1st round | 2nd round (n = 20) % | 3rd round (n = 12) % |
|---|---|---|---|---|
| kaliotoxin-1 | 0.0000000001 | N.D. | 0 | 58 |
| DDD-kaliotoxin-1 | 0.9999999999 | N.D. | 100 | 42 |

Example 19

Toxins with Posttranslational Modifications and Generation of Diversity

As described herein, libraries of ligands can be generated to include variation by virtue of combinatorial diversity (e.g, by joining portions of different toxins to create novel toxin peptide sequences) or sequence alterations. In some embodiments, diversity is generated by varying residues that undergo posttranslational modification.

Conus Geographus GIIIA Libraries

This library is constructed using the marine cone snail *Conus geographus* GIIIA toxin as the scaffold. This toxin has amino acids that undergo postranslational modification in the snail (hydroxyproline, O). In this example, residues that undergo postranslational modification are mutated alone and in combination with other residues that are hypothesized to govern biological function to create lead toxins. Three example libraries and their resulting diversities are shown in Table 13:
\* important for binding, based on literature and our own prediction
- no effect on binding, based on literature and our own prediction

TABLE 13

```
       Conus geographus GIIIA Libraries

RDCCTOOKKCKDRQCKOQRCCA* native toxin
(SEQ ID NO: 79)
           *  *  *
       -      *
       -    -**  *
            *   *
            *   **
            *
       * *      *
0000000001111111111222  GIIIA residues
1234567890123456789012  GIIIA residues
.....123456789012.....  mutagenesis residues RDCCTPPKKCKDRQCKPQRCCA    (SEQ ID NO: 80)
-----XX---------X-----
X = any amino acid except C
```

TABLE 13-continued

Conus geographus GIIIA Libraries

```
library 1:
diversity: approx. 19exp3
RDCCTPPKKCKDRQCKPQRCCA    (SEQ ID NO: 80)
-----XX---------X----- library 2:
diversity: approx. 185,193
RDCCTPPKKCKDRQCKPQRCCA    (SEQ ID NO: 80)
-----XX-----H--RX-K---
     K     H   H library 3:
diversity: approx. 6.68 x 10exp7
RDCCTPPKKCKDRQCKPQRCCA    (SEQ ID NO: 80)
-----XX-----HX-RXXK---
     K     H   H
```

RDCCTOOKKCKDRQCKOQRCCA corresponds to SEQ ID NO: 79.

Example 20

Representative Random Change Libraries

Shk-Scaffold Sea Anemone Library with Natural Variation at Key Sites

This library is constructed using Shk as the scaffold representative toxin. All Shk scaffold member sequences are extracted from databases, literature, and related sources and aligned according to the disulfide bonds. In this example, only those Shk scaffold members are used where the number of amino acids between any of two neighboring cysteine residues exactly match the number in Shk. Then a library design with a calculated diversity of 7.776000e+07 is produced. Other strategies include use of representative residues for classes of amino acids, full randomization, etc.

```
Master Peptide:
P29187/3-35              =RSCIDTIPKSRCTAFQCKHSMKYRLSFCRKTCGTC (SEQ ID NO: 81)

Homologs:
HmK (Heteractis magnifica) =RTCKDLIPVSECTDIRCRTSMKYRLNLCRKTCGSC (SEQ ID NO: 82)

(Heteractis magnifica)   =RTCKDLMPVSECTDIRCRTSMKYRLNLCRKTCGSC (SEQ ID NO: 83)

AETX K                   =RACKDYLPKSECTQFRCRTSMKYKYTNCKKTCGTC (SEQ ID NO: 84)

Q9TWG1/236               =..CKDNFAAATC....C..........CAKTCGKC (SEQ ID NO: 85)

P81897/236               =..CKDNFSANTC....C..........CAKTCGKC (SEQ ID NO: 86)

P29186/237               =..CRDWFKETAC....C..........CAKTCELC (SEQ ID NO: 87)

Q8I9P4/11-46             =..C........C....C..........CAKTCGFC (SEQ ID NO: 88)

A7SOM3/61-92             =..C........C....C..........CKKTCGTC (SEQ ID NO: 89)

P29187/3-35              =..CIDTIPKSRCTAFQCKHSMKYRLSFCRKTCGTC (SEQ ID NO: 90)

A7S9H4/48-78             =..C........C....C..........CMKMCGLC (SEQ ID NO: 91)

P11495/4-36              =..C........C....C..........CEKTC..C (SEQ ID NO: 92)

A7T942/60-90             =..C........C....C..........CPKKCKYC (SEQ ID NO: 93)

A7RS52/223-257           =..C........C....C..........CKKTCGHC (SEQ ID NO: 94)

A7S9H4/283-313           =..C........C....C..........CPKKCGLC (SEQ ID NO: 95)

A7RRU4/414-447           =..C........C....C..........CPRSCDYC (SEQ ID NO: 96)

Q2MCX7/232-262           =..C........C....C..........CKKKCKLC (SEQ ID NO: 97)

A7SMA6/73-119            =..C........C....C..........CAKTCGMC (SEQ ID NO: 98)

A7T942/24-55             =..C........C....C..........CPKMCNYC (SEQ ID NO: 99)

A7RW59/220-250           =..C........C....C..........CRKTCSLC (SEQ ID NO: 100)

A7RW59/251-281           =..C........C....C..........CRKTCSLC (SEQ ID NO: 101)

Q9TWG1/2-36              =..CKDNFAAATC....C..........CAKTCGKC (SEQ ID NO: 102)

A7RZH9/186-226           =..C........C....C..........CAKTCGIC (SEQ ID NO: 103)

A7T942/94-125            =..C........C....C..........CKKSCARC (SEQ ID NO: 104)

Q9XZG0/458-496           =..C........C....CVSEEKTMKLYCRKTCNFC (SEQ ID -: 105)

Q0MWV8/47-84             =..CSDRAHGHIC....C..........CKKTCGLC (SEQ ID NO: 106)

P81897/2-36              =..CKDNFSANTC....C..........CAKTCGKC (SEQ ID NO: 107)

A7SQ19/39-74             =..C........C....CRTNPKWMAKYCRKSCGTC (SEQ ID NO: 108)
```

```
Q2MCX7/267-303      =..C........C....C..........CKRSCGLC   (SEQ ID NO: 109)

A7RMG1/3-35         =..C........C....C..........CQKSCDLC   (SEQ ID NO: 110)

A7RFK7/159-199      =..C........C....C..........CPETCGFC   (SEQ ID NO: 111)

A7RU87/237-269      =..C........C....C..........CKRSCKLC   (SEQ ID NO: 112)

P29186/2-37         =..CRDWFKETAC....C..........CAKTCELC   (SEQ ID NO: 113)

A7RNX2/29-63        =..C........C....CNKNPKWMLEHCRQSCGQC   (SEQ ID NO: 114)

A7RLA1/399-441      =..C........C....C..........CAKTCGYC   (SEQ ID NO: 115)

A7TC20/77-112       =..C........C....C..........CPKSCGIC   (SEQ ID NO: 116)

A7RVH8/171-211      =..C........C....C..........CLKSCGFC   (SEQ ID NO: 117)

A7SQK9/888-924      =..C........C....C..........CAYTCDTC   (SEQ ID NO: 118)

A7SCA9/62-99        =..C........C....C..........CGAACGLC   (SEQ ID NO: 119)

A7TC20/115-155      =..C........C....CQRNTKWMFHYCPVSCGIC   (SEQ ID NO: 120)

A7SMA5/494-532      =..C........C....C..........CKMTCNLC   (SEQ ID NO: 121)

A7SQK7/412-448      =..C........C....C..........CAYTCDTC   (SEQ ID NO: 122)

A7SY30/36-70        =..C........C....CTRNVKFMLDKCWRSCSGC   (SEQ ID NO: 123)

A7SKD2/68-105       =..C........C....C..........CAKSCAFC   (SEQ ID NO: 124)

A7SME3/290-326      =..C........C....C..........CRKTCSHC   (SEQ ID NO: 125)

Q9U4X9/193-232      =..C........C....C..........C...CKSC   (SEQ ID NO: 126)

A7T0S0/224-261      =..C........C....C..........CPKSCRMC   (SEQ ID NO: 127)

A7T1T5/33-71        =..C........C....C..........CQAACEIC   (SEQ ID NO: 128)

A7SV31/449-488      =..C........C....C..........CRRSCGSC   (SEQ ID NO: 129)

A7T7G9/127-163      =..C........C....C..........CKKSCNLC   (SEQ ID NO: 130)

A7S8T6/69-112       =..C........C....C..........CKKSCNLC   (SEQ ID NO: 131)

0000000000000000000000000000000000000
                    0000000000111111111122222222223333333
                    1234567890123456789012345678901234567

-------------------------------------------------------------------

RSCIDTIPKSRCTAFQCKHSMKYRLSFCRKTCGTC   (SEQ ID NO: 81)

..........E..DIR.RTEE.TKYNL........   (SEQ ID NO: 224)

..........T..Q...VSNP.WMKTN........   (SEQ ID NO: 225)

..........A......NK.T.F.ALY........   (SEQ ID NO: 226)

..........I......QR.V...FKH........   (SEQ ID NO: 227)

.................T.......EK........   (SEQ ID NO: 228)

.........................H.........   (SEQ ID NO: 229)

.........................D.........   (SEQ ID NO: 230)
```

We claim:

1. A peptide comprising an amino acid sequence that is at least 95% identical to SEQ ID NO: 1.

2. A peptide comprising an amino acid sequence that is at least 95% identical to SEQ ID NO: 2.

3. A peptide comprising an amino acid sequence that is at least 95% identical to SEQ ID NO: 3.

4. A pharmaceutical composition comprising the peptide of claim 1.

5. A pharmaceutical composition comprising the peptide of claim 2.

6. A pharmaceutical composition comprising the peptide of claim 3.

* * * * *

UNITED STATES PATENT AND TRADEMARK OFFICE
CERTIFICATE OF CORRECTION

PATENT NO. : 8,716,437 B2
APPLICATION NO. : 12/746410
DATED : May 6, 2014
INVENTOR(S) : Goldstein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 231

<210> SEQ ID NO 1
<211> LENGTH: 34
<212> TYPE: PRT
<213> ORGANISM: Leiurus quinquestriatus

<400> SEQUENCE: 1

Ile Asn Val Lys Cys Ser Leu Pro Gln Gln Cys Ile Lys Pro Cys Lys
1               5                   10                  15

Asp Ala Gly Met Arg Phe Gly Lys Cys Met Asn Lys Lys Cys Arg Cys
            20                  25                  30

Tyr Ser

<210> SEQ ID NO 2
<211> LENGTH: 38
<212> TYPE: PRT
<213> ORGANISM: Leiurus quinquestriatus

<400> SEQUENCE: 2

Thr Val Ile Asp Val Lys Cys Thr Ser Pro Lys Gln C

```
<223> OTHER INFORMATION: Any amino acid and this region may encompass 2-
      20 residues
<220> FEATURE:
<221> NAME/KEY: MOD_RES
<222> LOCATION: (55)..(64)
<223> OTHER INFORMATION: Any amino acid and this region may encompass 2-
      10 residues
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(77)
<223> OTHER INFORMATION: Any amino acid and this region may encompass 0-
      10 residues

<400> SEQUENCE: 4

Xaa Xaa Xaa Xaa Xaa Xaa Xaa Xaa Xaa Xaa Cys Xaa Xaa Xaa Xaa Xaa
1               5                   10                  15

Xaa Xaa Xaa Xaa Xaa Cys Xaa Xaa Xaa Xaa Xaa Xaa Xaa Xaa Xaa
            20                  25                  30

Cys Xaa Xaa Xaa Xaa Xaa Xaa Xaa Xaa Xaa Xaa Xaa Xaa Xaa Xaa
        35                  40                  45

Xaa Xaa Xaa Xaa Xaa Cys Xaa Xaa Xaa Xaa Xaa Xaa Xaa Xaa Xaa
50                  55                  60

Cys Xaa Cys Xaa Xaa Xaa Xaa Xaa Xaa Xaa Xaa Xaa
65              70                  75

<210> SEQ ID NO 5
<211> LENGTH: 82
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(10)
<223> OTHER INFORMATION: Any amino acid and this region may encompass 0-
      10 residues
<220> FEATURE:
<221> NAME/KEY: MOD_RES
<222> LOCATION: (13)..(22)
<223> OTHER INFORMATION: Any amino acid and this region may encompass 2-
      10 residues
<220> FEATURE:
<221> NAME/KEY: MOD_RES
<222> LOCATION: (25)..(34)
<223> OTHER INFORMATION: Any amino acid and this region may encompass 2-
      10 residues
<220> FEATURE:
<221> NAME/KEY: MOD_RES
<222> LOCATION: (37)..(56)
<223> OTHER INFORMATION: Any amino acid and this region may encompass 2-
      20 residues
<220> FEATURE:
<221> NAME/KEY: MOD_RES
<222> LOCATION: (60)..(69)
<223> OTHER INFORMATION: Any amino acid and this region may encompass 2-
      10 residues
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (73)..(82)
<223> OTHER INFORMATION: Any amino acid and this region may encompass 0-
      10 residues

<400> SEQUENCE: 5

Xaa Xaa Xaa Xaa Xaa Xaa Xaa Xaa Xaa Xaa Lys Cys Xaa Xaa Xaa Xaa
```

```
                    1               5                  10                 15
Xaa Xaa Xaa Xaa Xaa Xaa Gln Cys Xaa Xaa Xaa Xaa Xaa Xaa Xaa
                    20                 25                 30

Xaa Xaa Cys Lys Xaa Xaa Xaa Xaa Xaa Xaa Xaa Xaa Xaa Xaa Xaa
                    35                 40                 45

Xaa Xaa Xaa Xaa Xaa Xaa Xaa Xaa Lys Cys Met Xaa Xaa Xaa Xaa
                    50                 55                 60

Xaa Xaa Xaa Xaa Xaa Cys Xaa Cys Xaa Xaa Xaa Xaa Xaa Xaa Xaa
                    65                 70                 75                 80

Xaa Xaa

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (6)..(9)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (17)..(23)
<223> OTHER INFORMATION: Any amino acid
<220> FEATURE:
<221> NAME/KEY: MOD_RES
<222> LOCATION: (27)..(29)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (33)..(34)
<223> OTHER INFORMATION: Any amino acid

<400> SEQUENCE: 6

Xaa Xaa Xaa Lys Cys Xaa Xaa Xaa Xaa Gln Cys Xaa Xaa Xaa Cys Lys
1               5                   10                  15

Xaa Xaa Xaa Xaa Xaa Xaa Xaa Lys Cys Met Xaa Xaa Xaa Cys Xaa Cys
                    20                  25                  30

Xaa Xaa

<210> SEQ ID NO 7
<211> LENGTH: 55
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
```

```
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (36)..(55)
<223> OTHER INFORMATION: Any amino acid and this region may encompass 1-
      20 residues

<400> SEQUENCE: 7

Ile Xaa Val Lys Cys Xaa Xaa Pro Xaa Gln Cys Xaa Xaa Pro Cys Lys
1               5                   10                  15

Xaa Xaa Xaa Gly Xaa Xaa Xaa Xaa Xaa Lys Cys Met Asn Xaa Lys Cys
            20                  25                  30

Xaa Cys Tyr Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa
    50                  55

<210> SEQ ID NO 8
<211> LENGTH: 53
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(23)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
```

```
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (34)..(53)
<223> OTHER INFORMATION: Any amino acid and this region may encompass 1-
      20 residues

<400> SEQUENCE: 8

Ile Xaa Val Lys Cys Xaa Xaa Pro Xaa Gln Cys Xaa Xaa Pro Cys Lys
1               5                   10                  15

Xaa Xaa Gly Xaa Xaa Xaa Xaa Lys Cys Met Asn Xaa Lys Cys Xaa Cys
            20                  25                  30

Tyr Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa
    50

<210> SEQ ID NO 9
<211> LENGTH: 65
<212> TYPE: PRT
<213> ORGANISM: Odontobuthus doriae

<400> SEQUENCE: 9

Gly Val Arg Asp Ala Tyr Ile Ala Asp Lys Asn Cys Val Tyr Thr
1               5                   10                  15

Cys Ala Ser Asn Gly Tyr Cys Asn Thr Glu Cys Thr Lys Asn Gly Ala
            20                  25                  30

Glu Ser Gly Tyr Cys Gln Trp Ile Gly Arg Tyr Gly Asn Ala Cys Trp
        35                  40                  45

Cys Ile Lys Leu Pro Asp Glu Val Pro Ile Arg Ile Pro Gly Lys Cys
    50                  55                  60

Arg
65

<210> SEQ ID NO 10
<211> LENGTH: 35
<212> TYPE: PRT
<213> ORGANISM: Thrixopelma pruriens

<400> SEQUENCE: 10

Glu Cys Arg Tyr Trp Leu Gly Gly Cys Ser Ala Gly Gln Thr Cys Cys
1               5                   10                  15

Lys His Leu Val Cys Ser Arg Arg His Gly Trp Cys Val Trp Asp Gly
            20                  25                  30

Thr Phe Ser
        35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 11

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30
```

-continued

Cys His Cys Thr Pro Lys
        35

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      toxin consensus peptide
<220> FEATURE:
<221> NAME/KEY: MOD_RES
<222> LOCATION: (1)..(4)
<223> OTHER INFORMATION: Any amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(24)
<223> OTHER INFORMATION: Any amino acid
<220> FEATURE:
<221> NAME/KEY: MOD_RES
<222> LOCATION: (26)..(29)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (33)..(34)
<223> OTHER INFORMATION: Any amino acid

<400> SEQUENCE: 12

Xaa Xaa Xaa Xaa Cys Xaa Xaa Xaa Xaa Xaa Cys Xaa Xaa Xaa Cys Xaa
1               5                   10                  15

Xaa Xaa Xaa Xaa Xaa Xaa Xaa Xaa Cys Xaa Xaa Xaa Xaa Cys Xaa Cys
            20                  25                  30

Xaa Xaa

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 13

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin consensus peptide
<220> FEATURE:
<221> NAME/KEY: MOD_RES

```
<222> LOCATION: (1)..(6)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<221> NAME/KEY: MOD_RES
<222> LOCATION: (19)..(26)
<223> OTHER INFORMATION: Any amino acid
<220> FEATURE:
<221> NAME/KEY: MOD_RES
<222> LOCATION: (30)..(31)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(38)
<223> OTHER INFORMATION: Any amino acid

<400> SEQUENCE: 14

```
<222> LOCATION: (20)..(26)
<223> OTHER INFORMATION: Any amino acid
<220> FEATURE:
<221> NAME/KEY: MOD_RES
<222> LOCATION: (30)..(31)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(38)
<223> OTHER INFORMATION: Any amino acid

<400> SEQUENCE: 16

Xaa Xaa Xaa Xaa Xaa Xaa Lys Cys Xaa Xaa Xaa Xaa Gln Cys Leu Xaa
1               5                   10                  15

Xaa Cys Lys Xaa Xaa Xaa Xaa Xaa Xaa Lys Cys Met Xaa Xaa Lys
            20                  25                  30

Cys Xaa Cys Xaa Xaa Xaa
        35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (36)..(36)
<223> OTHER INFORMATION: Any amino acid

<400> SEQUENCE: 17

Ile Xaa Val Lys Cys Xaa Xaa Pro Xaa Gln Cys Xaa Xaa Pro Cys Lys
1               5                   10                  15

Xaa Xaa Xaa Gly Xaa Xaa Xaa Xaa Xaa Lys Cys Met Asn Xaa Lys Cys
            20                  25                  30

Xaa Cys Tyr Xaa
```

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
      toxin consensus peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(23)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (34)..(34)
<223> OTHER INFORMATION: Any amino acid

<400> SEQUENCE: 18

Ile Xaa Val Lys Cys Xaa Xaa Pro Xaa Gln Cys Xaa Xaa Pro Cys Lys
1               5                   10                  15

Xaa Xaa Gly Xaa Xaa Xaa Xaa Lys Cys Met Asn Xaa Lys Cys Xaa Cys
            20                  25                  30

Tyr Xaa

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 19

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
            35

<210> SEQ ID NO 20
<211> LENGTH: 37

```
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 20

Val Arg Ile Pro Val Ser Cys Lys His Ser Gly Gln Cys Leu Lys Pro
1               5                   10                  15

Cys Lys Asp Ala Gly Met Arg Phe Gly Lys Cys Met Asn Gly Lys Cys
            20                  25                  30

Asp Cys Thr Pro Lys
        35

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 21

Val Gly Ile Pro Val Ser Cys Lys His Ser Gly Gln Cys Ile Lys Pro
1               5                   10                  15

Cys Lys Asp Ala Gly Met Arg Phe Gly Lys Cys Met Asn Arg Lys Cys
            20                  25                  30

Asp Cys Thr Pro Lys
        35

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 22

Gly Val Gly Ile Asn Val Lys Cys Lys His Ser Gly Gln Cys Leu Lys
1               5                   10                  15

Pro Cys Lys Asp Ala Gly Met Arg Phe Gly Lys Cys Ile Asn Gly Lys
            20                  25                  30

Cys Asp Cys Thr Pro Lys Gly
        35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 23

Gly Val Pro Ile Asn Val Lys Cys Arg Gly Ser Pro Gln Cys Ile Gln
1               5                   10                  15

Pro Cys Arg Asp Ala Gly Met Arg Phe Gly Lys Cys Met Asn Gly Lys
            20                  25                  30

Cys His Cys Thr Pro Gln
        35

<210> SEQ ID NO 24
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 24

Ala Val Arg Ile Pro Val Ser Cys Lys His Ser Gly Gln Cys Leu Lys
1               5                   10                  15

Pro Cys Lys Asp Ala Gly Met Arg Phe Gly Lys Cys Met Asn Gly Lys
            20                  25                  30

Cys Asp Cys Thr Pro Lys
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 25

Val Gly Ile Asn Val Lys Cys Lys His Ser Gly Gln Cys Leu Lys Pro
1               5                   10                  15

Cys Lys Asp Ala Gly Met Arg Phe Gly Lys Cys Ile Asn Gly Lys Cys
            20                  25                  30

Asp Cys Thr Pro Lys
        35

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 26

Gly Val Pro Ile Asn Val Lys Cys Thr Gly Ser Pro Gln Cys Leu Lys
1               5                   10                  15

Pro Cys Lys Asp Ala Gly Met Arg Phe Gly Lys Cys Ile Asn Gly Lys
            20                  25                  30

Cys His Cys Thr Pro Lys
        35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 27

Gly Val Pro Ile Asn Val Ser Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 28
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 28

Gly Val Pro Ile Asn Val Pro Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 29

Gly Val Ile Ile Asn Val Lys Cys Lys Ile Ser Arg Gln Cys Leu Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 30

Thr Ile Ile Asn Val Lys Cys Thr Ser Pro Lys Gln Cys Ser Lys Pro
1               5                   10                  15

Cys Lys Glu Leu Tyr Gly Ser Ser Ala Gly Ala Lys Cys Met Asn Gly
            20                  25                  30

Lys Cys Lys Cys Tyr Asn Asn
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 31

Thr Val Ile Asn Val Lys Cys Thr Ser Pro Lys Gln Cys Leu Lys Pro
1               5                   10                  15

Cys Lys Asp Leu Tyr Gly Pro His Ala Gly Ala Lys Cys Met Asn Gly
            20                  25                  30

Lys Cys Lys Cys Tyr Asn Asn
        35

<210> SEQ ID NO 32
<211> LENGTH: 39
```

<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 32

Thr Ile Ile Asn Val Lys Cys Thr Ser Pro Lys Gln Cys Leu Lys Pro
1               5                   10                  15

Cys Lys Asp Leu Tyr Gly Pro His Ala Gly Ala Lys Cys Met Asn Gly
            20                  25                  30

Lys Cys Lys Cys Tyr Asn Asn
        35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 33

Ile Phe Ile Asn Val Lys Cys Ser Leu Pro Gln Gln Cys Leu Arg Pro
1               5                   10                  15

Cys Lys Asp Arg Phe Gly Gln His Ala Gly Gly Lys Cys Ile Asn Gly
            20                  25                  30

Lys Cys Lys Cys Tyr Pro
        35

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 34

Thr Ile Ile Asn Val Lys Cys Thr Ser Pro Lys Gln Cys Leu Leu Pro
1               5                   10                  15

Cys Lys Glu Ile Tyr Gly Ile His Ala Gly Ala Lys Cys Met Asn Gly
            20                  25                  30

Lys Cys Lys Cys Tyr Lys Ile
        35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 35

Thr Ile Ile Asn Val Lys Cys Thr Ser Pro Lys Gln Cys Leu Pro Pro
1               5                   10                  15

Cys Lys Glu Ile Tyr Gly Arg His Ala Gly Ala Lys Cys Met Asn Gly
            20                  25                  30

Lys Cys His Cys Ser Lys Ile
        35

<210> SEQ ID NO 36
<211> LENGTH: 38

```
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 36

Ile Thr Ile Asn Val Lys Cys Thr Ser Pro Gln Gln Cys Leu Arg Pro
1               5                   10                  15

Cys Lys Asp Arg Phe Gly Gln His Ala Gly Gly Lys Cys Ile Asn Gly
            20                  25                  30

Lys Cys Lys Cys T

```
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 40

Val Phe Ile Asn Ala Lys Cys Arg Gly Ser Pro Glu Cys Leu Pro Lys
1               5                   10                  15

Cys Lys Glu Ala Ile Gly Lys Ala Ala Gly Lys Cys Met Asn Gly Lys
            20                  25                  30

Cys Lys Cys Tyr Pro
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 41

Val Phe Ile Asn Val Lys Cys Arg Gly Ser Pro Glu Cys Leu Pro Lys
1               5                   10                  15

Cys Lys Glu Ala Ile Gly Lys Ser Ala Gly Lys Cys Met Asn Gly Lys
            20                  25                  30

Cys Lys Cys Tyr Pro
        35

<210> SEQ ID NO 42
<211> LENGTH: 39
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 42

Thr Ile Ile Asn Val Lys Cys Thr Ser Pro Lys Gln Cys Leu Pro Pro
1               5                   10                  15

Cys Lys Ala Gln Phe Gly Gln Ser Ala Gly Ala Lys Cys Met Asn Gly
            20                  25                  30

Lys Cys Lys Cys Tyr Pro His
        35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 43

Thr Ile Ile Asn Val Lys Cys Thr Ser Pro Lys Gln Cys Leu Pro Pro
1               5                   10                  15

Cys Lys Ala Gln Phe Gly Gln Ser Ala Gly Ala Lys Cys Met Asn Gly
            20                  25                  30

Lys Cys Lys Cys Tyr
        35

<210> SEQ ID NO 44
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 44

Thr Ile Ile Asn Glu Lys Cys Phe Ala Thr Ser Gln Cys Trp Thr Pro
1               5                   10                  15

Cys Lys Lys Ala Ile Gly Ser Leu Gln Ser Lys Cys Met Asn Gly Lys
            20                  25                  30

Cys Lys Cys Tyr Asn Gly
        35

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 45

Thr Ile Ser Cys Thr Asn Pro Lys Gln Cys Tyr Pro His Cys Lys Lys
1               5                   10                  15

Glu Thr Gly Tyr Pro Asn Ala Lys Cys Met Asn Arg Lys Cys Lys Cys
            20                  25                  30

Phe Gly Arg
        35

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 46

Thr Ile Ser Cys Thr Asn Glu Lys Gln Cys Tyr Pro His Cys Lys Lys
1               5                   10                  15

Glu Thr Gly Tyr Pro Asn Ala Lys Cys Met Asn Arg Lys Cys Lys Cys
            20                  25                  30

Phe Gly Arg
        35

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 47

Ile Thr Ile Asn Val Lys Cys Thr Ser Pro Gln Gln Cys Leu Arg Pro
1               5                   10                  15

Cys Lys Asp Arg Phe Gly Gln His Ala Gly Gly Lys Cys Ile Asn Gly
            20                  25                  30

Lys Cys Lys Cys Tyr Pro
        35

<210> SEQ ID NO 48
<211> LENGTH: 39
```

<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 48

Thr Val Ile Asp Val Lys Cys Thr Ser Pro Lys Gln Cys Leu Pro Pro
1               5                   10                  15

Cys Lys Ala Gln Phe Gly Ile Arg Ala Gly Ala Lys Cys Met Asn Gly
            20                  25                  30

Lys Cys Lys Cys Tyr Pro His
        35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 49

Glx Phe Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
            20                  25                  30

Cys Arg Cys Tyr Ser
        35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 50

Glx Phe Thr Asp Val Asp Cys Ser Val Ser Lys Glu Cys Trp Ser Val
1               5                   10                  15

Cys Lys Asp Leu Phe Gly Val Asp Arg Gly Lys Cys Met Gly Lys Lys
            20                  25                  30

Cys Arg Cys Tyr Gln
        35

<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 51

Glx Phe Thr Gln Glu Ser Cys Thr Ala Ser Asn Gln Cys Trp Ser Ile
1               5                   10                  15

Cys Lys Arg Leu His Asn Thr Asn Arg Gly Lys Cys Met Asn Lys Lys
            20                  25                  30

Cys Arg Cys Tyr Ser
        35

<210> SEQ ID NO 52
<211> LENGTH: 36

<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 52

```
Gly Leu Ile Asp Val Arg Cys Tyr Asp Ser Arg Gln Cys Trp Ile Ala
1               5                   10                  15

Cys Lys Lys Val Thr Gly Ser Thr Gln Gly Lys Cys Gln Asn Lys Gln
            20                  25                  30

Cys Arg Cys Tyr
        35
```

<210> SEQ ID NO 53
<211> LENGTH: 37
<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 53

```
Glx Phe Thr Asp Val Lys Cys Thr Gly Ser Lys Gln Cys Trp Pro Val
1               5                   10                  15

Cys Lys Gln Met Phe Gly Lys Pro Asn Gly Lys Cys Met Asn Gly Lys
            20                  25                  30

Cys Arg Cys Tyr Ser
        35
```

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 54

```
Glx Phe Thr Asn Val Ser Cys Ser Ala Ser Ser Gln Cys Trp Pro Val
1               5                   10                  15

Cys Lys Lys Leu Phe Gly Thr Tyr Arg Gly Lys Cys Met Met Ser Lys
            20                  25                  30

Cys Arg Cys Tyr Ser
        35
```

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
toxin peptide

<400> SEQUENCE: 55

```
Ala Phe Cys Asn Leu Arg Met Cys Gln Leu Ser Cys Arg Ser Leu Gly
1               5                   10                  15

Leu Leu Gly Lys Cys Ile Gly Asp Lys Cys Glu Cys Val Lys His
            20                  25                  30
```

<210> SEQ ID NO 56
<211> LENGTH: 31
<212> TYPE: PRT
<213> ORGANISM: Artificial Sequence
<220> FEATURE:

<223> OTHER INFORMATION: Description of Artificial Sequence: Synthetic
      toxin peptide

<400> SEQUENCE: 56

Thr Val Cys Asn Leu Arg Arg Cys Gln Leu Ser Cys Arg Ser Leu Gly
1               5                   10                  15

Leu Leu Gly Lys Cys Ile Gly Val Lys Cys Glu Cys Val Lys His
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 57

Ala Val Cys Asn Leu Lys Arg Cys Gln Leu Ser Cys Arg Ser Leu Gly
1               5                   10                  15

Leu Leu Gly Lys Cys Ile Gly Asp Lys Cys Glu Cys Val Lys His
            20                  25                  30

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 58

Val Ser Cys Glu Asp Cys Pro Glu His Cys Ser Thr Gln Lys Ala Gln
1               5                   10                  15

Ala Lys Cys Asp Asn Asp Lys Cys Val Cys Glu Pro Ile
            20                  25

<210> SEQ ID NO 59
<211> LENGTH: 29
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 59

Ala Thr Cys Glu Asp Cys Pro Glu His Cys Ala Thr Gln Asn Ala Arg
1               5                   10                  15

Ala Lys Cys Asp Asn Asp Lys Cys Val Cys Glu Pro Lys
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 60

Val Gly Cys Glu Glu Cys Pro Met His Cys Lys Gly Lys Asn Ala Lys
1               5                   10                  15

Pro Thr Cys Asp Asp Gly Val Cys Asn Cys Asn Val
            20                  25

```
<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 61

Val Gly Cys Glu Glu Cys Pro Met His Cys Lys Gly Lys Asn Ala Asn
1               5                   10                  15

Pro Thr Cys Asp Asp Gly Val Cys Asn Cys Asn Val
            20                  25

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 62

Val Val Ile Gly Gln Arg Cys Tyr Arg Ser Pro Asp Cys Tyr Ser Ala
1               5                   10                  15

Cys Lys Lys Leu Val Gly Lys Ala Thr Gly Lys Cys Thr Asn Gly Arg
            20                  25                  30

Cys Asp Cys
35

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      leader sequence

<400> SEQUENCE: 63

Ala Glu Gly Ala
1

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      leader sequence

<400> SEQUENCE: 64

Gly Ser Ala Ser Ser Ala
1               5

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      signal peptide

<400> SEQUENCE: 65

Met Ala Ala Glu
1

<210> SEQ ID NO 66
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 66

Ser Thr Met Ala Asp Leu His Asp Ala Ala Lys
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 67

Ser Thr Met Ala Ser Thr Glu Phe Ala Ala Lys
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 68

Ser Thr Met Ala Val Asp Gly Val Ala Ala Lys
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 69

Ser Thr Met Cys Gln Pro Glu Leu Ala Ala Lys
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 70

Ser Thr Met Glu Gln Val Asp Ala Ala Ala Lys
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 71

Ser Thr Met Gly Ser Asp Met His Ala Ala Lys
```

```
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 72

Ser Thr Met His Thr Asp Tyr Thr Ala Ala Lys
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 73

Ser Thr Met Leu Glu Leu Thr Ser Ala Ala Lys
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 74

Ser Thr Met Leu Leu Thr Val Pro Ala Ala Lys
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 75

Ser Thr Met Pro Leu Ala Gly Pro Ala Ala Lys
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 76

Ser Thr Met Ser Val Ser Val Ser Ala Ala Lys
1               5                   10

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide
```

<400> SEQUENCE: 77

Thr Val Ile Asp Val Lys Cys Thr Ser Pro Lys Gln Cys Leu Pro Pro
1               5                   10                  15

Cys Lys Ala Gln Phe Gly Ile Arg Ala Gly Ala Lys Cys Met Asn Lys
            20                  25                  30

Lys Cys Arg Cys Tyr Ser
        35

<210> SEQ ID NO 78
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 78

Thr Val Ile Asp Val Lys Cys Thr Ser Pro Lys Gln Cys Leu Pro Pro
1               5                   10                  15

Cys Lys Ala Gln Phe Gly Ile Arg Ala Gly Ala Lys Cys Met Asn Lys
            20                  25                  30

Lys Cys Arg Cys Tyr Ser
        35

<210> SEQ ID NO 79
<211> LENGTH: 22
<212> TYPE: PRT
<213> ORGANISM: Conus geographus
<220> FEATURE:
<221> NAME/KEY: MOD_RES
<222> LOCATION: (6)..(7)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 79

Arg Asp Cys Cys Thr Pro Pro Lys Lys Cys Lys Asp Arg Gln Cys Lys
1               5                   10                  15

Pro Gln Arg Cys Cys Ala
            20

<210> SEQ ID NO 80
<211> LENGTH: 22
<212> TYPE: PRT
<213> ORGANISM: Conus geographus

<400> SEQUENCE: 80

Arg Asp Cys Cys Thr Pro Pro Lys Lys Cys Lys Asp Arg Gln Cys Lys
1               5                   10                  15

Pro Gln Arg Cys Cys Ala
            20

<210> SEQ ID NO 81
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 81

Arg Ser Cys Ile Asp Thr Ile Pro Lys Ser Arg Cys Thr Ala Phe Gln

```
                1               5                  10                  15
Cys Lys His Ser Met Lys Tyr Arg Leu Ser Phe Cys Arg Lys Thr Cys
                20                  25                  30

Gly Thr Cys
        35

<210> SEQ ID NO 82
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 82

Arg Thr Cys Lys Asp Leu Ile Pro Val Ser Glu Cys Thr Asp Ile Arg
1               5                   10                  15

Cys Arg Thr Ser Met Lys Tyr Arg Leu Asn Leu Cys Arg Lys Thr Cys
                20                  25                  30

Gly Ser Cys
        35

<210> SEQ ID NO 83
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 83

Arg Thr Cys Lys Asp Leu Met Pro Val Ser Glu Cys Thr Asp Ile Arg
1               5                   10                  15

Cys Arg Thr Ser Met Lys Tyr Arg Leu Asn Leu Cys Arg Lys Thr Cys
                20                  25                  30

Gly Ser Cys
        35

<210> SEQ ID NO 84
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 84

Arg Ala Cys Lys Asp Tyr Leu Pro Lys Ser Glu Cys Thr Gln Phe Arg
1               5                   10                  15

Cys Arg Thr Ser Met Lys Tyr Lys Tyr Thr Asn Cys Lys Lys Thr Cys
                20                  25                  30

Gly Thr Cys
        35

<210> SEQ ID NO 85
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
```

```
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 85

Xaa Xaa Cys Lys Asp Asn Phe Ala Ala Ala Thr Cys Xaa Xaa Xaa Xaa
 1               5                  10                  15

Cys Xaa Xaa Xaa Xaa Xaa Xaa Xaa Xaa Xaa Xaa Cys Ala Lys Thr Cys
             20                  25                  30

Gly Lys Cys
         35

<210> SEQ ID NO 86
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 86

Xaa Xaa Cys Lys Asp Asn Phe Ser Ala Asn Thr Cys Xaa Xaa Xaa Xaa
 1               5                  10                  15

Cys Xaa Xaa Xaa Xaa Xaa Xaa Xaa Xaa Xaa Xaa Cys Ala Lys Thr Cys
             20                  25                  30

Gly Lys Cys
         35

<210> SEQ ID NO 87
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 87

Xaa Xaa Cys Arg Asp Trp Phe Lys Glu Thr Ala Cys Xaa Xaa Xaa Xaa
 1               5                  10                  15

Cys Xaa Xaa Xaa Xaa Xaa Xaa Xaa Xaa Xaa Xaa Cys Ala Lys Thr Cys
             20                  25                  30
```

Glu Leu Cys
        35

<210> SEQ ID NO 88
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 88

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Ala Lys Thr Cys
            20                  25                  30

Gly Phe Cys
        35

<210> SEQ ID NO 89
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 89

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Lys Lys Thr Cys
            20                  25                  30

Gly Thr Cys
        35

<210> SEQ ID NO 90
<211> LENGTH: 35
<212> TYPE: PRT

```
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid

<400> SEQUENCE: 90

Xaa Xaa Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 91
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 91

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Met Lys Met Cys
            20                  25                  30

Gly Leu Cys
        35

<210> SEQ ID NO 92
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid
```

```
<220> FEATURE:
<221> NAME/KEY: MOD_RES
<222> LOCATION: (33)..(34)
<223> OTHER INFORMATION: Any amino acid

<400> SEQUENCE: 92

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Glu Lys Thr Cys
        20                  25                  30

Xaa Xaa Cys
        35

<210> SEQ ID NO 93
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 93

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Pro Lys Lys Cys
        20                  25                  30

Lys Tyr Cys
        35

<210> SEQ ID NO 94
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 94

Xaa Xaa Cys Xaa Xaa Xaa Xaa Xaa Xaa Xaa Cys Xaa Xaa Xaa Xaa
```

```
1               5                  10                  15
Cys Xaa Xaa Xaa Xaa Xaa Xaa Xaa Xaa Xaa Cys Lys Lys Thr Cys
            20                  25                  30

Gly His Cys
        35

<210> SEQ ID NO 95
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 95

Xaa Xaa Cys Xaa Xaa Xaa Xaa Xaa Xaa Xaa Xaa Cys Xaa Xaa Xaa Xaa
1               5                  10                  15

Cys Xaa Xaa Xaa Xaa Xaa Xaa Xaa Xaa Xaa Cys Pro Lys Lys Cys
            20                  25                  30

Gly Leu Cys
        35

<210> SEQ ID NO 96
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 96

Xaa Xaa Cys Xaa Xaa Xaa Xaa Xaa Xaa Xaa Xaa Cys Xaa Xaa Xaa Xaa
1               5                  10                  15

Cys Xaa Xaa Xaa Xaa Xaa Xaa Xaa Xaa Xaa Cys Pro Arg Ser Cys
            20                  25                  30

Asp Tyr Cys
        35
```

```
<210> SEQ ID NO 97
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 97

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Lys Lys Lys Cys
            20                  25                  30

Lys Leu Cys
        35

<210> SEQ ID NO 98
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 98

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Ala Lys Thr Cys
            20                  25                  30

Gly Met Cys
        35

<210> SEQ ID NO 99
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
```

```
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 99

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Pro Lys Met Cys
            20                  25                  30

Asn Tyr Cys
        35

<210> SEQ ID NO 100
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 100

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Arg Lys Thr Cys
            20                  25                  30

Ser Leu Cys
        35

<210> SEQ ID NO 101
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
```

```
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 101

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Arg Lys Thr Cys
            20                  25                  30

Ser Leu Cys
        35

<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 102

Xaa Xaa Cys Lys Asp Asn Phe Ala Ala Ala Thr Cys Xaa Xaa Xaa Xaa
1               5                   10                  15

Cys Xaa Xaa Xaa Xaa Xaa Xaa Xaa Xaa Xaa Cys Ala Lys Thr Cys
            20                  25                  30

Gly Lys Cys
        35

<210> SEQ ID NO 103
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 103

Xaa Xaa Cys Xaa Xaa Xaa Xaa Xaa Xaa Xaa Xaa Cys Xaa Xaa Xaa Xaa
```

```
                1               5                  10                 15
Cys Xaa Xaa Xaa Xaa Xaa Xaa Xaa Xaa Xaa Cys Ala Lys Thr Cys
                20                 25                 30

Gly Ile Cys
        35

<210> SEQ ID NO 104
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 104

Xaa Xaa Cys Xaa Xaa Xaa Xaa Xaa Xaa Xaa Cys Xaa Xaa Xaa Xaa
1               5                  10                 15

Cys Xaa Xaa Xaa Xaa Xaa Xaa Xaa Xaa Xaa Cys Lys Lys Ser Cys
                20                 25                 30

Ala Arg Cys
        35

<210> SEQ ID NO 105
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid

<400> SEQUENCE: 105

Xaa Xaa Cys Xaa Xaa Xaa Xaa Xaa Xaa Xaa Cys Xaa Xaa Xaa Xaa
1               5                  10                 15

Cys Val Ser Glu Glu Lys Thr Met Lys Leu Tyr Cys Arg Lys Thr Cys
                20                 25                 30

Asn Phe Cys
        35

<210> SEQ ID NO 106
<211> LENGTH: 35
<212> TYPE: PRT
```

<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 106

Xaa Xaa Cys Ser Asp Arg Ala His Gly His Ile Cys Xaa Xaa Xaa Xaa
1               5                   10                  15

Cys Xaa Xaa Xaa Xaa Xaa Xaa Xaa Xaa Xaa Xaa Cys Lys Lys Thr Cys
            20                  25                  30

Gly Leu Cys
        35

<210> SEQ ID NO 107
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 107

Xaa Xaa Cys Lys Asp Asn Phe Ser Ala Asn Thr Cys Xaa Xaa Xaa Xaa
1               5                   10                  15

Cys Xaa Xaa Xaa Xaa Xaa Xaa Xaa Xaa Xaa Xaa Cys Ala Lys Thr Cys
            20                  25                  30

Gly Lys Cys
        35

<210> SEQ ID NO 108
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid

<400> SEQUENCE: 108

Xaa Xaa Cys Xaa Xaa Xaa Xaa Xaa Xaa Xaa Cys Xaa Xaa Xaa Xaa
1               5                   10                  15

Cys Arg Thr Asn Pro Lys Trp Met Ala Lys Tyr Cys Arg Lys Ser Cys
            20                  25                  30

Gly Thr Cys
        35

<210> SEQ ID NO 109
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 109

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Lys Arg Ser Cys
            20                  25                  30

Gly Leu Cys
        35

<210> SEQ ID NO 110
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 110

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Gln Lys Ser Cys
            20                  25                  30

Asp Leu Cys
        35

<210> SEQ ID NO 111
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 111

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Pro Glu Thr Cys
            20                  25                  30

Gly Phe Cys
        35

<210> SEQ ID NO 112
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 112

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Lys Arg Ser Cys
            20                  25                  30

Lys Leu Cys
        35

<210> SEQ ID NO 113
<211> LENGTH: 35
<212> TYPE: PRT

```
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 113

Xa

```
<220> FEATURE:
<221> NAME/KEY: MOD_RES
<222> LOCATION: (18)..(27)
<223> OTHER INFORMATION: Any amino acid

<400> SEQUENCE: 115

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Ala Lys Thr Cys
            20                  25                  30

Gly Tyr Cys
        35

<210> SEQ ID NO 116
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 116

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Pro Lys Ser Cys
            20                  25                  30

Gly Ile Cys
        35

<210> SEQ ID NO 117
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 117

Xaa Xaa Cys Xaa Xaa Xaa Xaa Xaa Xaa Xaa Xaa Cys Xaa Xaa Xaa Xaa
```

```
1               5                   10                  15
Cys Xaa Xaa Xaa Xaa Xaa Xaa Xaa Xaa Xaa Cys Leu Lys Ser Cys
            20                  25                  30

Gly Phe Cys
        35

<210> SEQ ID NO 118
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 118

```
<210> SEQ ID NO 120
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid

<400> SEQUENCE: 120

Xaa Xaa Cys Xaa Xaa Xaa Xaa Xaa Xaa Xaa Xaa Cys Xaa Xaa Xaa Xaa
1               5                   10                  15

Cys Gln Arg Asn Thr Lys Trp Met Phe His Tyr Cys Pro Val Ser Cys
            20                  25                  30

Gly Ile Cys
        35

<210> SEQ ID NO 121
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 121

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Lys Met Thr Cys
            20                  25                  30

Asn Leu Cys
        35

<210> SEQ ID NO 122
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
```

```
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 122

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Xaa Cys Ala Tyr Thr Cys
                20                  25                  30

Asp Thr Cys
        35

<210> SEQ ID NO 123
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid

<400> SEQUENCE: 123

Xaa Xaa Cys Xaa Xaa Xaa Xaa Xaa Xaa Xaa Xaa Cys Xaa Xaa Xaa Xaa
1               5                   10                  15

Cys Thr Arg Asn Val Lys Phe Met Leu Asp Lys Cys Trp Arg Ser Cys
                20                  25                  30

Ser Gly Cys
        35

<210> SEQ ID NO 124
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid
```

<400> SEQUENCE: 124

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Ala Lys Ser Cys
            20                  25                  30

Ala Phe Cys
        35

<210> SEQ ID NO 125
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 125

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Arg Lys Thr Cys
            20                  25                  30

Ser His Cys
        35

<210> SEQ ID NO 126
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid
<220> FEATURE:
<221> NAME/KEY: MOD_RES
<222> LOCATION: (29)..(31)
<223> OTHER INFORMATION: Any amino acid

<400> SEQUENCE: 126

Xaa Xaa Cys Xaa Xaa Xaa Xaa Xaa Xaa Xaa Xaa Cys Xaa Xaa Xaa Xaa

```
                1               5                   10                  15
Cys Xaa Xaa Xaa Xaa Xaa Xaa Xaa Xaa Xaa Cys Xaa Xaa Xaa Cys
                20                  25                  30

Lys Ser Cys
        35

<210> SEQ ID NO 127
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 127

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Pro Lys Ser Cys
                20                  25                  30

Arg Met Cys
        35

<210> SEQ ID NO 128
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 128

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Gln Ala Ala Cys
                20                  25                  30

Glu Ile Cys
        35
```

```
<210> SEQ ID NO 129
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 129

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Arg Arg Ser Cys
            20                  25                  30

Gly Ser Cys
        35

<210> SEQ ID NO 130
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 130

Xaa Xaa Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Lys Lys Ser Cys
            20                  25                  30

Asn Leu Cys
        35

<210> SEQ ID NO 131
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide
```

```
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid

<400> SEQUENCE: 131

Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Lys Lys Ser Cys
            20                  25                  30

Asn Leu Cys
        35

<210> SEQ ID NO 132
<211> LENGTH: 165
<212> TYPE: PRT
<213> ORGANISM: Artificial Sequence
<220> FEATURE:
<223> OTHER INFORMATION: Description of Artificial Sequence: Synthetic
      kaliotoxin phagemid sequence

<400> SEQUENCE: 132

Met Lys Lys Leu Leu Phe Ala Ile Pro Leu Val Val Pro Phe Tyr Ser
1               5                   10                  15

Met Ala Ala Glu Gly Val Glu Ile Asn Val Lys Cys Ser Gly Ser Pro
            20                  25                  30

Gln Cys Leu Lys Pro Cys Lys Asp Ala Gly Met Arg Phe Gly Lys Cys
        35                  40                  45

Met Asn Arg Lys Cys His Cys Thr Pro Lys Gly Ser Ala Ser Ser Ala
    50                  55                  60

Thr Arg Pro Phe Val Cys Glu Tyr Gln Gly Gln Ser Ser Asp Leu Pro
65                  70                  75                  80

Gln Pro Pro Val Asn Ala Gly Gly Gly Ser Gly Gly Ser Gly Gly
                85                  90                  95

Gly Ser Glu Gly Gly Gly Ser Glu Gly Gly Ser Glu Gly Gly Gly
            100                 105                 110

Ser Glu Gly Gly Gly Ser Gly Gly Ser Gly Ser Gly Asp Phe Tyr
        115                 120                 125

Glu Lys Met Ala Asn Ala Asn Lys Gly Ala Met Thr Glu Asn Ala Asp
    130                 135                 140

Glu Asn Ala Leu Gln Ser Asp Ala Lys Gly Lys Leu Asp Ser Val Ala
145                 150                 155                 160

Thr Asp Tyr Gly Ala
                165

<210> SEQ ID NO 133
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide
```

```
<400> SEQUENCE: 133

Met Ala Ala Glu Gly Val Glu Ile Asn Val Lys Cys Ser Gly Ser Pro
1               5                   10                  15

Gln Cys Leu Arg Pro Cys Lys Asp Arg Phe Gly Gln His Ala Gly Gly
            20                  25                  30

Lys Cys Met Asn Arg Lys Cys Lys Cys Phe Gly Arg Gly Ser Ala Ser
        35                  40                  45

Ser Ala Thr Arg Pro Phe Val Cys Glu Tyr Gln Gly Gln Ser Ser Asp
    50                  55                  60

Leu Pro
65

<210> SEQ ID NO 134
<211> LENGTH: 61
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 134

Met Ala Ala Glu Gly Val Glu Ile Asn Val Lys Cys Ser Gly Ser Pro
1               5                   10                  15

Gln Cys Leu Glu Pro Cys Lys Lys Ala Gly Met Arg Phe Gly Lys Cys
            20                  25                  30

Met Asn Gly Lys Cys His Cys Gly Ser Ala Ser Ser Ala Thr Arg Pro
        35                  40                  45

Phe Val Cys Glu Tyr Gln Gly Gln Ser Ser Asp Leu Pro
    50                  55                  60

<210> SEQ ID NO 135
<211> LENGTH: 61
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 135

Met Ala Ala Glu Gly Val Glu Ile Asn Val Lys Cys Ser Gly Ser Pro
1               5                   10                  15

Gln Cys Ile Lys Pro Cys Lys Asp Ala Gly Met Arg Phe Gly Lys Cys
            20                  25                  30

Met Asn Gly Lys Cys His Cys Gly Ser Ala Ser Ser Ala Thr Arg Pro
        35                  40                  45

Phe Val Cys Glu Tyr Gln Gly Gln Ser Ser Asp Leu Pro
    50                  55                  60

<210> SEQ ID NO 136
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 136

Met Ala Ala Glu Gly Val Glu Ile Asn Val Lys Cys Ser Gly Ser Pro
1               5                   10                  15

Gln Cys Leu Arg Pro Cys Lys Asp Arg Phe Gly Gln His Ala Gly Gly
            20                  25                  30
```

```
Lys Cys Met Asn Arg Lys Cys Lys Cys Phe Gly Arg Gly Ser Ala Ser
            35                  40                  45

Ser Ala Thr Arg Pro Phe Val Cys Glu Tyr Gln Gly Gln Ser Ser Asp
        50                  55                  60

Leu Pro
65

<210> SEQ ID NO 137
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 137

Met Ala Ala Glu Gly Val Glu Ile Asn Val Lys Cys Ser Gly Ser Pro
1               5                   10                  15

Gln Cys Ile Lys Pro Cys Lys Asp Ala Gly Met Arg Phe Gly Lys Cys
            20                  25                  30

Met Asn Gly Lys Cys Asp Cys Thr Pro Lys Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 138
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 138

Met Ala Ala Glu Gly Val Glu Ile Asn Val Lys Cys Ser Gly Ser Pro
1               5                   10                  15

Gln Cys Leu Arg Pro Cys Lys Asp Arg Phe Gly Gln His Ala Gly Gly
            20                  25                  30

Lys Cys Met Asn Arg Lys Cys Lys Cys Phe Gly Arg Gly Ser Ala Ser
            35                  40                  45

Ser Ala Thr Arg Pro Phe Val Cys Glu Tyr Gln Gly Gln Ser Ser Asp
        50                  55                  60

Leu Pro
65

<210> SEQ ID NO 139
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 139

Met Ala Ala Glu Gly Val Glu Ile Asn Val Lys Cys Ser Gly Ser Pro
1               5                   10                  15

Gln Cys Leu Glu Pro Cys Lys Lys Ala Gly Met Arg Phe Gly Lys Cys
            20                  25                  30

Met Asn Gly Lys Cys Arg Cys Tyr Ser Gly Ser Ala Ser Ser Ala Thr
        35                  40                  45

Arg Pro Phe Val Cys Glu Tyr Gln Gly Gln Ser Ser Asp Leu Pro
```

<210> SEQ ID NO 140
<211> LENGTH: 60
<212> TYPE: PRT
<213> ORGANISM: Artificial Sequence
<220> FEATURE:
<223> OTHER INFORMATION: Description of Artificial Sequence: Synthetic toxin peptide

<400> SEQUENCE: 140

Met Ala Ala Glu Gly Val Glu Ile Asn Val Lys Cys Ser Gly Ser Pro
1               5                   10                  15

Gln Cys Leu Lys Pro Cys Lys Lys Ala Gly Met Arg Phe Gly Lys Cys
            20                  25                  30

Met Asn Lys Arg Cys Tyr Gly Ser Ala Ser Ala Thr Arg Pro Phe
        35                  40                  45

Val Cys Glu Tyr Gln Gly Gln Ser Ser Asp Leu Pro
    50                  55                  60

<210> SEQ ID NO 141
<211> LENGTH: 63
<212> TYPE: PRT
<213> ORGANISM: Artificial Sequence
<220> FEATURE:
<223> OTHER INFORMATION: Description of Artificial Sequence: Synthetic toxin peptide

<400> SEQUENCE: 141

Met Ala Ala Glu Gly Val Glu Ile Asn Val Lys Cys Ser Gly Ser Pro
1               5                   10                  15

Gln Cys Leu Glu Pro Cys Lys Lys Ala Gly Met Arg Phe Gly Lys Cys
            20                  25                  30

Met Met Ser Lys Cys Arg Cys Tyr Ser Gly Ser Ala Ser Ala Thr
        35                  40                  45

Arg Pro Phe Val Cys Glu Tyr Gln Gly Gln Ser Ser Asp Leu Pro
    50                  55                  60

<210> SEQ ID NO 142
<211> LENGTH: 63
<212> TYPE: PRT
<213> ORGANISM: Artificial Sequence
<220> FEATURE:
<223> OTHER INFORMATION: Description of Artificial Sequence: Synthetic toxin peptide

<400> SEQUENCE: 142

Met Ala Ala Glu Gly Phe Thr Asn Val Ser Cys Thr Thr Ser Lys Gln
1               5                   10                  15

Cys Trp Thr Pro Cys Lys Lys Ala Ile Gly Ser Leu Gln Ser Lys Cys
            20                  25                  30

Met Met Ser Lys Cys Arg Cys Tyr Ser Gly Ser Ala Ser Ala Thr
        35                  40                  45

Arg Pro Phe Val Cys Glu Tyr Gln Gly Gln Ser Ser Asp Leu Pro
    50                  55                  60

<210> SEQ ID NO 143
<211> LENGTH: 62
<212> TYPE: PRT
<213> ORGANISM: Artificial Sequence
<220> FEATURE:
<223> OTHER INFORMATION: Description of Artificial Sequence: Synthetic toxin peptide

```
<400> SEQUENCE: 143

Met Ala Ala Glu Gly Phe Thr Asn Val Ser Cys Thr Thr Ser Lys Gln
1               5                   10                  15

Cys Leu Pro Pro Cys Lys Ala Gln Phe Gly Ile Arg Ala Gly Ala Lys
            20                  25                  30

Cys Met Asn Gly Lys Cys His Cys Gly Ser Ala Ser Ala Thr Arg
        35                  40                  45

Pro Phe Val Cys Glu Tyr Gln Gly Gln Ser Ser Asp Leu Pro
    50                  55                  60

<210> SEQ ID NO 144
<211> LENGTH: 60
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 144

Met Ala Ala Glu Gly Phe Thr Asn Val Ser Cys Thr Thr Ser Lys Gln
1               5                   10                  15

Cys Trp Ser Val Cys Lys Asp Leu Phe Gly Val Asp Arg Gly Lys Cys
            20                  25                  30

Met Asn Lys Arg Cys Tyr Gly Ser Ala Ser Ala Thr Arg Pro Phe
        35                  40                  45

Val Cys Glu Tyr Gln Gly Gln Ser Ser Asp Leu Pro
    50                  55                  60

<210> SEQ ID NO 145
<211> LENGTH: 60
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 145

Met Ala Ala Glu Gly Phe Thr Asn Val Ser Cys Thr Thr Ser Lys Gln
1               5                   10                  15

Cys Tyr Pro His Cys Lys Lys Glu Thr Gly Tyr Pro Asn Ala Lys Cys
            20                  25                  30

Met Asn Lys Arg Cys Tyr Gly Ser Ala Ser Ala Thr Arg Pro Phe
        35                  40                  45

Val Cys Glu Tyr Gln Gly Gln Ser Ser Asp Leu Pro
    50                  55                  60

<210> SEQ ID NO 146
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 146

Met Ala Ala Glu Gly Phe Thr Asn Val Ser Cys Thr Thr Ser Lys Gln
1               5                   10                  15

Cys Trp Thr Pro Cys Lys Lys Ala Ile Gly Ser Leu Gln Ser Lys Cys
            20                  25                  30

Met Asn Gly Lys Cys His Cys Thr Pro Lys Gly Ser Ala Ser Ser Ala
        35                  40                  45
```

Thr Arg Pro Phe Val Cys Glu Tyr Gln Gly Gln Ser Ser Asp Leu Pro
         50                  55                  60

<210> SEQ ID NO 147
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 147

Met Ala Ala Glu Gly Phe Thr Asn Val Ser Cys Thr Thr Ser Lys Gln
1               5                   10                  15

Cys Tyr Pro His Cys Lys Lys Glu Thr Gly Tyr Pro Asn Ala Lys Cys
            20                  25                  30

Met Asn Lys Lys Cys Arg Cys Tyr Ser Gly Ser Ala Ser Ser Ala Thr
        35                  40                  45

Arg Pro Phe Val Cys Glu Tyr Gln Gly Gln Ser Ser Asp Leu Pro
    50                  55                  60

<210> SEQ ID NO 148
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 148

Met Ala Ala Glu Gly Phe Thr Asn Val Ser Cys Thr Thr Ser Lys Gln
1               5                   10                  15

Cys Trp Ser Ile Cys Lys Arg Leu His Asn Thr Asn Arg Gly Lys Cys
            20                  25                  30

Met Asn Gly Lys Cys Lys Cys Tyr Asn Asn Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 149
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 149

Met Ala Ala Glu Gly Phe Thr Asn Val Ser Cys Thr Thr Ser Lys Gln
1               5                   10                  15

Cys Trp Ser Val Cys Gln Arg Leu His Asn Thr Ser Arg Gly Lys Cys
            20                  25                  30

Met Asn Gly Lys Cys Lys Cys Tyr Asn Gly Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 150
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 150

Met Ala Ala Glu Gly Phe Thr Asn Val Ser Cys Thr Thr Ser Lys Gln
1               5                   10                  15

Cys Trp Ser Ile Cys Lys Arg Leu His Asn Thr Asn Arg Gly Lys Cys
            20                  25                  30

Met Asn Gly Lys Cys Lys Cys Tyr Pro His Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 151
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 151

Met Ala Ala Glu Gly Phe Thr Asn Val Ser Cys Thr Thr Ser Lys Gln
1               5                   10                  15

Cys Trp Ser Ile Cys Lys Arg Leu His Asn Thr Asn Arg Gly Lys Cys
            20                  25                  30

Met Asn Arg Lys Cys His Cys Thr Pro Lys Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 152
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 152

Met Ala Ala Glu Gly Phe Thr Asn Val Ser Cys Thr Thr Ser Lys Gln
1               5                   10                  15

Cys Trp Pro Val Cys Lys Lys Leu Phe Gly Thr Tyr Arg Gly Lys Cys
            20                  25                  30

Met Asn Gly Lys Cys His Cys Thr Pro Gln Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 153
<211> LENGTH: 61
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 153

Met Ala Ala Glu Gly Phe Thr Asn Val Ser Cys Thr Thr Ser Lys Gln
1               5                   10                  15

Cys Trp Ile Ala Cys Lys Lys Val Thr Gly Ser Thr Gln Gly Lys Cys
            20                  25                  30

Met Asn Gly Lys Cys His Cys Gly Ser Ala Ser Ser Ala Thr Arg Pro
        35                  40                  45

```
Phe Val Cys Glu Tyr Gln Gly Gln Ser Ser Asp Leu Pro
    50                  55                  60
```

<210> SEQ ID NO 154
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 154

```
Met Ala Ala Glu Val Arg Ile Pro Val Ser Cys Lys His Ser Gly Gln
1               5                   10                  15

Cys Ser Lys Pro Cys Lys Glu Leu Tyr Gly Ser Ser Ala Gly Ala Lys
            20                  25                  30

Cys Met Asn Gly Lys Cys His Cys Thr Pro Gln Gly Ser Ala Ser Ser
        35                  40                  45

Ala Thr Arg Pro Phe Val Cys Glu Tyr Gln Gly Gln Ser Ser Asp Leu
    50                  55                  60

Pro
65
```

<210> SEQ ID NO 155
<211> LENGTH: 62
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 155

```
Met Ala Ala Glu Val Arg Ile Pro Val Ser Cys Lys His Ser Gly Gln
1               5                   10                  15

Cys Ile Lys Pro Cys Lys Asp Ala Gly Met Arg Phe Gly Lys Cys Met
            20                  25                  30

Asn Lys Lys Cys Arg Cys Tyr Ser Gly Ser Ala Ser Ser Ala Thr Arg
        35                  40                  45

Pro Phe Val Cys Glu Tyr Gln Gly Gln Ser Ser Asp Leu Pro
    50                  55                  60
```

<210> SEQ ID NO 156
<211> LENGTH: 62
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 156

```
Met Ala Ala Glu Val Arg Ile Pro Val Ser Cys Lys His Ser Gly Gln
1               5                   10                  15

Cys Leu Lys Pro Cys Lys Asp Ala Gly Met Arg Phe Gly Lys Cys Met
            20                  25                  30

Asn Gly Lys Cys Arg Cys Tyr Ser Gly Ser Ala Ser Ser Ala Thr Arg
        35                  40                  45

Pro Phe Val Cys Glu Tyr Gln Gly Gln Ser Ser Asp Leu Pro
    50                  55                  60
```

<210> SEQ ID NO 157
<211> LENGTH: 62
<212> TYPE: PRT

<213> ORGANISM: Artificial Sequence
<220> FEATURE:
<223> OTHER INFORMATION: Description of Artificial Sequence: Synthetic
      toxin peptide

<400> SEQUENCE: 157

Met Ala Ala Glu Val Arg Ile Pro Val Ser Cys Lys His Ser Gly Gln
1               5                   10                  15

Cys Leu Glu Pro Cys Lys Lys Ala Gly Met Arg Phe Gly Lys Cys Met
            20                  25                  30

Met Ser Lys Cys Arg Cys Tyr Ser Gly Ser Ala Ser Ser Ala Thr Arg
        35                  40                  45

Pro Phe Val Cys Glu Tyr Gln Gly Gln Ser Ser Asp Leu Pro
    50                  55                  60

<210> SEQ ID NO 158
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 158

Met Ala Ala Glu Val Arg Ile Pro Val Ser Cys Lys His Ser Gly Gln
1               5                   10                  15

Cys Ser Lys Pro Cys Lys Glu Leu Tyr Gly Ser Ser Ala Gly Ala Lys
            20                  25                  30

Cys Met Asn Arg Lys Cys Lys Cys Phe Gly Arg Gly Ser Ala Ser Ser
        35                  40                  45

Ala Thr Arg Pro Phe Val Cys Glu Tyr Gln Gly Gln Ser Ser Asp Leu
    50                  55                  60

Pro
65

<210> SEQ ID NO 159
<211> LENGTH: 62
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 159

Met Ala Ala Glu Val Arg Ile Pro Val Ser Cys Lys His Ser Gly Gln
1               5                   10                  15

Cys Leu Lys Pro Cys Lys Asp Ala Gly Met Arg Phe Gly Lys Cys Met
            20                  25                  30

Asn Gly Lys Cys Arg Cys Tyr Ser Gly Ser Ala Ser Ser Ala Thr Arg
        35                  40                  45

Pro Phe Val Cys Glu Tyr Gln Gly Gln Ser Ser Asp Leu Pro
    50                  55                  60

<210> SEQ ID NO 160
<211> LENGTH: 62
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 160

Met Ala Ala Glu Val Arg Ile Pro Val Ser Cys Lys His Ser Gly Gln

```
                1               5                  10                 15
Cys Leu Lys Pro Cys Lys Asp Leu Tyr Gly Pro His Ala Gly Ala Lys
                20                 25                 30

Cys Met Asn Gly Lys Cys His Cys Gly Ser Ala Ser Ser Ala Thr Arg
            35                 40                 45

Pro Phe Val Cys Glu Tyr Gln Gly Gln Ser Ser Asp Leu Pro
        50                 55                 60

<210> SEQ ID NO 161
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 161

Met Ala Ala Glu Val Arg Ile Pro Val Ser Cys Lys His Ser Gly Gln
1               5                  10                 15

Cys Ile Gln Pro Cys Arg Asp Ala Gly Met Arg Phe Gly Lys Cys Met
                20                 25                 30

Asn Gly Lys Cys His Cys Thr Pro Lys Gly Ser Ala Ser Ser Ala Thr
            35                 40                 45

Arg Pro Phe Val Cys Glu Tyr Gln Gly Gln Ser Ser Asp Leu Pro
        50                 55                 60

<210> SEQ ID NO 162
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 162

Met Ala Ala Glu Val Arg Ile Pro Val Ser Cys Lys His Ser Gly Gln
1               5                  10                 15

Cys Ser Lys Pro Cys Lys Glu Leu Tyr Gly Ser Ser Ala Gly Ala Lys
                20                 25                 30

Cys Met Asn Lys Lys Cys Arg Cys Tyr Ser Gly Ser Ala Ser Ser Ala
            35                 40                 45

Thr Arg Pro Phe Val Cys Glu Tyr Gln Gly Gln Ser Ser Asp Leu Pro
        50                 55                 60

<210> SEQ ID NO 163
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 163

Met Ala Ala Glu Val Arg Ile Pro Val Ser Cys Lys His Ser Gly Gln
1               5                  10                 15

Cys Leu Arg Pro Cys Lys Asp Arg Phe Gly Gln His Ala Gly Gly Lys
                20                 25                 30

Cys Met Asn Gly Lys Cys Lys Cys Tyr Asn Asn Gly Ser Ala Ser Ser
            35                 40                 45

Ala Thr Arg Pro Phe Val Cys Glu Tyr Gln Gly Gln Ser Ser Asp Leu
        50                 55                 60
```

Pro
65

<210> SEQ ID NO 164
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 164

Met Ala Ala Glu Val Arg Ile Pro Val Ser Cys Lys His Ser Gly Gln
1               5                   10                  15

Cys Ile Lys Pro Cys Lys Asp Ala Gly Met Arg Phe Gly Lys Cys Met
                20                  25                  30

Asn Arg Lys Cys Lys Cys Phe Gly Arg Gly Ser Ala Ser Ser Ala Thr
            35                  40                  45

Arg Pro Phe Val Cys Glu Tyr Gln Gly Gln Ser Ser Asp Leu Pro
        50                  55                  60

<210> SEQ ID NO 165
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 165

Met Ala Ala Glu Val Arg Ile Pro Val Ser Cys Lys His Ser Gly Gln
1               5                   10                  15

Cys Leu Lys Pro Cys Lys Asp Leu Tyr Gly Pro His Ala Gly Ala Lys
                20                  25                  30

Cys Met Asn Gly Lys Cys Asp Cys Thr Pro Lys Gly Ser Ala Ser Ser
            35                  40                  45

Ala Thr Arg Pro Phe Val Cys Glu Tyr Gln Gly Gln Ser Ser Asp Leu
        50                  55                  60

Pro
65

<210> SEQ ID NO 166
<211> LENGTH: 62
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 166

Met Ala Ala Glu Val Arg Ile Pro Val Ser Cys Lys His Ser Gly Gln
1               5                   10                  15

Cys Leu Lys Pro Cys Lys Asp Ala Gly Met Arg Phe Gly Lys Cys Met
                20                  25                  30

Asn Lys Lys Cys Arg Cys Tyr Ser Gly Ser Ala Ser Ser Ala Thr Arg
            35                  40                  45

Pro Phe Val Cys Glu Tyr Gln Gly Gln Ser Ser Asp Leu Pro
        50                  55                  60

<210> SEQ ID NO 167
<211> LENGTH: 62
<212> TYPE: PRT
<213> ORGANISM: Artificial Sequence -continued

```
<220> FEATURE:
<223> OTHER INFORMATION: Description of Artificial Sequence: Synthetic
      toxin peptide
<220> FEATURE:
<221> NAME/KEY: MOD_RES
<222> LOCATION: (18)..(18)
<223> OTHER INFORMATION: Any amino acid

<400> SEQUENCE: 167

Met Ala Ala Glu Gly Phe Thr Asp Val Asp Cys Ser Val Ser Lys Gln
1               5                   10                  15

Cys Xaa Pro Val Cys Lys Lys Leu Phe Gly Thr Tyr Arg Gly Lys Cys
            20                  25                  30

Met Asn Gly Lys Cys Lys Cys Tyr Gly Ser Ala Ser Ser Ala Thr Arg
        35                  40                  45

Pro Phe Val Cys Glu Tyr Gln Gly Gln Ser Ser Asp Leu Pro
    50                  55                  60

<210> SEQ ID NO 168
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 168

Met Ala Ala Glu Gly Phe Thr Asp Val Asp Cys Ser Val Ser Lys Gln
1               5                   10                  15

Cys Trp Ser Ile Cys Lys Arg Leu His Asn Thr Asn Arg Gly Lys Cys
            20                  25                  30

Met Asn Gly Lys Cys Lys Cys Tyr Asn Asn Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 169
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 169

Met Ala Ala Glu Gly Phe Thr Asp Val Asp Cys Ser Val Ser Lys Gln
1               5                   10                  15

Cys Trp Ser Ile Cys Lys Arg Leu His Asn Thr Asn Arg Gly Lys Cys
            20                  25                  30

Met Met Ser Lys Cys Arg Cys Tyr Ser Gly Ser Ala Ser Ser Ala Thr
        35                  40                  45

Arg Pro Phe Val Cys Glu Tyr Gln Gly Gln Ser Ser Asp Leu Pro
    50                  55                  60

<210> SEQ ID NO 170
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 170

Met Ala Ala Glu Gly Phe Thr Asp Val Asp Cys Ser Val Ser Lys Gln
```

```
                1               5              10              15
Cys Tyr Pro His Cys Lys Lys Glu Thr Gly Tyr Pro Asn Ala Lys Cys
                20                  25                  30

Met Asn Gly Lys Cys Arg Cys Tyr Ser Gly Ser Ala Ser Ser Ala Thr
                35                  40                  45

Arg Pro Phe Val Cys Glu Tyr Gln Gly Gln Ser Ser Asp Leu Pro
    50                  55                  60

<210> SEQ ID NO 171
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 171

Met Ala Ala Glu Gly Phe Thr Asp Val Asp Cys Ser Val Ser Lys Gln
1               5                  10                  15

Cys Trp Ile Ala Cys Lys Lys Val Thr Gly Ser Thr Gln Gly

<210> SEQ ID NO 174
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 174

Met Ala Ala Glu Gly Phe Thr Asp Val Asp Cys Ser Val Ser Lys Gln
1               5                   10                  15

Cys Leu Pro Pro Cys Lys Ala Gln Phe Gly Ile Arg Ala Gly Ala Lys
            20                  25                  30

Cys Met Asn Gly Lys Cys Lys Cys Tyr Asn Gly Gly Ser Ala Ser Ser
        35                  40                  45

Ala Thr Arg Pro Phe Val Cys Glu Tyr Gln Gly Gln Ser Ser Asp Leu
    50                  55                  60

Pro
65

<210> SEQ ID NO 175
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 175

Met Ala Ala Glu Gly Phe Thr Asp Val Asp Cys Ser Val Ser Lys Gln
1               5                   10                  15

Cys Leu Pro Pro Cys Lys Ala Gln Phe Gly Ile Arg Ala Gly Ala Lys
            20                  25                  30

Cys Met Asn Gly Lys Cys Lys Cys Tyr Pro His Gly Ser Ala Ser Ser
        35                  40                  45

Ala Thr Arg Pro Phe Val Cys Glu Tyr Gln Gly Gln Ser Ser Asp Leu
    50                  55                  60

Pro
65

<210> SEQ ID NO 176
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 176

Met Ala Ala Glu Gly Phe Thr Asp Val Asp Cys Ser Val Ser Lys Gln
1               5                   10                  15

Cys Trp Pro Val Cys Lys Lys Leu Phe Gly Thr Tyr Arg Gly Lys Cys
            20                  25                  30

Met Asn Gly Lys Cys Arg Cys Tyr Ser Gly Ser Ala Ser Ser Ala Thr
        35                  40                  45

Arg Pro Phe Val Cys Glu Tyr Gln Gly Gln Ser Ser Asp Leu Pro
    50                  55                  60

<210> SEQ ID NO 177
<211> LENGTH: 64
<212> TYPE: PRT
<213> ORGANISM: Artificial Sequence -continued

```
<220> FEATURE:
<223> OTHER INFORMATION: Description of Artificial Sequence: Synthetic
      toxin peptide

<400> SEQUENCE: 177

Met Ala Ala Glu Gly Phe Thr Asp Val Asp Cys Ser Val Ser Lys Gln
1               5                   10                  15

Cys Trp Ser Val Cys Lys Asp Leu Phe Gly Val Asp Arg Gly Lys Cys
            20                  25                  30

Met Asn Gly Lys Cys His Cys Thr Pro Gln Gly Ser Ala Ser Ser Ala
        35                  40                  45

Thr Arg Pro Phe Val Cys Glu Tyr Gln Gly Ser Ser Asp Leu Pro
    50                  55                  60

<210> SEQ ID NO 178
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 178

Met Ala Ala Glu Gly Phe Thr Asp Val Asp Cys Ser Val Ser Lys Gln
1               5                   10                  15

Cys Trp Ser Val Cys Lys Asp Leu Phe Gly Val Asp Arg Gly Lys Cys
            20                  25                  30

Met Asn Arg Lys Cys Lys Cys Phe Gly Arg Gly Ser Ala Ser Ser Ala
        35                  40                  45

Thr Arg Pro Phe Val Cys Glu Tyr Gln Gly Ser Ser Asp Leu Pro
    50                  55                  60

<210> SEQ ID NO 179
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 179

Met Ala Ala Glu Gly Val Pro Ile Asn Val Lys Cys Thr Gly Ser Pro
1               5                   10                  15

Gln Cys Ser Lys Pro Cys Lys Glu Leu Tyr Gly Ser Ser Ala Gly Ala
            20                  25                  30

Lys Cys Met Asn Gly Lys Cys Asp Cys Thr Pro Lys Gly Ser Ala Ser
        35                  40                  45

Ser Ala Thr Arg Pro Phe Val Cys Glu Tyr Gln Gly Gln Ser Ser Asp
    50                  55                  60

Leu Pro
65

<210> SEQ ID NO 180
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 180

Met Ala Ala Glu Gly Val Pro Ile Asn Val Lys Cys Thr Gly Ser Pro
1               5                   10                  15
```

-continued

Gln Cys Leu Lys Pro Cys Lys Asp Leu Tyr Gly Pro His Ala Gly Ala
        20                  25                  30

Lys Cys Met Asn Gly Lys Cys His Cys Thr Pro Lys Gly Ser Ala Ser
        35                  40                  45

Ser Ala Thr Arg Pro Phe Val Cys Glu Tyr Gln Gly Gln Ser Ser Asp
        50                  55                  60

Leu Pro
65

<210> SEQ ID NO 181
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 181

Met Ala Ala Glu Gly Val Pro Ile Asn Val Lys Cys Thr Gly Ser Pro
1               5                   10                  15

Gln Cys Ile Lys Pro Cys Lys Asp Ala Gly Met Arg Phe Gly Lys Cys
        20                  25                  30

Met Asn Gly Lys Cys Lys Cys Tyr Asn Asn Gly Ser Ala Ser Ser Ala
        35                  40                  45

Thr Arg Pro Phe Val Cys Glu Tyr Gln Gly Gln Ser Ser Asp Leu Pro
        50                  55                  60

<210> SEQ ID NO 182
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 182

Met Ala Ala Glu Gly Val Pro Ile Asn Val Lys Cys Thr Gly Ser Pro
1               5                   10                  15

Gln Cys Leu Arg Pro Cys Lys Asp Arg Phe Gly Gln His Ala Gly Gly
        20                  25                  30

Lys Cys Met Asn Gly Lys Cys Lys Cys Tyr Pro His Gly Ser Ala Ser
        35                  40                  45

Ser Ala Thr Arg Pro Phe Val Cys Glu Tyr Gln Gly Gln Ser Ser Asp
        50                  55                  60

Leu Pro
65

<210> SEQ ID NO 183
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 183

Met Ala Ala Glu Gly Val Pro Ile Asn Val Lys Cys Thr Gly Ser Pro
1               5                   10                  15

Gln Cys Ser Lys Pro Cys Lys Glu Leu Tyr Gly Ser Ser Ala Gly Ala
        20                  25                  30

Lys Cys Met Asn Gly Lys Cys Asp Cys Thr Pro Lys Gly Ser Ala Ser

```
                35              40              45
Ser Ala Thr Arg Pro Phe Val Cys Glu Tyr Gln Gly Gln Ser Ser Asp
 50                  55                  60

Leu Pro
 65

<210> SEQ ID NO 184
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 184

Met Ala Ala Glu Gly Val Pro Ile Asn Val Lys Cys Thr Gly Ser Pro
 1               5                  10                  15

Gln Cys Ser Lys Pro Cys Lys Glu Leu Tyr Gly Ser Ser Ala Gly Ala
            20                  25                  30

Lys Cys Met Asn Gly Lys Cys Lys Cys Tyr Pro Gly Ser Ala Ser Ser
        35                  40                  45

Ala Thr Arg Pro Phe Val Cys Glu Tyr Gln Gly Gln Ser Ser Asp Leu
 50                  55                  60

Pro
 65

<210> SEQ ID NO 185
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 185

Met Ala Ala Glu Gly Val Pro Ile Asn Val Lys Cys Thr Gly Ser Pro
 1               5                  10                  15

Gln Cys Ile Lys Pro Cys Lys Asp Ala Gly Met Arg Phe Gly Lys Cys
            20                  25                  30

Met Asn Gly Lys Cys Lys Cys Tyr Pro Gly Ser Ala Ser Ser Ala Thr
        35                  40                  45

Arg Pro Phe Val Cys Glu Tyr Gln Gly Gln Ser Ser Asp Leu Pro
 50                  55                  60

<210> SEQ ID NO 186
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 186

Met Ala Ala Glu Gly Val Pro Ile Asn Val Lys Cys Thr Gly Ser Pro
 1               5                  10                  15

Gln Cys Trp Pro Val Cys Lys Gln Met Phe Gly Lys Pro Asn Gly Lys
            20                  25                  30

Cys Met Asn Arg Lys Cys Lys Cys Phe Gly Arg Gly Ser Ala Ser Ser
        35                  40                  45

Ala Thr Arg Pro Phe Val Cys Glu Tyr Gln Gly Gln Ser Ser Asp Leu
 50                  55                  60
```

Pro
65

<210> SEQ ID NO 187
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 187

Met Ala Ala Glu Gly Val Pro Ile Asn Val Lys Cys Thr Gly Ser Pro
1               5                   10                  15

Gln Cys Leu Arg Pro Cys Lys Asp Arg Phe Gly Gln His Ala Gly Lys
            20                  25                  30

Lys Cys Met Gly Lys Lys Cys Arg Cys Tyr Gln Gly Ser Ala Ser Ser
        35                  40                  45

Ala Thr Arg Pro Phe Val Cys Glu Tyr Gln Gly Gln Ser Ser Asp Leu
    50                  55                  60

Pro
65

<210> SEQ ID NO 188
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 188

Met Ala Ala Glu Gly Val Pro Ile Asn Val Lys Cys Thr Gly Ser Pro
1               5                   10                  15

Gln Cys Trp Pro Val Cys Lys Gln Met Phe Gly Lys Pro Asn Gly Lys
            20                  25                  30

Cys Met Asn Gly Lys Cys Arg Cys Tyr Ser Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 189
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 189

Met Ala Ala Glu Gly Val Pro Ile Asn Val Lys Cys Thr Gly Ser Pro
1               5                   10                  15

Gln Cys Leu Pro Lys Cys Lys Glu Ala Ile Gly Lys Ala Ala Gly Lys
            20                  25                  30

Cys Met Asn Gly Lys Cys His Cys Thr Pro Lys Gly Ser Ala Ser Ser
        35                  40                  45

Ala Thr Arg Pro Phe Val Cys Glu Tyr Gln Gly Gln Ser Ser Asp Leu
    50                  55                  60

Pro
65

<210> SEQ ID NO 190

```
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 190

Met Ala Ala Glu Gly Val Pro Ile Asn Val Lys Cys Thr Gly Ser Pro
1               5                   10                  15

Gln Cys Trp Pro Val Cys Lys Gln Met Phe Gly Lys Pro Asn Gly Lys
            20                  25                  30

Cys Met Asn Gly Lys Cys His Cys Thr Pro Gln Gly Ser Ala Ser Ser
        35                  40                  45

Ala Thr Arg Pro Phe Val Cys Glu Tyr Gln Gly Gln Ser Ser Asp Leu
    50                  55                  60

Pro
65

<210> SEQ ID NO 191
<211> LENGTH: 66
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 191

Met Ala Ala Glu Gly Val Pro Ile Asn Val Lys Cys Thr Gly Ser Pro
1               5                   10                  15

Gln Cys Leu Leu Pro Cys Lys Glu Ile Tyr Gly Ile His Ala Gly Ala
            20                  25                  30

Lys Cys Met Asn Arg Lys Cys Lys Cys Phe Gly Arg Gly Ser Ala Ser
        35                  40                  45

Ser Ala Thr Arg Pro Phe Val Cys Glu Tyr Gln Gly Gln Ser Ser Asp
    50                  55                  60

Leu Pro
65

<210> SEQ ID NO 192
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 192

Met Ala Ala Glu Gly Val Pro Ile Asn Val Lys Cys Thr Gly Ser Pro
1               5                   10                  15

Gln Cys Leu Pro Lys Cys Lys Glu Ala Ile Gly Lys Ala Ala Gly Lys
            20                  25                  30

Cys Met Met Ser Lys Cys Arg Cys Tyr Ser Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 193
<211> LENGTH: 64
<212> TYPE: PRT
<213> ORGANISM: Artificial Sequence
<220> FEATURE:
<223> OTHER INFORMATION: Description of Artificial Sequence: Synthetic
```

-continued toxin peptide

<400> SEQUENCE: 193

Met Ala Ala Glu Gly Phe Thr Asn Val Ser Cys Ser Ala Ser Ser G

```
            20                  25                  30

Cys Met Gly Lys Lys Cys Arg Cys Tyr Gln Gly Ser Ala Ser Ser Ala
         35                  40                  45

Thr Arg Pro Phe Val Cys Glu Tyr Gln Gly Gln Ser Ser Asp Leu Pro
     50                  55                  60

<210> SEQ ID NO 197
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 197

Met Ala Ala Glu Gly Phe Thr Asn Val Ser Cys Ser Ala Ser Ser Gln
1               5                   10                  15

Cys Leu Pro Pro Cys Lys Ala Gln Phe Gly Gln Ser Ala Gly Ala Lys
            20                  25                  30

Cys Met Asn Gly Lys Cys His Cys Thr Pro Lys Gly Ser Ala Ser Ser
         35                  40                  45

Ala Thr Arg Pro Phe Val Cys Glu Tyr Gln Gly Gln Ser Ser Asp Leu
     50                  55                  60

Pro
65

<210> SEQ ID NO 198
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 198

Met Ala Ala Glu Gly Phe Thr Asn Val Ser Cys Ser Ala Ser Ser Gln
1               5                   10                  15

Cys Leu Arg Pro Cys Lys Asp Arg Phe Gly Gln His Ala Gly Lys Lys
            20                  25                  30

Cys Met Asn Gly Lys Cys Lys Cys Tyr Gly Ser Ala Ser Ser Ala Thr
         35                  40                  45

Arg Pro Phe Val Cys Glu Tyr Gln Gly Gln Ser Ser Asp Leu Pro
     50                  55                  60

<210> SEQ ID NO 199
<211> LENGTH: 65
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 199

Met Ala Ala Glu Gly Phe Thr Asn Val Ser Cys Ser Ala Ser Ser Gln
1               5                   10                  15

Cys Leu Pro Pro Cys Lys Ala Gln Phe Gly Gln Ser Ala Gly Ala Lys
            20                  25                  30

Cys Met Asn Arg Lys Cys Lys Cys Phe Gly Arg Gly Ser Ala Ser Ser
         35                  40                  45

Ala Thr Arg Pro Phe Val Cys Glu Tyr Gln Gly Gln Ser Ser Asp Leu
     50                  55                  60
```

Pro
65

<210> SEQ ID NO 200
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 200

Met Ala Ala Glu Gly Phe Thr Asn Val Ser Cys Ser Ala Ser Ser Gln
1               5                   10                  15

Cys Tyr Pro His Cys Lys Lys Glu Thr Gly Tyr Pro Asn Ala Lys Cys
            20                  25                  30

Met Met Ser Lys Cys Arg Cys Tyr Ser Gly Ser Ala Ser Ser Ala Thr
        35                  40                  45

Arg Pro Phe Val Cys Glu Tyr Gln Gly Gln Ser Ser Asp Leu Pro
    50                  55                  60

<210> SEQ ID NO 201
<211> LENGTH: 63
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 201

Met Ala Ala Glu Gly Phe Thr Asn Val Ser Cys Ser Ala Ser Ser Gln
1               5                   10                  15

Cys Trp Ser Val Cys Gln Arg Leu His Asn Thr Ser Arg Gly Lys Cys
            20                  25                  30

Met Met Ser Lys Cys Arg Cys Tyr Ser Gly Ser Ala Ser Ser Ala Thr
        35                  40                  45

Arg Pro Phe Val Cys Glu Tyr Gln Gly Gln Ser Ser Asp Leu Pro
    50                  55                  60

<210> SEQ ID NO 202
<211> LENGTH: 64
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 202

Met Ala Ala Glu Gly Phe Thr Asn Val Ser Cys Ser Ala Ser Ser Gln
1               5                   10                  15

Cys Trp Ser Val Cys Lys Asp Leu Phe Gly Val Asp Arg Gly Lys Cys
            20                  25                  30

Met Asn Gly Lys Cys His Cys Thr Pro Gln Gly Ser Ala Ser Ser Ala
        35                  40                  45

Thr Arg Pro Phe Val Cys Glu Tyr Gln Gly Gln Ser Ser Asp Leu Pro
    50                  55                  60

<210> SEQ ID NO 203
<211> LENGTH: 38
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 203

Gly Val Glu Ile Asn Val Lys Cys Ser Gly Ser Pro Gln Cys Leu Lys
1               5                   10                  15

Pro Cys Lys Asp Ala Gly Met Asp Phe Gly Asp Cys Met Asn Asp Lys
            20                  25                  30

Cys His Cys Thr Pro Lys
            35

<210> SEQ ID NO 204
<211> LENGTH: 27
<212> TYPE: PRT
<213> ORGANISM: Conus textile

<400> SEQUENCE: 204

Trp Cys Lys Gln Ser Gly Glu Met Cys Asn Leu Leu Asp Gln Asn Cys
1               5                   10                  15

Cys Asp Gly Tyr Cys Ile Val Leu Val Cys Thr
            20                  25

<210> SEQ ID NO 205
<211> LENGTH: 29
<212> TYPE: PRT
<213> ORGANISM: Conus gloriamaris

<400> SEQUENCE: 205

Val Lys Pro Cys Arg Lys Glu Gly Gln Leu Cys Asp Pro Ile Phe Gln
1               5                   10                  15

Asn Cys Cys Arg Gly Trp Asn Cys Val Leu Phe Cys Val
            20                  25

<210> SEQ ID NO 206
<211> LENGTH: 29
<212> TYPE: PRT
<213> ORGANISM: Conus purpurascens
<220> FEATURE:
<221> NAME/KEY: MOD_RES
<222> LOCATION: (6)..(6)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline

<400> SEQUENCE: 206

Glu Ala Cys Tyr Ala Pro Gly Thr Phe Cys Gly Ile Lys Pro Gly Leu
1               5                   10                  15

Cys Cys Ser Glu Phe Cys Leu Pro Gly Val Cys Phe Gly
            20                  25

<210> SEQ ID NO 207
<211> LENGTH: 31
<212> TYPE: PRT
<213> ORGANISM: Conus striatus
<220> FEATURE:
<221> NAME/KEY: MOD_RES
<222> LOCATION: (14)..(14)
<223> OTHER INFORMATION: Hydroxyproline

<400> SEQUENCE: 207

Asp Gly Cys Ser Ser Gly Gly Thr Phe Cys Gly Ile His Pro Gly Leu
1               5                   10                  15

Cys Cys Ser Glu Phe Cys Phe Leu Trp Cys Ile Thr Phe Ile Asp
            20                  25                  30

```
<210> SEQ ID NO 208
<211> LENGTH: 31
<212> TYPE: PRT
<213> ORGANISM: Conus marmoreus

<400> SEQUENCE: 208

Ala Cys Arg Lys Lys Trp Glu Tyr Cys Ile Val Pro Ile Ile Gly Phe
1               5                   10                  15

Ile Tyr Cys Cys Arg Gly Leu Ile Cys Gly Pro Phe Val Cys Val
            20                  25                  30

<210> SEQ ID NO 209
<211> LENGTH: 31
<212> TYPE: PRT
<213> ORGANISM: Conus marmoreus

<400> SEQUENCE: 209

Ala Cys Ser Lys Lys Trp Glu Tyr Cys Ile Val Pro Ile Leu Gly Phe
1               5                   10                  15

Val Tyr Cys Cys Pro Gly Leu Ile Cys Gly Pro Phe Val Cys Val
            20                  25                  30

<210> SEQ ID NO 210
<211> LENGTH: 22
<212> TYPE: PRT
<213> ORGANISM: Conus geographus
<220> FEATURE:
<221> NAME/KEY: MOD_RES
<222> LOCATION: (6)..(7)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 210

Arg Asp Cys Cys Thr Pro Pro Lys Lys Cys Lys Asp Arg Gln Cys Lys
1               5                   10                  15

Pro Gln Arg Cys Cys Ala
            20

<210> SEQ ID NO 211
<211> LENGTH: 22
<212> TYPE: PRT
<213> ORGANISM: Conus geographus
<220> FEATURE:
<221> NAME/KEY: MOD_RES
<222> LOCATION: (6)..(7)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 211

Arg Asp Cys Cys Thr Pro Pro Arg Lys Cys Lys Asp Arg Arg Cys Lys
1               5                   10                  15

Pro Met Lys Cys Cys Ala
            20

<210> SEQ ID NO 212
<211> LENGTH: 22
<212> TYPE: PRT
<213> ORGANISM: Conus purpurascens
<220> FEATURE:
<221> NAME/KEY: MOD_RES
<222> LOCATION: (8)..(8)
```

```
<223> OTHER INFORMATION: Hydroxyproline
<220> FEATURE:
<221> NAME/KEY: MOD_RES
<222> LOCATION: (18)..(18)
<223> OTHER INFORMATION: Hydroxyproline

<400> SEQUENCE: 212

Glx Arg Leu Cys Cys Gly Phe Pro Lys Ser Cys Arg Ser Arg Gln Cys
1               5                   10                  15

Lys Pro His Arg Cys Cys
            20

<210> SEQ ID NO 213
<211> LENGTH: 22
<212> TYPE: PRT
<213> ORGANISM: Conus stercusmuscarum

<400> SEQUENCE: 213

Glx Arg Cys Cys Asn Gly Arg Arg Gly Cys Ser Ser Arg Trp Cys Arg
1               5                   10                  15

Asp His Ser Arg Cys Cys
            20

<210> SEQ ID NO 214
<211> LENGTH: 35
<212> TYPE: PRT
<213> ORGANISM: Selenocosmia huwena

<400> SEQUENCE: 214

Glu Cys Leu Glu Ile Phe Lys Ala Cys Asn Pro Ser Asn Asp Gln Cys
1               5                   10                  15

Cys Lys Ser Ser Lys Leu Val Cys Ser Arg Lys Thr Arg Trp Cys Lys
            20                  25                  30

Tyr Gln Ile
        35

<210> SEQ ID NO 215
<211> LENGTH: 38
<212> TYPE: PRT
<213> ORGANISM: Hadronyche infesa

<400> SEQUENCE: 215

Lys Cys Leu Ala Glu Ala Ala Asp Cys Ser Pro Trp Ser Gly Asp Ser
1               5                   10                  15

Cys Cys Lys Pro Tyr Leu Cys Ser Cys Ile Phe Phe Tyr Pro Cys Ser
            20                  25                  30

Cys Arg Pro Lys Gly Trp
        35

<210> SEQ ID NO 216
<211> LENGTH: 46
<212> TYPE: PRT
<213> ORGANISM: Anemonia sulcata

<400> SEQUENCE: 216

Gly Ala Ala Cys Leu Cys Lys Ser Asp Gly Pro Asn Thr Arg Gly Asn
1               5                   10                  15

Ser Met Ser Gly Thr Ile Trp Val Phe Gly Cys Pro Ser Gly Trp Asn
            20                  25                  30

Asn Cys Glu Gly Arg Ala Ile Ile Gly Tyr Cys Cys Lys Gln
        35                  40                  45
```

```
<210> SEQ ID NO 217
<211> LENGTH: 55
<212> TYPE: PRT
<213> ORGANISM: Cerebratulus lacteus
<220> FEATURE:
<221> NAME/KEY: MOD_RES
<222> LOCATION: (10)..(10)
<223> OTHER INFORMATION: Hydroxyproline

<400> SEQUENCE: 217

Ala Ser Ala Thr Trp Gly Ala Ala Tyr Pro Ala Cys Glu Asn Asn Cys
1               5                   10                  15

Arg Lys Lys Tyr Asp Leu Cys Ile Arg Cys Gln Gly Lys Trp Ala Gly
            20                  25                  30

Lys Arg Gly Lys Cys Ala Ala His Cys Ile Ile Gln Lys Asn Asn Cys
        35                  40                  45

Lys Gly Lys Cys Lys Lys Glu
    50                  55

<210> SEQ ID NO 218
<211> LENGTH: 42
<212> TYPE: PRT
<213> ORGANISM: Hadronyche versuta

<400> SEQUENCE: 218

Cys Ala Lys Lys Arg Asn Trp Cys Gly Lys Thr Glu Asp Cys Cys Cys
1               5                   10                  15

Pro Met Lys Cys Val Tyr Ala Trp Tyr Asn Glu Gln Gly Ser Cys Gln
            20                  25                  30

Ser Thr Ile Ser Ala Leu Trp Lys Lys Cys
        35                  40

<210> SEQ ID NO 219
<211> LENGTH: 64
<212> TYPE: PRT
<213> ORGANISM: Androctomus australis

<400> SEQUENCE: 219

Val Lys Asp Gly Tyr Ile Val Asp Asp Val Asn Cys Thr Tyr Phe Cys
1               5                   10                  15

Gly Arg Asn Ala Tyr Cys Asn Glu Glu Cys Thr Lys Leu Lys Gly Glu
            20                  25                  30

Ser Gly Tyr Cys Gln Trp Ala Ser Pro Tyr Gly Asn Ala Cys Tyr Cys
        35                  40                  45

Tyr Lys Leu Pro Asp His Val Arg Thr Lys Gly Pro Gly Arg Cys His
    50                  55                  60

<210> SEQ ID NO 220
<211> LENGTH: 42
<212> TYPE: PRT
<213> ORGANISM: Crotalus durissus

<400> SEQUENCE: 220

Tyr Lys Gln Cys His Lys Lys Gly Gly His Cys Phe Pro Lys Glu Lys
1               5                   10                  15

Ile Cys Leu Pro Pro Ser Ser Asp Phe Gly Lys Met Asp Cys Arg Trp
            20                  25                  30

Arg Trp Lys Cys Cys Lys Lys Gly Ser Gly
        35                  40

<210> SEQ ID NO 221
<211> LENGTH: 76
```

```
<212> TYPE: PRT
<213> ORGANISM: Buthotus judaicus

<400> SEQUENCE: 221

Lys Lys Asn Gly Tyr Pro Leu Asp Arg Asn Gly Lys Thr Thr Glu Cys
1               5                   10                  15

Ser Gly Val Asn Ala Ile Ala Pro His Tyr Cys Asn Ser Glu Cys Thr
            20                  25                  30

Lys Val Tyr Tyr Ala Glu Ser Gly Tyr Cys Cys Trp Gly Ala Cys Tyr
        35                  40                  45

Cys Phe Gly Leu Glu Asp Asp Lys Pro Ile Gly Pro Met Lys Asp Ile
    50                  55                  60

Thr Lys Lys Tyr Cys Asp Val Gln Ile Ile Pro Ser
65                  70                  75

<210> SEQ ID NO 222
<211> LENGTH: 54
<212> TYPE: PRT
<213> ORGANISM: Artificial Sequence
<220> FEATURE:
<223> OTHER INFORMATION: Description of Artificial Sequence: Synthetic
      toxin consensus peptide
<220> FEATURE:
<221> NAME/KEY: MOD_RES
<222> LOCATION: (1)..(10)
<223> OTHER INFORMATION: Any amino acid and this region may encompass 2-
      10 residues
<220> FEATURE:
<221> NAME/KEY: MOD_RES
<222> LOCATION: (12)..(16)
<223> OTHER INFORMATION: Any amino acid and this region may encompass 3-
      5 residues
<220> FEATURE:
<221> NAME/KEY: MOD_RES
<222> LOCATION: (18)..(22)
<223> OTHER INFORMATION: Any amino acid and this region may encompass 3-
      5 residues
<220> FEATURE:
<221> NAME/KEY: MOD_RES
<222> LOCATION: (24)..(35)
<223> OTHER INFORMATION: Any amino acid and this region may encompass 7-
      12 residues
<220> FEATURE:
<221> NAME/KEY: MOD_RES
<222> LOCATION: (37)..(41)
<223> OTHER INFORMATION: Any amino acid and this region may encompass 3-
      5 residues
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (45)..(54)
<223> OTHER INFORMATION: Any amino acid and this region may encompass 2-
      10 residues

<400> SEQUENCE: 222

Xaa Xaa Xaa Xaa Xaa Xaa Xaa Xaa Xaa Xaa Cys Xaa Xaa Xaa Xaa Xaa
1               5                   10                  15

Cys Xaa Xaa Xaa Xaa Xaa Cys Xaa Xaa Xaa Xaa Xaa Xaa Xaa Xaa Xaa
            20                  25                  30

Xaa Xaa Xaa Cys Xaa Xaa Xaa Xaa Xaa Cys Xaa Cys Xaa Xaa Xaa Xaa
        35                  40                  45

Xaa Xaa Xaa Xaa Xaa Xaa
    50

<210> SEQ ID NO 223
<211> LENGTH: 56
```

```
<212> TYPE: PRT
<213> ORGANISM: Artificial Sequence
<220> FEATURE:
<223> OTHER INFORMATION: Description of Artificial Sequence: Synthetic
      toxin consensus peptide
<220> FEATURE:
<221> NAME/KEY: MOD_RES
<222> LOCATION: (1)..(10)
<223> OTHER INFORMATION: Any amino acid and this region may encompass 2-
      10 residues
<220> FEATURE:
<221> NAME/KEY: MOD_RES
<222> LOCATION: (13)..(16)
<223> OTHER INFORMATION: Any amino acid and this region may encompass 3-
      4 residues
<220> FEATURE:
<221> NAME/KEY: MOD_RES
<222> LOCATION: (19)..(22)
<223> OTHER INFORMATION: Any amino acid and this region may encompass 3-
      4 residues
<220> FEATURE:
<221> NAME/KEY: MOD_RES
<222> LOCATION: (25)..(36)
<223> OTHER INFORMATION: Any amino acid and this region may encompass 7-
      12 residues
<220> FEATURE:
<221> NAME/KEY: MOD_RES
<222> LOCATION: (40)..(43)
<223> OTHER INFORMATION: Any amino acid and this region may encompass 3-
      4 residues
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (47)..(56)
<223> OTHER INFORMATION: Any amino acid and this region may encompass 2-
      10 residues

<400> SEQUENCE: 223

Xaa Xaa Xaa Xaa Xaa Xaa Xaa Xaa Xaa Xaa Lys Cys Xaa Xaa Xaa Xaa
1               5                   10                  15

Gln Cys Xaa Xaa Xaa Xaa Cys Lys Xaa Xaa Xaa Xaa Xaa Xaa Xaa Xaa
            20                  25                  30

Xaa Xaa Xaa Xaa Lys Cys Met Xaa Xaa Xaa Xaa Cys Xaa Cys Xaa Xaa
        35                  40                  45

Xaa Xaa Xaa Xaa Xaa Xaa Xaa Xaa
    50                  55

<210> SEQ ID NO 224
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 224

Arg Ser Cys Ile Asp Thr Ile Pro Lys Ser Glu Cys Thr Asp Ile Arg
1               5                   10                  15

Cys Arg Thr Glu Glu Lys Thr Lys Tyr Asn Leu Cys Arg Lys Thr Cys
            20                  25                  30

Gly Thr Cys
        35

<210> SEQ ID NO 225
<211> LENGTH: 35
<212> TYPE: PRT
<213> ORGANISM: Artificial Sequence
<220> FEATURE:
```

<223> OTHER INFORMATION: Description of Artificial Sequence: Synthetic
      toxin peptide

<400> SEQUENCE: 225

Arg Ser Cys Ile Asp Thr Ile Pro Lys Ser Thr Cys Thr Gln Phe Gln
1               5                   10                  15

Cys Val Ser Asn Pro Lys Trp Met Lys Thr Asn Cys Arg Lys Thr Cys
            20                  25                  30

Gly Thr Cys
        35

<210> SEQ ID NO 226
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 226

Arg Ser Cys Ile Asp Thr Ile Pro Lys Ser Ala Cys Thr Ala Phe Gln
1               5                   10                  15

Cys Asn Lys Ser Thr Lys Phe Arg Ala Leu Tyr Cys Arg Lys Thr Cys
            20                  25                  30

Gly Thr Cys
        35

<210> SEQ ID NO 227
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 227

Arg Ser Cys Ile Asp Thr Ile Pro Lys Ser Ile Cys Thr Ala Phe Gln
1               5                   10                  15

Cys Gln Arg Ser Val Lys Tyr Arg Phe Lys His Cys Arg Lys Thr Cys
            20                  25                  30

Gly Thr Cys
        35

<210> SEQ ID NO 228
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 228

Arg Ser Cys Ile Asp Thr Ile Pro Lys Ser Arg Cys Thr Ala Phe Gln
1               5                   10                  15

Cys Thr His Ser Met Lys Tyr Arg Leu Glu Lys Cys Arg Lys Thr Cys
            20                  25                  30

Gly Thr Cys
        35

<210> SEQ ID NO 229
<211> LENGTH: 35
<212> TYPE: PRT
<213> ORGANISM: Artificial Sequence
<220> FEATURE:

```
<223> OTHER INFORMATION: Description of Artificial Sequence: Synthetic
      toxin peptide

<400> SEQUENCE: 229

Arg Ser Cys Ile Asp Thr Ile Pro Lys Ser Arg Cys Thr Ala Phe Gln
1               5                   10                  15

Cys Lys His Ser Met Lys Tyr Arg Leu His Phe Cys Arg Lys Thr Cys
            20                  25                  30

Gly Thr Cys
        35

<210> SEQ ID NO 230
<211> LENGTH: 35
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 230

Arg Ser Cys Ile Asp Thr Ile Pro Lys Ser Arg Cys Thr Ala Phe Gln
1               5                   10                  15

Cys Lys His Ser Met Lys Tyr Arg Leu Asp Phe Cys Arg Lys Thr Cys
            20                  25                  30

Gly Thr Cys
        35

<210> SEQ ID NO 231
<211> LENGTH: 37
<212> TYPE: PRT
<213> ORGANISM: Artificial Sequence
<220> FEATURE:
<223> OTHER INFORMATION: Description of Artificial Sequence: Synthetic
      toxin peptide

<400> SEQUENCE: 231

Glx Phe Thr Asn Val Ser Cys Thr Thr Ser Lys Glu Cys Trp Ser Val
1               5                   10                  15

Cys Gln Arg Leu His Asn Thr Ser Arg Gly Lys Gly Met Asn Lys Lys
            20                  25                  30

Cys Arg Cys Tyr Ser
        35
```